(12) United States Patent
Argon et al.

(10) Patent No.: US 7,589,174 B2
(45) Date of Patent: Sep. 15, 2009

(54) GRP94-BASED COMPOSITIONS AND METHODS OF USE THEREOF

(75) Inventors: Yair Argon, Wynnewood, PA (US); Tali Gidalevitz, Evanston, IL (US); Chhanda Biswas, Wynnewood, PA (US)

(73) Assignees: The Children's Hospital of Philadelphia, Philadelphia, PA (US); The University of Chicago, Chicago, IL (US)

( * ) Notice: Subject to any disclaimer, the term of this patent is extended or adjusted under 35 U.S.C. 154(b) by 465 days.

(21) Appl. No.: 10/844,711

(22) Filed: May 12, 2004

(65) Prior Publication Data

US 2005/0063982 A1 Mar. 24, 2005

Related U.S. Application Data

(60) Provisional application No. 60/566,363, filed on Apr. 28, 2004, provisional application No. 60/566,362, filed on Apr. 28, 2004, provisional application No. 60/477,990, filed on Jun. 12, 2003, provisional application No. 60/478,149, filed on Jun. 12, 2003, provisional application No. 60/469,723, filed on May 12, 2003.

(51) Int. Cl.
*C07K 1/00* (2006.01)
*C07K 4/00* (2006.01)
*A61K 39/00* (2006.01)
*A61K 39/385* (2006.01)

(52) U.S. Cl. .................. 530/350; 530/300; 424/184.1; 424/193.1

(58) Field of Classification Search ............... 530/350, 530/300; 424/184.1, 193.1
See application file for complete search history.

(56) References Cited

U.S. PATENT DOCUMENTS

| 5,447,843 | A | 9/1995 | McGuire et al. |
| 2002/0039583 | A1 | 4/2002 | Subjeck et al. |
| 2002/0160496 | A1* | 10/2002 | Gewirth et al. ............... 435/226 |
| 2003/0012794 | A1 | 1/2003 | Srivastava et al. |
| 2006/0029610 | A1 | 2/2006 | Argon |

FOREIGN PATENT DOCUMENTS

| WO | 98/34641 | 8/1998 |
| WO | WO 01/72779 A1 | 10/2001 |
| WO | 02/11669 | 2/2002 |
| WO | WO 02/36574 A1 | 5/2002 |
| WO | WO 03/028750 A1 | 4/2003 |

OTHER PUBLICATIONS

Vogen et al. (2002) J. Biol. Chem., vol. 277 (43), 40742-40750.*
Blachere, N.E. et al. "Heat Shock Protein-Peptide Complexes, Reconstituted In Vitro, Elicit Peptide-specific Cytotoxic T Lymphocyte Response and Tumor Immunity"; J. Exp. Med., 186(8): 1315-1322 (1997).
Reed, R.C. et al. "GRP94-associated enzymatic activities. Resolution by chromatographic fractionation"; J. Biol. Chem., 277(28): 25082-9 (2002).
Srivastava, P.K. et al. "Tumor rejection antigens of chemically induced sarcomas of inbred mice"; PubMed—Proc. Natl. Acad. Sci. USA, 83(10): 3407-11 (1986) [Abstract].
Melnick, J. et al. "The endoplasmic reticulum stress protein GRP94, in addition to BiP, associates with unassembled immunoglobulin chains"; JBC Abstracts—J. Biol. Chem., 267(30): 21303-21306 (1992) [Abstract].
Baker-LePain, J.C. et al. "GRP94 (gp96) and GRP94 N-terminal geldanamycin binding domain elicit tissue nonrestricted tumor suppression"; J. Exp. Med., 196(11): 1447-59 (2002).
Vogen, S. et al. "Radicicol-sensitive Peptide Binding to the N-terminal Portion of GRP94"; The Journal of Biological Chemistry, 277(43): 40742-40750 (2002).
Soldano, K.L. et al. "Structure of the N-terminal Domain of GRP94"; The Journal of Biological Chemistry, 279(48): 48330-48338 (2003).
Reed, R.C. et al. "GRP94/gp96 Elicits ERK Activation in Murine Macrophages"; The Journal of Biological Chemistry, 278(34): 31853-31860 (2003).
Roher, N., et al., "The C-terminal domain of human grp94 protects the catalytic subunit of protein kinase CK2 (CK2 alpha) against thermal aggregation," Eur. J. Biochem. 268:429-436 (2001).
Little, E., et al., "Generation of a mammalian cell deficit in glucose-regulated protein stress induction through targeted ribozyme driven by a stress-inducible promoter," J. Biol. Chem., 270(16):9526-9534, (Apr. 21, 1995).
Nguyen Van, P., et al., "Four intracisternal calcium-binding glycoproteins from rat liver microsomes with high affinity for calcium," J. Biol. Chem., 264(29):17494-17501, (Oct. 15, 1989).
Cala, S.E., et al., "GRP94 resides within cardiac sarcoplasmic reticulum vesicles and is phosphorylated by casein kinase II," J. Biol. Chem., 269(8):5926-5931, (Feb. 25, 1994).
Macer, D.R.J., et al., "Identification of a set of calcium-binding proteins in reticuloplasm, the luminal content of the endoplasmic reticulum," J. Cell Sci., 91:61-70, (1988).
Nigam, S.K., et al., "A set of endoplasmic reticulum proteins possessing properties of molecular chaperones includes Ca2+-binding proteins and members of the thioredoxin superfamily," J. Biol. Chem., 269(3):1744-1749, (Jan. 21, 1994).

\* cited by examiner

*Primary Examiner*—Anne Marie S Wehbe
(74) *Attorney, Agent, or Firm*—Dann, Dorfman, Herrell & Skillman; Kathleen D. Rigaut; Robert C. Netter, Jr.

(57) ABSTRACT

Mini chaperones and methods of use thereof for the treatment of cancer and other disorders are provided. Also provided are tools to facilitate screening therapeutic agents which have selective binding affinity for GRP94.

5 Claims, 38 Drawing Sheets
(14 of 38 Drawing Sheet(s) Filed in Color)

N-terminal domain
Binding to dendritic cells

| µg | 3 | 10 | 3 | 10 | 3 | 10 | 3 | 10 |
| Fuc* | - | - | - | - | + | + | + | + |
| α2M | - | - | + | + | - | - | + | + |

The amino acid sequence of human GRP94

(Genbank accession number NM_003299)

MRALWVLGLCCVLLTFGSVRADDEVDVDGTVEEDLGKSREGSRTDDEVVQR
EEAIKQLDGLNASQIRELREKSEKFAFQAEVNRMMKLIINSLYKNKEIFLRELIS
NASDALDKIRLISLTQEPALSGNEELTVKIKCDKEKNLLHVTDTGVGMTREEL
VKNLGTIAKSGTSEFLNKMTEAQEDGQSTSELIGQFGVGFYSAFLVADKVIVTS
KHNNDTQHIWESDSNEFSVIADPRGNTLGRGTTITLVLKEEASDYLELDTIKNL
VKKYSQFINFPIYVWSSKTETVEEPMEEEAAKEEKEESDDEAAVEEEEEKKP
KTKKVEKTVWDWELMNDIKPIWQRPSKEVEEDEYKAFYKSFSKESDDPMAYI
HFTAEGEVTFKSILFVPTSAPRGLFDEYGSKKSDYIKLYVRKVFITDDFHDMMP
KYLNFVKGVVDSDDLPLNVSRETLQQNKILKVIRKKLVRKTLDMIKKIADDK
YNDTFWKEFGTNIKLGVIEDHSNRTRLAKLLRFQSSHHPTDITSLDQYVERMK
EKQDKIYFMAGSSRKEAESSPFVERLLKKGYEVIYLTEPVDEYCIQALPEFDGK
RFQNVAKEGVKFDESEKTKESREAVEKEFEPLLNWMKDKALKDKIEKAVVSQ
RLTESPCALVASQYGWSGNMERIMKAQAYQTGKDISTNYYASQKKTFEINPRHP
LIRDMLRRIKEDEDDKTVLDLAVVLFETATLRSGYLLPDTKAYGDRIERMLRL
SLNIDPDAKVEEEPEEEPEETAEDTTEDTEQDEDEEMDVGTDEEEETAEESTA
EKDEL

Sequence in orange = the signal sequence of human GRP94;

Sequence in red = the sequence contained in the constructs used in the invention.

Figure 22A

The nucleotide sequence of human GRP94
(Genbank accession number NM003299)

```
   1 gtgggcggac cgcgcggctg gaggtgtgag gatccgaacc caggggtggg gggtggaggc
  61 ggctcctgcg atcgaagggg acttgagact caccggccgc acgccatgag ggccctgtgg
 121 gtgctgggcc tctgctgcgt cctgctgacc ttcgggtcgg tcagagctga cgatgaagtt
 181 gatgtggatg gtacagtaga agaggatctg ggtaaaagta gagaaggatc aaggacggat
 241 gatgaagtag tacagagaga ggaagaagct attcagttgg atggattaaa tgcatcacaa
 301 ataagagaac ttagagagaa gtcggaaaag tttgccttcc aagccgaagt taacagaatg
 361 atgaaactta tcatcaattc attgtataaa aataaagaga ttttcctgag agaactgatt
 421 tcaaatgctt ctgatgcttt agataagata aggctaatat cactgactga tgaaaatgct
 481 ctttctggaa atgaggaact aacagtcaaa attaagtgtg ataaggagaa gaacctgctg
 541 catgtcacag acaccggtgt aggaatgacc agagaagagt tggttaaaaa ccttggtacc
 601 atagccaaat ctgggacaag cgagttttta aacaaaatga ctgaagcaca ggaagatggc
 661 cagtcaactt ctgaattgat tggccagttt ggtgtcggtt tctattccgc cttccttgta
 721 gcagataagg ttattgtcac ttcaaaacac aacaacgata cccagcacat ctgggagtct
 781 gactccaatg aattttctgt aattgctgac ccaagaggaa acactctagg acggggaacg
 841 acaattaccc ttgtcttaaa agaagaagca tctgattacc ttgaattgga tacaattaaa
 901 aatctcgtca aaaatattc acagttcata aactttccta tttatgtatg gagcagcaag
 961 actgaaactg ttgaggagcc catggaggaa gaagaagcag ccaaagaaga gaaagaagaa
1021 tctgatgatg aagctgcagt agaggaagaa gaagaagaaa agaaaccaaa gactaaaaaa
1081 gttgaaaaaa ctgtctggga ctgggaactt atgaatgata tcaaaccaat atggcagaga
1141 ccatcaaaag aagtagaaga agatgaatac aaagctttct acaaatcatt ttcaaaggaa
1201 agtgatgacc ccatggctta tattcacttt actgctgaag ggaagttac cttcaaatca
1261 attttatttg tacccacatc tgctccacgt ggtctgtttg acgaatatgg atctaaaaag
1321 agcgattaca ttaagctcta tgtgcgccgt gtattcatca cagacgactt ccatgatatg
1381 atgcctaaat acctcaatttt tgtcaagggt gtggtggact cagatgatct cccttgaat
1441 gtttcccgcg agactcttca gcaacataaa ctgcttaagg tgattaggaa gaagcttgtt
1501 cgtaaaacgc tggacatgat caagaagatt gctgatgata aatacaatga tactttttgg
1561 aaagaatttg gtaccaacat caagcttggt gtgattgaag accactcgaa tcgaacacgt
1621 cttgctaaac ttcttaggtt ccagtcttct catcatccaa ctgacattac tagcctagac
1681 cagtatgtgg aaagaatgaa ggaaaaacaa gacaaaatct acttcatggc tgggtccagc
1741 agaaaagagg ctgaatcttc tccatttgtt gagcgacttc tgaaaaaggg ctatgaagtt
1801 atttacctca cagaacctgt ggatgaatac tgtattcagg cccttcccga atttgatggg
1861 aagagggttc cagaatgttgc caaggaagga gtgaagttcg atgaaagtga gaaaactaag
1921 gagagtcgtg aagcagttga aaagaatttt gagcctctgc tgaattggat gaaagataaa
1981 gcccttaagg acaagattga aaaggctgtg tgtctcagc gcctgacaga atctccgtgt
2041 gctttggtgg ccagccagta cggatggtct ggcaacatgg agagaatcat gaaagcacaa
2101 gcgtaccaaa cgggcaagga catctctaca aattactatg cgagtcagaa gaaaacattt
2161 gaaattaatc ccagacaccc gctgatcaga gacatgcttc gacgaattaa ggaagatgaa
2221 gatgataaaa cagttttgga tcttgctgtg gttttgtttg aaacagcaac gcttcggtca
2281 gggtatcttt taccagacac taaagcatat ggagatagaa tagaaagaat gcttcgcctc
2341 agtttgaaca ttgaccctga tgcaaggtg aagaagagc ccgaagaaga acctgaagag
2401 acagcagaag acacaacaga agacacagag caagacgaag atgaagaat ggatgtggga
2461 acagatgaag aagaagaaac agcaaaggaa tctacagctg aaaagatga attgtaaatt
2521 atactctcac catttggatc ctgtgtggag agggaatgtg aaatttacat catttctttt
2581 tgggagagac ttgttttgga tgcccctaa tccccttctc cctgcactg taaaatgtgg
2641 gattatgggt cacaggaaaa agtgggtttt ttagttgaat ttttttaac attcctcatg
2701 aatgtaaatt tgtactattt aactgactat tcttgatgta aatcttgtc atgtgtataa
2761 aaataaaaaa gatcccaaat
```

GRP94-BASED COMPOSITIONS AND METHODS OF USE THEREOF

The present invention claims priority to the following U.S. Provisional Applications 60/469,723 filed May 12, 2003, 60/477,990 and 60/478,149 each filed Jun. 12, 2003 and 60/566,362 and 60/566,363 each filed Apr. 28, 2004. The disclosure of each of the foregoing provisional applications is incorporate by reference herein.

Pursuant to 35 U.S.C. §202(c), it is acknowledged that the U.S. Government has certain rights in the invention described herein, which was made in part with funds from the National Institutes of Health, Grant Numbers: CA-74182, and NIH/NIAID RO1 AI30178.

FIELD OF THE INVENTION

This invention relates to the fields of immunomodulation, cancer treatment and embryogenesis. More specifically, the invention provides GRP94 based compositions and methods of use thereof for beneficially and therapeutically impacting these processes.

BACKGROUND OF THE INVENTION

Several publications and patent documents are cited throughout the specification in order to describe the state of the art to which this invention pertains. Each of these citations is incorporated herein by reference as though set forth in full.

Glucose Regulated Protein 94 (GRP94) resides in the endoplasmic reticulum and is a molecular chaperone or stress protein which is a member of the heat shock protein (HSP) 90 family. The family includes the htpG gene in bacteria, HSP82 in yeast, HSP90 α and β in higher eukaryotes and the TRAP1 protein in mitochondria (Buchner, J. 1999. Hsp90 & Co.—a holding for folding. *Trends Biochem Sci* 24:136). HSP 90 proteins are ligand regulated and participate in the conformational maturation of protein substrates involved in diverse cellular activities ranging from cell signaling to bacterial recognition and immunomodulation. Extensive work in cell culture models show that GRP94 expression is regulated by reduced levels of glucose (Lee, A. S., et al., *Transcriptional Regulation of Two Genes Specifically Induced by Glucose Starvation in a Hamster Mutant Fibroblast Cell Line*. J. Biol. Chem., 1983. 258: p. 597-603), perturbations of cellular calcium level (Drummond, I. A., et al., *Depletion of intracellular calcium stores by calcium ionophore A23187 induces the genes for glucose-regulated proteins in hamster fibroblasts*. J. Biol. Chem., 1987. 262(26): p. 12801-5; Little, E. and A. S. Lee, *Generation of a mammalian cell line deficient in glucose-regulated protein stress induction through targeted ribozyme driven by a stress-inducible promoter*. J. Biol. Chem., 1995. 270(16): p. 9526-34) or the redox potential (Kim, Y. K., K. S. Kim, and A. S. Lee, *Regulation of the glucose-regulated protein genes by b-mercaptoethanol requires de novo protein synthesis and correlates with inhibition of protein glycosylation*. J. Cell. Physiol., 1987. 133(3): p. 553-559), inhibition of glycosylation, or activation of the unfolded protein response (Gass, J. N., N. M. Gifford, and J. W. Brewer, *Activation of an unfolded protein response during differentiation of antibody-secreting B cells*. J Biol Chem, 2002. 277(50): p. 49047-54).

Given all the factors that regulate its expression, it is intriguing that GRP94 is absent from the yeast genome, even though yeast cells respond to these stress situations much like mammalian cells. GRP94 is essentially a protein of multicellular organisms, but is clearly not necessary for global protein folding in the ER, nor for the secretory process per se. Therefore, the question arises as to whether and for what processes GRP94 is essential.

Tumors generally contain mutated proteins that often are associated with the transformation process itself. The same mutated proteins also make the tumors biochemically distinct. Accordingly such proteins should be recognized as foreign and elicit vigorous immune response by the T cell arm of the immune system (Velders, M. P., H. Schreiber, and W. M. Kast, *Active immunization against cancer cells: impediments and advances*. Semin Oncol, 1998. 25:69). Yet, despite the natural capabilities of T cells to kill tumor cells, in practice the immune responses to cancer, while detectable, are weak. This is due to the evolution of multiple mechanisms within tumor cells to evade the immune reconnaissance system altogether, or to decrease the "fire power" of T cells.

Srivastava et al., showed that GRP94 within tumors binds peptides (See Tamura, Y., et al., *Immunotherapy of tumors with autologous tumor-derived heat shock protein preparations*. Science, 1997. 278:117-120), is released from dying cells (See Basu, S., et al., *Necrotic but not apoptotic cell death releases heat shock proteins, which deliver a partial maturation signal to dendritic cells and activate the NF-kappa B pathway*. Int Immunol, 2000. 12:1539-1546) and then is taken up by macrophages and/or dendritic cells (See Binder, R. J., D. K. Han, and P. K. Srivastava, *CD91: a receptor for heat shock protein gp96*. Nat Immunol, 2000. 1:151-155; Berwin, B., J. P. Hart, S. Rice, C. Gass, S. V. Pizzo, S. R. Post, and C. V. Nicchitta. 2003. *Scavenger receptor-A mediates gp96/GRP94 and calreticulin internalization by antigen-presenting cells*. Embo J 22:6127), where the peptide dissociates from GRP94 and is transferred onto class I histocompatibility proteins as described by Tamura, Y., et al. (FIG. 1). Because peptides displayed by class I molecules stimulate primarily $CD8^+$ T cells, this so-called "peptide re-presentation" pathway leads to enhanced killer cell activity against the tumors, shown to be increased 10-100 fold by this pathway, in cultured cells by the inventor's laboratory and in mouse models by Srivastava's laboratory (See Suto, R. and P. K. Srivastava, *A mechanism for the specific immunogenicity of heat shock protein-chaperoned peptides*. Science, 1995. 269:1585-1588 and Blachere, N. E., et al., *Heat shock protein-peptide complexes, reconstituted in vitro, elicit peptide-specific cytotoxic T lymphocyte response and tumor immunity*. J. Exp. Med., 1997. 186:1315-1322). GRP94 elicits antigen-presenting cell (APC) activation and directs peptides into the cross-presentation pathways of APC through interactions with Toll-like (APC activation) and endocytic (cross-presentation) receptors of APC (Vabulas, R. M., S. Braedel, N. Hilf, H. Singh-Jasuja, S. Herter, P. Ahmad-Nejad, C. J. Kirschning, C. Da Costa, H. G. Rammensee, H. Wagner, and H. Schild. 2002. *The endoplasmic reticulum-resident heat shock protein Gp96 activates dendritic cells via the Toll-like receptor 2/4 pathway*. J Biol Chem 277:20847).

Very little is known about GRP94 expression during mammalian development, although the processes of differentiation and organogenesis can be considered as involving natural metabolic stress responses. Whether or not the GRP94 is essential during embryonogenesis has not yet been determined.

Based on the foregoing, it is clear that a need exists for further elucidation of the role played by GRP94 and fragments thereof in modulating the immune process. Such information will provide novel GRP94 based therapeutics for the treatment of cancer, viral infections and other metabolic disorders.

SUMMARY OF THE INVENTION

In accordance with the present invention, a nucleic acid encoding a truncated GRP94 mini-chaperone protein is provided. In a preferred embodiment, the nucleic acid encodes a GRP94 protein variant selected from the group consisting of amino acids 34-355 of SEQ ID NO: 2, amino acids 34-221 of SEQ ID NO: 2, and amino acids 70-221 of SEQ ID NO: 2.

A GRP94 mini chaperone protein encoded by the aforementioned nucleic acids is also provided. In yet another aspect, a composition comprising at least one of the mini-chaperone proteins complexed to a biologically relevant peptide contained within a pharmaceutically acceptable carrier is disclosed. Such peptides comprise, without limitation, tumor specific antigens, and viral antigens.

The invention also provides a method for stimulating an immune response to tumor tissue for the treatment of malignancy. An exemplary method entails, the steps of forming a complex between at least one mini-chaperone of the invention and at least one tumor specific peptide comprising a tumor specific antigen; and administering an effective amount of the complex to a patient in need thereof, such that a tumor specific cytotoxic T cell (CTL) response is mounted. The CTL response causes a reduction in said tumor tissue thereby treating the malignancy. Tumor specific peptides can include without limitation, those listed in Table 3. Alternatively, such peptides may be isolated from the patient undergoing treatment for malignancy.

In yet another aspect, the invention provides a method for stimulating an immune response to a viral infection treatment of the infection. An exemplary method entails forming a complex between at least one mini-chaperone of the invention and at least one virus specific peptide comprising an antigen specific for said virus and administering an effective amount of said complex to a patient in need thereof, such that a virus specific cytotoxic T cell (CTL) response is mounted which causes a reduction in said viral load thereby treating said infection.

Also encompassed by the present invention is a transgenic mouse embryo harboring a homozygous null mutation in its endogenous GRP94 gene wherein the mutation has been introduced into said mouse via homologous recombination in embryonic stem cells, and further wherein said mouse does not express a functional mouse GRP94 protein.

GRP94 deficient cell lines derived from the transgenic mouse embryo described above is also disclosed. Such cell lines can include without limitation embryonic stem cell line, stem lines which have been induced to undergo cellular differentiation. Cell types obtainable using the GRP94 deficient cell lines of the invention include, for example, neurons, adipocytes, hepatocytes and lymphocytes.

Methods for screening for therapeutic agents which selectively affect GRP94 activity using the GRP94 deficient cell lines of the invention are also within the scope of the invention. One such method entails administering a test compound to the GRP94 deficient cells and cells derived from wild type mouse embryos and assessing said GRP94-deficient and wild type cells for an alteration in a GRP94-related physiological process, thereby identifying agents which selectively modulate GRP94 activity.

Finally, the invention also discloses a nucleic acid encoding an HSP90 mini chaperone comprising amino acids 1-210 of human HSP90, wherein at least one amino acid residue selected from the group consisting of Thr90, Ile81, Pro82 has been altered to another amino acid. Methods for stimulating an immune response to tumor or viral antigens using the HSP90 mini chaperone are also provided.

BRIEF DESCRIPTION OF THE DRAWINGS

The patent or application file contains at least one drawing executed in color. Copies of this patent or patent application publication with color drawings will be provided by the Office upon request and payment of the necessary fee.

FIG. 1. A minimal portion of GRP94 is sufficient for peptide binding.

FIG. 2. Molecular docking model. The relevant sequence of murine GRP94 (from amino acid 46 to 269) was threaded through the solved structure of the N-terminal domain of yeast HSP90 (PDB file 1YER; [20]), using the BioSym software, and energy minimized. The structure of the peptide VSV8 was taken from the solved structure of the complex of VSV8 and MHC class 1 Kb [9]. VSV8 was then docked onto the modeled GRP94 structure using the program PatchDock (Schneidman-Duhovny, D., Y. Inbar, V. Polak, M. Shatsky, I. Halperin, H. Benyamini, A. Barzilai, O. Dror, N. Haspel, R. Nussinov, and H. J. Wolfson. 2003. Taking geometry to its edge: fast unbound rigid (and hinge-bent) docking. *Proteins* 52:107), assuming that it would bind to GRP94 in the same conformation as to MHC class I. The highest ranking docking solutions are shown. They are divided between two possible sites, shown in green in panel A and B, respectively.

FIG. 3. The radicicol-refractive mutant N34-355 D128N, G132A still binds peptide.

FIG. 4. The predicted peptide binding site is in proximity to a deep hydrophobic pocket and to the inhibitor-binding site.

FIG. 5. Peptide binding affects the environment of the hydrophobic pocket containing Cys117.

FIG. 6. Peptide binding requires His residues.

FIG. 7. Site-Directed mutagenesis demonstrates the importance of histidine 125 for peptide binding.

FIG. 9. Grp94−/− embryos fail to gastrulate.

FIG. 11. grp94−/− embryos do not develop a primitive streak. Analysis of developmental markers in grp94 mutant embryos by whole mount in situ hybridization. In all pairs, the WT embryo is on the left, while the mutant embryo is on the right. All embryos are E7.5 except where noted. The figures shown are representative mutant and WT embryos from 2-7 litters for each marker.

FIG. 12. Analysis of transcription of mesodermal markers.

FIG. 13. Heterozygous mice are normal.

FIG. 14. Growth and stress responses of grp94−/− cells. Wild type and mutant ES cell clones were established from E3.5 blastocysts and adapted to growth without feeders. Cells were either grown in high glucose medium (4.5 g/L)(FIG. 14A), or adapted to growth in low (0.1 g/L) glucose medium (FIG. 14B) and then their growth rates measured over one week (n=3).

FIGS. 22A and 22B show the protein and nucleic acidsequences for full length GRP94. FIG. 22A. GRP94 protein sequence (SEQ ID NO: 2). FIG. 22B. GRP94 nucleic acid (SEQ ID NO: 1).

DETAILED DESCRIPTION OF THE INVENTION

Figure 1A:
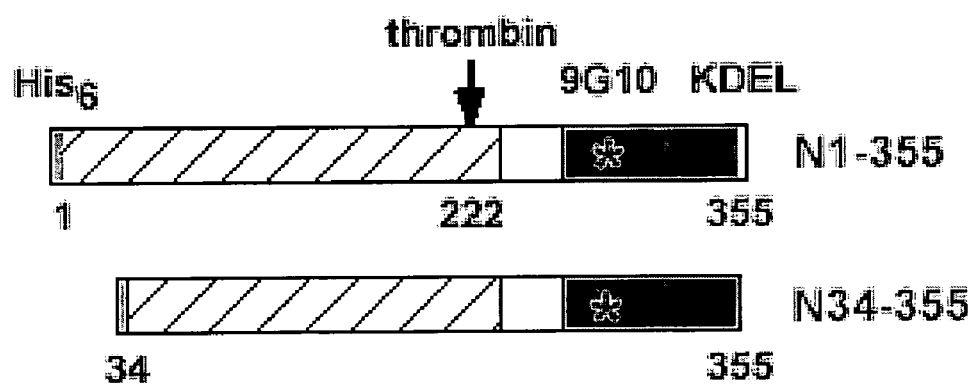
FIG. 1A. Schematic of recombinant proteins used. N1-355, the protein used in [15], contains the first 355 amino acids of GRP94, starting from the DDEVD N-terminus of the mature protein. N34-355 is a version expressed in bacteria, where the first 33 amino acids of mature GRP94 are deleted. Hatched box, the N-terminal domain, containing the nucleotide/geldanamycin/radicicol binding site. Dark grey box, an acidic domain needed for at least one of the activities residing in the N-terminal domain. Light grey box, His6 tag. In N34-355 the tag is followed by a factor Xa cleavage site. N1-355 terminates with a KDEL ER retrieval signal, which is absent in N34-355. The single thrombin cleavage site after Arg222 is marked, as is the region containing the 9G10 monoclonal anti-GRP94 epitope (*).

Since the stress protein GRP94 can augment presentation of peptides to T cells, it is important to define how it, as well as all other HSP90 family members, binds peptides. Having previously shown that the N-terminal half of GRP94 can account for the peptide binding activity of the full-length protein, we now locate this binding site by testing predictions of a molecular docking model. The best predicted site was on the opposite face of the β sheet from the pan-HSP90 radicicol-binding pocket, in close proximity to a deep hydrophobic pocket. The peptide and radicicol binding sites are distinct, as shown by the ability of a radicicol-refractive mutant to bind peptide. When the fluorophore acrylodan is attached to Cys117 within the hydrophobic pocket, its fluorescence is reduced upon peptide binding, consistent with proximity of the two ligands. Substitution of His125, which contacts the bound peptide, compromises peptide binding activity. We conclude that peptide binds to the concave face of the β sheet of the N terminal domain, where binding is regulated during the action cycle of the chaperone. In connection with these studies we have also designed truncated GRP94 polypeptides which retain certain functions of GRP94. Such peptides are useful in screening methods to identify agonists and antagonists of GRP94 mediated biological functions.

GP94 is expressed ubiquitously, but has few known client proteins, none of them involved in important developmental checkpoints. Targeted disruption of the murine GRP94 gene shows that it has an essential function in embryonic development. Grp94−/− embryos die in utero on day 7 of gestation, at the egg cylinder stage of development. They fail to develop mesoderm, a primitive streak, and the proamniotic cavity, the main differentiation events that normally occur at that stage and do not express key genes involved in mesoderm induction. The developmental defect is not due to dilution of maternal GRP94 and seems to reflect the activities of the chaperone. Grp94−/− cells divide at similar pace to their wild type counterparts. Furthermore, despite the known transcriptional regulation of GPR94 by low glucose tension, mutant ES cells proliferated like wild type cells in low glucose medium. On the other hand, mutant cells were much more sensitive to serum deprivation as well as to perturbation of calcium homeostasis. These data suggest that the requirements for GRP94 are very selective. We hypothesize that some secreted or cell-surface proteins, critical for mesoderm induction, depend on GRP94 for their proper expression, and that in the absence of this chaperone they fail to be efficiently presented when cell-cell interactions specify the proper fates of embryonic cells.

GRP 94 plays a role in tumor rejection. Enhancing this activity should prove useful for the treatment of malignancy. Accordingly, the GRP94 based compositions of the invention can be used in the creation of tumor vaccines.

The following definitions are provided to facilitate an understanding of the present invention.

Following long-standing patent law convention, the terms "a" and "an" mean "one or more" when used in this application, including the claims.

As used herein the term "GRP94 protein" is meant to refer to a molecular chaperone which resides in the endoplasmic reticulum and is also known in the art as gp96, ERp99, and endoplasmin. GRP94 is found only in higher plants and metazoans (Nicchitta (1998) Curr Opin Immunol 10:103-109). Stress proteins such as GRP94 are involved in directing the proper folding and trafficking of newly synthesized proteins and in conferring protection to the cell during conditions of heat shock, oxidative stress, hypoxic/anoxic conditions, nutrient deprivation, other physiological stresses, and disorders or traumas that promote such stress conditions such as, for example, stroke and myocardial infarction.

As used herein, the term "ligand binding domain (LBD) of GRP94" refers to the region of GRP94 where the nucleotides ADP, ATP or NECA, or the fungal metabolites geldanamycin, 17AAG or radicicol bind. Our work shows that GRP94 LBD fragments comprising amino acids 34-355 of (SEQ ID NO: 2, 34-221 of SEQ ID NO: 2, and 70-221 of (SEQ ID NO: 2of mammalian (human, canine) GRP94are sufficient for the binding activities of the entire, full-length protein.

As used herein, the terms "binding pocket of the GRP94 ligand binding domain", "GRP94 ligand binding pocket" and "GRP94 binding pocket" are used interchangeably, and refer to the large cavity within the GRP94 ligand binding domain (LBD) where a ligand can bind. This cavity can be empty, or can contain water molecules or other molecules from the solvent, or can contain ligand atoms. The binding pocket also includes regions of space near the "main" binding pocket not occupied by atoms of GRP94 but that are near the "main" binding pocket, and that are contiguous with the "main" binding pocket.

"Antigenic molecule" as used herein refers to the peptides with which GRP94 endogenously associates in vivo (e.g., in infected cells or precancerous or cancerous tissue) as well as exogenous antigens/immunogens (i.e., not complexed with GRP94 in vivo) or antigenic/immunogenic fragments and derivatives thereof.

The phrase "shared tumor antigens" refers to those tumor specific antigens that are commonly found in patients having similar tumor types. Representative shared tumor antigens are provided in Table 3.

The term "biological activity" is meant to refer to a molecule having a biological or physiological effect in a subject. Adjuvant activity is an example of a biological activity. Activating or inducing production of other biological molecules having adjuvant activity is also a contemplated biological activity.

The term "adjuvant activity" is meant to refer to a molecule having the ability to enhance or otherwise modulate the response of a vertebrate subject's immune system to an antigen.

The term "immune system" includes all the cells, tissues, systems, structures and processes, including non-specific and specific categories, that provide a defense against antigenic molecules, including potential pathogens, in a vertebrate subject. As is well known in the art, the non-specific immune system includes phagocytic cells such as neutrophils, monocytes, tissue macrophages, Kupffer cells, alveolar macrophages, dendritic cells and microglia. The specific immune system refers to the cells and other structures that impart specific immunity within a host. Included among these cells are the lymphocytes, particularly the B cell lymphocytes and the T cell lymphocytes. These cells also include natural killer (NK) cells. Additionally, antibody-producing cells, like B lymphocytes, and the antibodies produced by the antibody-producing cells are also included within the term "immune system".

The term "immune response" is meant to refer to any response to an antigen or antigenic determinant by the immune system of a vertebrate subject. Exemplary immune responses include humoral immune responses (e.g. production of antigen-specific antibodies) and cell-mediated immune responses (e.g. lymphocyte proliferation), as defined herein below.

The term "systemic immune response" is meant to refer to an immune response in the lymph node-, spleen-, or gut-associated lymphoid tissues wherein cells, such as B lymphocytes, of the immune system are developed. For example, a systemic immune response can comprise the production of serum IgG's. Further, systemic immune response refers to antigen-specific antibodies circulating in the blood stream and antigen-specific cells in lymphoid tissue in systemic compartments such as the spleen and lymph nodes.

The terms "humoral immunity" or "humoral immune response" are meant to refer to the form of acquired immunity in which antibody molecules are secreted in response to antigenic stimulation.

The terms "cell-mediated immunity" and "cell-mediated immune response" are meant to refer to the immunological defense provided by lymphocytes, such as that defense provided by T cell lymphocytes when they come into close proximity to their victim cells. A cell-mediated immune response also comprises lymphocyte proliferation. When "lymphocyte proliferation" is measured, the ability of lymphocytes to divide in response to specific antigen is measured. Lymphocyte proliferation is meant to refer to B cell, T-helper cell or CTL cell proliferation.

The term "CTL response" is meant to refer to the ability of an antigen-specific cell to lyse and kill a cell expressing the specific antigen. As described herein below, standard, art-recognized CTL assays are performed to measure CTL activity. In such assays, the cell which is being killed is referred to as the "target cell".

"Adoptive immunotherapy" as used herein refers to a therapeutic approach with particular applicability to cancer whereby immune cells with an antitumor reactivity are administered to a tumor-bearing host, with the aim that the cells mediate either directly or indirectly, the regression of an established tumor.

An "immunogenic composition" is meant to refer to a composition that can elicit an immune response. A vaccine is contemplated to fall within the meaning of the term "immunogenic composition", in accordance with the present invention.

The term "a biological response modifier" is meant to refer to a molecule having the ability to enhance or otherwise modulate a subject's response to a particular stimulus, such as presentation of an antigen.

As used herein, the terms "candidate substance" and "candidate compound" are used interchangeably and refer to a substance that is believed to interact with another moiety as a biological response modifier. For example, a representative candidate compound is believed to interact with a complete GRP94 protein, or fragment thereof, and which can be subsequently evaluated for such an interaction. Exemplary candidate compounds that can be investigated using the methods of the present invention include, but are not restricted to, agonists and antagonists of a GRP 94 protein, viral epitopes, peptides, enzymes, enzyme substrates, co-factors, lectins, sugars, oligonucleotides or nucleic acids, oligosaccharides, proteins, chemical compounds small molecules, and monoclonal antibodies.

As used herein, the term "modulate" means an increase, decrease, or other alteration of any or all chemical and biological activities or properties of a wild-type or mutant GRP94 polypeptide. The term "modulation" as used herein refers to both upregulation (i.e., activation or stimulation) and downregulation (i.e. inhibition or suppression) of a response.

As used herein, the term "agonist" means an agent that supplements or potentiates the biological activity of a functional GRP94 protein.

As used herein, the term "antagonist" means an agent that decreases or inhibits the biological activity of a functional GRP94 protein, or that supplements or potentiates the biological activity of a naturally occurring or engineered non-functional GRP94 protein.

As used herein, the term "alpha helix" refers to the conformation of a polypeptide chain wherein the polypeptide backbone is wound around the long axis of the molecule in a left-handed or right-handed direction, and the R groups of the amino acids protrude outward from the helical backbone, wherein the repeating unit of the structure is a single turnoff the helix, which extends about 0.56 nm along the long axis.

As used herein, the term "β strand" refers to the conformation of a polypeptide chain stretched into an extended zig-zig conformation. β strands of polypeptide chains aligned side-by-side form "β sheets". Strands that run "parallel" all run in the same direction. Strands of polypeptide chains that are "antiparallel" run in the opposite direction to each other.

As used herein, the terms "cells," "host cells" or "recombinant host cells" are used interchangeably and mean not only to the particular subject cell, but also to the progeny or potential progeny of such a cell. Because certain modifications can occur in succeeding generations due to either mutation or environmental influences, such progeny might not, in fact, be identical to the parent cell, but are still included within the scope of the term as used herein.

The terms "chimeric protein" or "fusion protein" are used interchangeably herein and mean a fusion of a first amino acid sequence encoding a GRP94 polypeptide with a second amino acid sequence defining a polypeptide domain foreign to, and not homologous with, any domain of GRP94. For example, a chimeric protein can include a foreign domain that is found in an organism that also expresses the first protein, or it can be an "interspecies" or "intergenic" fusion of protein structures expressed by different kinds of organisms. In general, a fusion protein can be represented by the general formula X-GRP94-Y, wherein GRP94 represents a portion of the protein which is derived from a GRP94 polypeptide, and X and Y are independently absent or represent amino acid sequences which are not related to a GRP94 sequence in an organism, which includes naturally occurring mutants.

As used herein, the term "detecting" means confirming the presence of a target entity by observing the occurrence of a detectable signal, such as a radiologic, spectroscopic or another signal that will appear exclusively in the presence of the target entity.

As used herein, the term "interact" means detectable interactions between molecules, such as can be detected using, for example, a yeast two-hybrid assay. The term "interact" is also meant to include "binding" interactions between molecules. Interactions can, for example, be protein-protein or protein-nucleic acid in nature.

As used herein, the term "modified" means an alteration from an entity's normally occurring state. An entity can be modified by removing discrete chemical units or by adding discrete chemical units. The term "modified" encompasses detectable labels as well as those entities added as aids in purification.

As used herein, the term "mutation" carries its traditional connotation and means a change, inherited, naturally occurring or introduced, in a nucleic acid or polypeptide sequence, and is used in its sense as generally known to those of skill in the art.

As used herein, the term "partial agonist" means an entity that can bind to a target and induce only part of the changes in the target that are induced by agonists. The differences can be qualitative or quantitative. Thus, a partial agonist can induce some of the conformation changes induced by agonists, but not others, or it can only induce certain changes to a limited extent.

As used herein, the term "partial antagonist" means an entity that can bind to a target and inhibit only part of the changes in the target that are induced by antagonists. The differences can be qualitative or quantitative. Thus, a partial antagonist can inhibit some of the conformation changes induced by an antagonist, but not others, or it can inhibit certain changes to a limited extent.

"Nucleic acid" or a "nucleic acid molecule" as used herein refers to any DNA or RNA molecule, either single or double stranded and, if single stranded, the molecule of its complementary sequence in either linear or circular form. In discussing nucleic acid molecules, a sequence or structure of a particular nucleic acid molecule may be described herein according to the normal convention of providing the sequence in the 5' to 3' direction. With reference to nucleic acids of the invention, the term "isolated nucleic acid" is sometimes used. This term, when applied to DNA, refers to a DNA molecule that is separated from sequences with which it is immediately contiguous in the naturally occurring genome of the organism in which it originated. For example, an "isolated nucleic acid" may comprise a DNA molecule inserted into a vector, such as a plasmid or virus vector, or integrated into the genomic DNA of a prokaryotic or eukaryotic cell or host organism.

When applied to RNA, the term "isolated nucleic acid" refers primarily to an RNA molecule encoded by an isolated DNA molecule as defined above. Alternatively, the term may refer to an RNA molecule that has been sufficiently separated from other nucleic acids with which it would be associated in its natural state (i.e., in cells or tissues). An "isolated nucleic acid" (either DNA or RNA) may further represent a molecule produced directly by biological or synthetic means and separated from other components present during its production.

The terms "percent similarity", "percent identity" and "percent homology" when referring to a particular sequence are used as set forth in the University of Wisconsin GCG software program.

The term "substantially pure" refers to a preparation comprising at least 50 60% by weight of a given material (e.g., nucleic acid, oligonucleotide, protein, etc.). More preferably, the preparation comprises at least 75% by weight, and most preferably 90-95% by weight of the given compound. Purity is measured by methods appropriate for the given compound (e.g. chromatographic methods, agarose or polyacrylamide gel electrophoresis, HPLC analysis, and the like).

A "replicon" is any genetic element, for example, a plasmid, cosmid, bacmid, plastid, phage or virus, that is capable of replication largely under its own control. A replicon may be either RNA or DNA and may be single or double stranded.

A "vector" is a replicon, such as a plasmid, cosmid, bacmid, phage or virus, to which another genetic sequence or element (either DNA or RNA) may be attached so as to bring about the replication of the attached sequence or element.

An "expression operon" refers to a nucleic acid segment that may possess transcriptional and translational control sequences, such as promoters, enhancers, translational start signals (e.g., ATG or AUG codons), polyadenylation signals, terminators, and the like, and which facilitate the expression of a polypeptide coding sequence in a host cell or organism.

The term "oligonucleotide" as used herein refers to sequences, primers and probes of the present invention, and is defined as a nucleic acid molecule comprised of two or more ribo or deoxyribonucleotides, preferably more than three. The exact size of the oligonucleotide will depend on various factors and on the particular application and use of the oligonucleotide.

The phrase "specifically hybridize" refers to the association between two single stranded nucleic acid molecules of sufficiently complementary sequence to permit such hybridization under pre determined conditions generally used in the art (sometimes termed "substantially complementary"). In particular, the term refers to hybridization of an oligonucleotide with a substantially complementary sequence contained within a single stranded DNA or RNA molecule of the invention, to the substantial exclusion of hybridization of the oligonucleotide with single stranded nucleic acids of non complementary sequence.

The term "probe" as used herein refers to an oligonucleotide, polynucleotide or nucleic acid, either RNA or DNA, whether occurring naturally as in a purified restriction enzyme digest or produced synthetically, which is capable of annealing with or specifically hybridizing to a nucleic acid with sequences complementary to the probe. A probe may be either single stranded or double stranded. The exact length of the probe will depend upon many factors, including temperature, source of probe and method of use. For example, for diagnostic applications, depending on the complexity of the target sequence, the oligonucleotide probe typically contains 15 25 or more nucleotides, although it may contain fewer nucleotides. The probes herein are selected to be "substantially" complementary to different strands of a particular target nucleic acid sequence. This means that the probes must be sufficiently complementary so as to be able to "specifically hybridize" or anneal with their respective target strands under a set of pre-determined conditions. Therefore, the probe sequence need not reflect the exact complementary sequence of the target. For example, a non complementary nucleotide fragment may be attached to the 5' or 3' end of the probe, with the remainder of the probe sequence being complementary to the target strand. Alternatively, non complementary bases or longer sequences can be interspersed into the probe, provided that the probe sequence has sufficient complementarity with the sequence of the target nucleic acid to anneal therewith specifically.

The term "primer" as used herein refers to an oligonucleotide, either RNA or DNA, either single stranded or double stranded, either derived from a biological system, generated by restriction enzyme digestion, or produced synthetically which, when placed in the proper environment, is able to functionally act as an initiator of template-dependent nucleic acid synthesis. When presented with an appropriate nucleic acid template, suitable nucleoside triphosphate precursors of nucleic acids, a polymerase enzyme, suitable cofactors and conditions such as appropriate temperature and pH, the primer may be extended at its 3' terminus by the addition of nucleotides by the action of a polymerase or similar activity to yield a primer extension product. The primer may vary in length depending on the particular conditions and requirement of the application. For example, in diagnostic applications, the oligonucleotide primer is typically 15-25 or more nucleotides in length. The primer must be of sufficient complementarity to the desired template to prime the synthesis of the desired extension product, that is, to be able to anneal with the desired template strand in a manner sufficient to provide the 3' hydroxyl moiety of the primer in appropriate juxtaposition for use in the initiation of synthesis by a polymerase or similar enzyme. It is not required that the primer sequence represent an exact complement of the desired template. For example, a non complementary nucleotide sequence may be attached to the 5' end of an otherwise complementary primer. Alternatively, non complementary bases may be interspersed within the oligonucleotide primer sequence, provided that the primer sequence has sufficient complementarity with the sequence of the desired template strand to functionally provide a template primer complex for the synthesis of the extension product.

Polymerase chain reaction (PCR) has been described in U.S. Pat. Nos. 4,683,195, 4,800,195, and 4,965,188, the entire disclosures of which are incorporated by reference herein.

As used herein, the terms "reporter," "reporter system", "reporter gene," or "reporter gene product" shall mean an operative genetic system in which a nucleic acid comprises a gene that encodes a product that when expressed produces a reporter signal that is a readily measurable, e.g., by biological assay, immunoassay, radio immunoassay, or by colorimetric, fluorogenic, chemiluminescent or other methods. The nucleic acid may be either RNA or DNA, linear or circular, single or double stranded, antisense or sense polarity, and is operatively linked to the necessary control elements for the expression of the reporter gene product. The required control elements will vary according to the nature of the reporter system and whether the reporter gene is in the form of DNA or RNA, but may include, but not be limited to, such elements as promoters, enhancers, translational control sequences, poly A addition signals, transcriptional termination signals and the like.

The terms "transform", "transfect", "transduce", shall refer to any method or means by which a nucleic acid is introduced into a cell or host organism and may be used interchangeably to convey the same meaning. Such methods include, but are not limited to, transfection, electroporation, microinjection, PEG-fusion and the like.

The introduced nucleic acid may or may not be integrated (covalently linked) into nucleic acid of the recipient cell or organism. In bacterial, yeast, plant and mammalian cells, for example, the introduced nucleic acid may be maintained as an episomal element or independent replicon such as a plasmid. Alternatively, the introduced nucleic acid may become integrated into the nucleic acid of the recipient cell or organism and be stably maintained in that cell or organism and further passed on or inherited to progeny cells or organisms of the recipient cell or organism. Finally, the introduced nucleic acid may exist in the recipient cell or host organism only transiently.

The term "selectable marker gene" refers to a gene that when expressed confers a selectable phenotype, such as antibiotic resistance, on a transformed cell or plant.

The term "operably linked" means that the regulatory sequences necessary for expression of the coding sequence are placed in the DNA molecule in the appropriate positions relative to the coding sequence so as to effect expression of the coding sequence. This same definition is sometimes applied to the arrangement of transcription units and other transcription control elements (e.g. enhancers) in an expression vector.

Amino acid residues are identified in the present application according to conventional three letter or one letter abbreviations.

Amino acid residues described herein are preferred to be in the "L" isomeric form. However, residues in the "D" isomeric form may be substituted for any L amino acid residue, provided the desired properties of the polypeptide are retained. All amino acid residue sequences represented herein conform to the conventional left-to-right amino terminus to carboxy terminus orientation.

The term "isolated protein" or "isolated and purified protein" is sometimes used herein. This term refers primarily to a protein produced by expression of an isolated nucleic acid molecule of the invention. Alternatively, this term may refer to a protein that has been sufficiently separated from other proteins with which it would naturally be associated, so as to exist in "substantially pure" form. "Isolated" is not meant to exclude artificial or synthetic mixtures with other compounds or materials, or the presence of impurities that do not interfere with the fundamental activity, and that may be present, for example, due to incomplete purification, or the addition of stabilizers.

"Mature protein" or "mature polypeptide" shall mean a polypeptide possessing the sequence of the polypeptide after any processing events that normally occur to the polypeptide during the course of its genesis, such as proteolytic processing from a polyprotein precursor. In designating the sequence or boundaries of a mature protein, the first amino acid of the mature protein sequence is designated as amino acid residue 1. As used herein, any amino acid residues associated with a mature protein not naturally found associated with that protein that precedes amino acid 1 are designated amino acid –1, 2, 3 and so on. For recombinant expression systems, a methionine initiator codon is often utilized for purposes of efficient translation. This methionine residue in the resulting polypeptide, as used herein, would be positioned at –1 relative to the mature GRP94 protein sequence.

A low molecular weight "peptide analog" shall mean a natural or mutant (mutated) analog of a GRP94 protein, comprising a linear or discontinuous series of fragments of that protein and which may have one or more amino acids replaced with other amino acids and which has altered, enhanced or diminished biological activity when compared with the parent or non-mutated protein.

The present invention also includes active portions, fragments, derivatives and functional or non functional mimetics of GRP94 polypeptides, or proteins of the invention. An "active portion" of such a polypeptide means a peptide that is less than the full length polypeptide, but which retains measurable biological activity.

A "fragment" or "portion" of a GRP94 polypeptide means a stretch of amino acid residues of at least about five to seven contiguous amino acids, often at least about seven to nine contiguous amino acids, typically at least about nine to thirteen contiguous amino acids and, most preferably, at least about twenty to thirty or more contiguous amino acids. Fragments of the GRP94 polypeptide sequence, antigenic determinants, or epitopes are useful for eliciting immune responses to a portion of the GRP94 protein amino acid sequence for the effective production of immunospecific anti-GRP94 antibodies.

Different "variants" of the GRP94 polypeptides exist in nature. These variants may be alleles characterized by differences in the nucleotide sequences of the gene coding for the protein, or may involve different RNA processing or post translational modifications. The skilled person can produce variants having single or multiple amino acid substitutions, deletions, additions or replacements. These variants may include but are not limited to: (a) variants in which one or more amino acids residues are substituted with conservative or non conservative amino acids, (b) variants in which one or more amino acids are added to the polypeptide, (c) variants in which one or more amino acids include a substituent group, and (d) variants in which the polypeptide is fused with another peptide or polypeptide such as a fusion partner, a protein tag or other chemical moiety, that may confer useful properties to the GRP94-related polypeptide, such as, for example, an epitope for an antibody, a polyhistidine sequence, a membrane fusion sequence, a cytoplasmic targeting sequence, a nuclear targeting sequence, a biotin moiety and the like. Other GRP94 polypeptides of the invention include variants in which amino acid residues from one species are substituted for the corresponding residue in another species, either at the conserved or non conserved positions. In another embodiment, amino acid residues at non conserved positions are substituted with conservative or non conservative residues. The techniques for obtaining these variants, including genetic (suppressions, deletions, mutations, etc.), chemical, and enzymatic techniques are known to the person having ordinary skill in the art. To the extent such allelic variations, analogues, fragments, derivatives, mutants, and modifications, including alternative nucleic acid processing forms and alternative post translational modification forms, result in derivatives of the apoptosis modulator polypeptides that retain any of the biological properties of the GRP94s, they are included within the scope of this invention.

The term "functional" as used herein implies that the nucleic or amino acid sequence is functional for the recited assay or purpose.

The phrase "consisting essentially of" when referring to a particular nucleotide or amino acid means a sequence having the properties of a given SEQ ID NO. For example, when used in reference to an amino acid sequence, the phrase includes the sequence per se and molecular modifications that would not affect the basic and novel characteristics of the sequence.

The term "tag," "tag sequence" or "protein tag" refers to a chemical moiety, either a nucleotide, oligonucleotide, polynucleotide or an amino acid, peptide or protein or other chemical, that when added to another sequence, provides additional utility or confers useful properties, particularly in the detection or isolation, of that sequence. Thus, for example, a homopolymer nucleic acid sequence or a nucleic acid sequence complementary to a capture oligonucleotide may be added to a primer or probe sequence to facilitate the subsequent isolation of an extension product or hybridized product. In the case of protein tags, histidine residues (e.g., 4 to 8 consecutive histidine residues) may be added to either the amino or carboxy terminus of a protein to facilitate protein isolation by chelating metal chromatography. Alternatively, amino acid sequences, peptides, proteins or fusion partners representing epitopes or binding determinants reactive with specific antibody molecules or other molecules (e.g., flag epitope, c myc epitope, transmembrane epitope of the influenza A virus hemaglutinin protein, protein A, cellulose binding domain, calmodulin binding protein, maltose binding protein, chitin binding domain, glutathione S transferase, and the like) may be added to proteins to facilitate protein isolation by procedures such as affinity or immunoaffinity chromatography. Chemical tag moieties include such molecules as biotin, which may be added to either nucleic acids or proteins and facilitates isolation or detection by interaction with avidin reagents, and the like. Numerous other tag moieties are known to, and can be envisioned by the trained artisan, and are contemplated to be within the scope of this definition.

A "clone" or "clonal cell population" is a population of cells derived from a single cell or common ancestor by mitosis.

A "cell line" is a clone of a primary cell or cell population that is capable of stable growth in vitro for many generations.

An "antibody" or "antibody molecule" is any immunoglobulin, including antibodies and fragments thereof, that binds to a specific antigen, such as epitopes of an GRP94 protein. The term includes polyclonal, monoclonal, chimeric, and bispecific antibodies. As used herein, antibody or antibody molecule contemplates both an intact immunoglobulin molecule and an immunologically active portion of an immunoglobulin molecule such as those portions known in the art as Fab, Fab', F(ab')2 and F(v).

I. Preparation of GRP94-Encoding Nucleic Acid Molecules, GRP94 Polypeptides, and Fragments Thereof A. Nucleic Acid Molecules Nucleic acid molecules encoding the GRP94-related sequences of the invention may be prepared by two general methods: (1) Synthesis from appropriate nucleotide triphosphates, or (2) Isolation from biological sources. Both methods utilize protocols well known in the art.

The availability of nucleotide sequence information, such as the full length cDNA having Sequence I.D. No. 1, enables preparation of an isolated nucleic acid molecule of the invention by oligonucleotide synthesis. Synthetic oligonucleotides may be prepared by the phosphoramidite method employed in the Applied Biosystems 38A DNA Synthesizer or similar devices. The resultant construct may be purified according to methods known in the art, such as high performance liquid chromatography (HPLC). Long, double-stranded polynucleotides, such as a DNA molecule of the present invention, must be synthesized in stages, due to the size limitations inherent in current oligonucleotide synthetic methods. Thus, for example, a 2.4 kb double-stranded molecule may be synthesized as several smaller segments of appropriate complementarity. Complementary segments thus produced may be annealed such that each segment possesses appropriate cohesive termini for attachment of an adjacent segment. Adjacent segments may be ligated by annealing cohesive termini in the presence of DNA ligase to construct an entire 2.4 kb double-stranded molecule. A synthetic DNA molecule so constructed may then be cloned and amplified in an appropriate vector.

Nucleic acid sequences encoding GRP94 or homologs thereof may be isolated from appropriate biological sources using methods known in the art. In a preferred embodiment, a cDNA clone is isolated from a cDNA expression library of human origin. In an alternative embodiment, utilizing the sequence information provided by the cDNA sequence, genomic clones encoding GRP94 may be isolated. Alternatively, cDNA or genomic clones having homology with GRP94 may be isolated from other species, such as mouse, using oligonucleotide probes corresponding to predetermined sequences within the GRP94 gene.

In accordance with the present invention, nucleic acids having the appropriate level of sequence homology with the protein coding region of Sequence I.D. No. 1 may be identified by using hybridization and washing conditions of appropriate stringency. For example, hybridizations may be performed, according to the method of Sambrook et al., (supra) using a hybridization solution comprising: 5×SSC, 5× Denhardt's reagent, 0.5-1.0% SDS, 100 µg/ml denatured, fragmented salmon sperm DNA, 0.05% sodium pyrophosphate and up to 50% formamide. Hybridization is carried out at 37-42° C. for at least six hours. Following hybridization, filters are washed as follows: (1) 5 minutes at room temperature in 2×SSC and 0.5-1% SDS; (2) 15 minutes at room temperature in 2×SSC and 0.1% SDS; (3) 30 minutes-1 hour at 37° C. in 1×SSC and 1% SDS; (4) 2 hours at 42-65° C. in 1×SSC and 1% SDS, changing the solution every 30 minutes.

One common formula for calculating the stringency conditions required to achieve hybridization between nucleic acid molecules of a specified sequence homology is (Sambrook et al., 1989):

$$T_m=81.5° C.+16.6\text{Log }[Na+]+0.41(\% G+C)-0.63 (\% \text{ formamide})-600/\#\text{bp in duplex}$$

As an illustration of the above formula, using [Na+]=[0.368] and 50% formamide, with GC content of 42% and an average probe size of 200 bases, the $T_m$ is 57° C. The $T_m$ of a DNA duplex decreases by 1-1.5° C. with every 1% decrease in homology. Thus, targets with greater than about 75% sequence identity would be observed using a hybridization temperature of 42° C. Such a sequence would be considered substantially homologous to the nucleic acid sequence of the present invention.

The stringency of the hybridization and wash depend primarily on the salt concentration and temperature of the solutions. In general, to maximize the rate of annealing of the probe with its target, the hybridization is usually carried out at salt and temperature conditions that are 20-25° C. below the calculated $T_m$ of the hybrid. Wash conditions should be as stringent as possible for the degree of identity of the probe for the target. In general, wash conditions are selected to be approximately 12-20° C. below the $T_m$ of the hybrid. In regards to the nucleic acids of the current invention, a moderate stringency hybridization is defined as hybridization in 6×SSC, 5× Denhardt's solution, 0.5% SDS and 100 µg/ml denatured salmon sperm DNA at 42° C., and washed in 2×SSC and 0.5% SDS at 55° C. for 15 minutes. A high stringency hybridization is defined as hybridization in 6×SSC, 5× Denhardt's solution, 0.5% SDS and 100 µg/ml denatured salmon sperm DNA at 42° C., and washed in 1×SSC and 0.5% SDS at 65° C. for 15 minutes. A very high stringency hybridization is defined as hybridization in 6×SSC, 5× Denhardt's solution, 0.5% SDS and 100 µg/ml denatured salmon sperm DNA at 42° C., and washed in 0.1× SSC and 0.5% SDS at 65° C. for 15 minutes.

Nucleic acids for use in the present invention may be maintained as DNA in any convenient cloning vector. In a preferred embodiment, clones are maintained in a plasmid cloning/expression vector, such as pBluescript (Stratagene, La Jolla, Calif.), which is propagated in a suitable E. coli host cell. Genomic clones of the invention encoding the human or mouse GRP94 gene may be maintained in lambda phage FIX II (Stratagene).

GRP94-encoding nucleic acid molecules of the invention include cDNA, genomic DNA, RNA, and fragments thereof which may be single- or double-stranded. Thus, this invention provides oligonucleotides (sense or antisense strands of DNA or RNA) having sequences capable of hybridizing with at least one sequence of a nucleic acid molecule of the present invention, such as selected segments of the cDNA having SEQ ID NO: 1.

It will be appreciated by persons skilled in the art that variants (e.g., allelic variants) of these sequences exist in the human population, and must be taken into account when designing and/or utilizing oligos of the invention. Accordingly, it is within the scope of the present invention to encompass such variants, with respect to the GRP94 sequences disclosed herein or the oligos targeted to specific locations on the respective genes or RNA transcripts. With respect to the inclusion of such variants, the term "natural allelic variants" is used herein to refer to various specific nucleotide sequences and variants thereof that would occur in a human population.

Genetic polymorphisms giving rise to conservative or neutral amino acid substitutions in the encoded protein are examples of such variants. Additionally, the term "substantially complementary" refers to oligo sequences that may not be perfectly matched to a target sequence, but the mismatches do not materially affect the ability of the oligo to hybridize with its target sequence under the conditions described.

Thus, the coding sequence may be that shown in SEQ ID NO: 1, or it may be a mutant, variant, derivative or allele of this sequence. The sequence may differ from that shown by a change which is one or more of addition, insertion, deletion and subsitution of one or more nucleotides of the sequence shown. Changes to a nucleotide sequence may result in an amino acid change at the protein level, or not, as determined by the genetic code.

Thus, nucleic acid according to the present invention may include a sequence different from the sequence shown in SEQ ID NO: 1 yet encode a polypeptide with the same amino acid sequence.

On the other hand, the encoded polypeptide may comprise an amino acid sequence which differs by one or more amino acid residues from the amino acid sequence shown in SEQ ID NO: 2. Nucleic acid encoding a polypeptide which is an amino acid sequence mutant, variant, derivative or allele of the sequence shown in SEQ ID NO:2 is further provided by the present invention. Nucleic acid encoding such a polypeptide may show greater than 60% homology with the coding sequence shown in Sequence I.D. No. 1, greater than about 70% homology, greater than about 80% homology, greater than about 90% homology or greater than about 95% homology.

The present invention provides a method of obtaining nucleic acid of interest, the method including hybridization of a probe having part or all of the sequence shown in SEQ ID NO: 1 or a complementary sequence, to target nucleic acid. Hybridization is generally followed by identification of successful hybridization and isolation of nucleic acid which has hybridized to the probe, which may involve one or more steps of PCR.

Such oligonucleotide probes or primers, as well as the full-length sequence (and mutants, alleles, variants, and derivatives) are useful in screening a test sample containing nucleic acid for the presence of alleles, mutants or variants, especially those that have enhanced tumor antigen binding activity, the probes hybridizing with a target sequence from a sample obtained from the individual being tested. The conditions of the hybridization can be controlled to minimize non-specific binding, and preferably stringent to moderately stringent hybridization conditions are used. The skilled person is readily able to design such probes, label them and devise suitable conditions for hybridization reactions, assisted by textbooks such as Sambrook et al (1989) and Ausubel et al (1992).

In some preferred embodiments, oligonucleotides according to the present invention that are fragments of the sequences shown in SEQ ID NO: 1, or any allele associated with peptide binding activity, are at least about 10 nucleotides in length, more preferably at least 15 nucleotides in length, more preferably at least about 20 nucleotides in length. Such fragments themselves individually represent aspects of the present invention. Fragments and other oligonucleotides may be used as primers or probes as discussed but may also be generated (e.g. by PCR) in methods concerned with determining the presence in a test sample of a sequence encoding a GRP94 polypeptide.

B. Proteins

GRP94 protein is a molecular chaperone which resides in the endoplasmic reticulum and functions to help other secreted proteins or membrane receptors that form in the endoplasmic reticulum to attain their three-dimensional shapes. A full-length GRP94 protein of the present invention may be prepared in a variety of ways, according to known methods. The protein may be purified from appropriate sources, e.g., transformed bacterial or animal cultured cells or tissues, by immunoaffinity purification. However, this is not a preferred method due to the low amount of protein likely to be present in a given cell type at any time. The availability of nucleic acid molecules encoding GRP94 enables production of the protein using in vitro expression methods known in the art. For example, a cDNA or gene may be cloned into an appropriate in vitro transcription vector, such as pSP64 or pSP65 for in vitro transcription, followed by cell-free translation in a suitable cell-free translation system, such as wheat germ or rabbit reticulocyte lysates. In vitro transcription and translation systems are commercially available, e.g., from Promega Biotech, Madison, Wis. or BRL, Rockville, Md.

Alternatively, according to a preferred embodiment, larger quantities of GRP94 may be produced by expression in a suitable prokaryotic or eukaryotic system. For example, part or all of a DNA molecule, such as the cDNA having Sequence I.D. No. 1 or desired fragments thereof, may be inserted into a plasmid vector adapted for expression in a bacterial cell, such as E. coli. Such vectors comprise the regulatory elements necessary for expression of the DNA in the host cell (e.g. E. coli) positioned in such a manner as to permit expression of the DNA in the host cell. Such regulatory elements required for expression include promoter sequences, transcription initiation sequences and, optionally, enhancer sequences.

GRP94 produced by gene expression in a recombinant prokaryotic or eukaryotic system may be purified according to methods known in the art. In a preferred embodiment, a commercially available expression/secretion system can be used, whereby the recombinant protein is expressed and thereafter secreted from the host cell, to be easily purified from the surrounding medium. If expression/secretion vectors are not used, an alternative approach involves purifying the recombinant protein by affinity separation, such as by immunological interaction with antibodies that bind specifically to the recombinant protein or nickel columns for isolation of recombinant proteins tagged with 6-8 histidine residues at their N-terminus or C-terminus. Alternative tags may comprise the FLAG epitope or the hemagglutinin epitope. Such methods are commonly used by skilled practitioners.

The GRP94 proteins or peptide fragments of the invention, prepared by the aforementioned methods, may be analyzed according to standard procedures. For example, such proteins may be subjected to amino acid sequence analysis, according to known methods.

As discussed above, a convenient way of producing a polypeptide according to the present invention is to express nucleic acid encoding it, by use of the nucleic acid in an expression system. The use of expression systems has reached an advanced degree of sophistication today.

Accordingly, the present invention also encompasses a method of making a polypeptide (as disclosed), the method including expression from nucleic acid encoding the polypeptide (generally nucleic acid according to the invention). This may conveniently be achieved by growing a host cell in culture, containing such a vector, under appropriate conditions which cause or allow production of the polypeptide. Polypeptides may also be produced in in vitro systems, such as in a reticulocyte lysate.

Polypeptides which are amino acid sequence variants, alleles, derivatives or mutants are also provided by the present invention. A polypeptide which is a variant, allele, derivative, or mutant may have an amino acid sequence that differs from that given in SEQ ID NO: 2 by one or more of addition, substitution, deletion and insertion of one or more amino acids. Preferred such polypeptides have GRP94 function, that is to say have one or more of the following properties: peptide binding activity; binding activity towards ADP, ATP, or NECA; binding activity towards geldanamycin, or radicicol, or their synthetic variants, immunological cross-reactivity with an antibody reactive with the polypeptide for which the sequence is given in SEQ ID NO: 2. A polypeptide which is an amino acid sequence variant, allele, derivative or mutant of the amino acid sequence shown in SEQ ID NO: 2 may comprise an amino acid sequence which shares greater than about 35% sequence identity with the sequence shown, greater than about 40%, greater than about 50%, greater than about 60%, greater than about 70%, greater than about 80%, greater than about 90% or greater than about 95%. Particular amino acid sequence variants may differ from that shown in SEQ ID NO: 2 by insertion, addition, substitution or deletion of 1 amino acid, 2, 3, 4, 5-10, 10-20, 20-30, 30-40, 40-50, 50-100, 100-150, or more than 150 amino acids.

A polypeptide according to the present invention may be used in screening for molecules which affect or modulate its activity or function. Such molecules may be useful in a therapeutic (possibly including prophylactic) context.

II. Uses of GRP94-Encoding Nucleic Acids,

GRP94 Proteins and GRP94 Peptide Fragments

GRP94 appears to be an important immunomodulatory protein which plays a role in antigen presentation and tumor rejection. The GRP94 molecules of the invention may be used to advantage in methods to augment the immune response particularly for the treatment of cancer.

Additionally, GRP94 nucleic acids, proteins and antibodies thereto, according to this invention, may be used as a research tool to identify other proteins that are intimately involved in antigen repair, protein folding and tumor rejection reactions. Biochemical elucidation of these pathways will facilitate the development of novel reagents for the treatment of cancer and other immune function disorders.

A. GRP94-Encoding Nucleic Acids

GRP94-encoding nucleic acids may be used for a variety of purposes in accordance with the present invention. GRP94-encoding DNA, RNA, or fragments thereof may be used as probes to detect the presence of and/or expression of genes encoding GRP94 proteins. Methods in which GRP94-encoding nucleic acids may be utilized as probes for such assays include, but are not limited to: (1) in situ hybridization; (2) Southern hybridization (3) northern hybridization; and (4) assorted amplification reactions such as polymerase chain reactions (PCR).

The GRP94-encoding nucleic acids of the invention may also be utilized as probes to identify related genes from other animal species. As is well known in the art, hybridization stringencies may be adjusted to allow hybridization of nucleic acid probes with complementary sequences of varying degrees of homology. Thus, GRP94-encoding nucleic acids may be used to advantage to identify and characterize other genes of varying degrees of relation to GRP94, thereby enabling further characterization of the molecular chaperone system. Additionally, they may be used to identify genes encoding proteins that interact with GRP94 (e.g., by the "interaction trap" technique), which should further accelerate identification of the components involved in antigen presentation and tumor rejection.

Nucleic acid molecules, or fragments thereof, encoding GRP94 may also be utilized to control the production of GRP94, thereby regulating the amount of protein available to participate in immunomodulation reactions. Alterations in the physiological amount of GRP94 protein may dramatically affect the activity of other protein factors involved in antigen presentation, for example.

The availability of GRP94 encoding nucleic acids enables the production of strains of laboratory mice carrying part or all of the GRP94 gene or mutated sequences thereof. Such mice may provide an in vivo model for immunomodulation and tumor rejection. Alternatively, the GRP94 sequence information provided herein enables the production of knock-out mice in which the endogenous gene encoding GRP94 has been specifically inactivated. See Example 2. Methods of introducing transgenes in laboratory mice are known to those of skill in the art. Three common methods include: 1. integration of retroviral vectors encoding the foreign gene of interest into an early embryo; 2. injection of DNA into the pronucleus of a newly fertilized egg; and 3. the incorporation of genetically manipulated embryonic stem cells into an early embryo. Production of the transgenic mice described above will facilitate the molecular elucidation of the role GRP94 plays in embryonic development and immune regulation.

A transgenic mouse carrying the human GRP94 gene is generated by direct replacement of the mouse GRP94 gene with the human gene. These transgenic animals are useful for drug screening studies as animal models for human diseases and for eventual treatment of disorders or diseases associated with biological activities modulated by GRP94. A transgenic animal carrying a "knock out" of GRP94 is useful for assessing the role of GRP94 plays in embryonic development.

As a means to define the role that GRP94 plays in mammalian systems, mice may be generated that cannot make GRP94 protein because of a targeted mutational disruption of the GRP94 gene.

The term "animal" as used in this section includes all vertebrate animals, except humans. It also includes an individual animal in all stages of development, including embryonic and fetal stages. A "transgenic animal" is any animal containing one or more cells bearing genetic information altered or received, directly or indirectly, by deliberate genetic manipulation at the subcellular level, such as by targeted recombination or microinjection or infection with recombinant virus. The term "transgenic animal" is not meant to encompass classical cross-breeding or in vitro fertilization, but rather is meant to encompass animals in which one or more cells are altered by or receive a recombinant DNA molecule. This molecule may be specifically targeted to a defined genetic locus, be randomly integrated within a chromosome, or it may be extrachromosomally replicating DNA. The term "germ cell line transgenic animal" refers to a transgenic animal in which the genetic alteration or genetic information was introduced into a germ line cell, thereby conferring the ability to transfer the genetic information to offspring. If such offspring, in fact, possess some or all of that alteration or genetic information, then they, too, are transgenic animals.

The alteration or genetic information may be foreign to the species of animal to which the recipient belongs, or foreign only to the particular individual recipient, or may be genetic information already possessed by the recipient. In the last case, the altered or introduced gene may be expressed differently than the native gene.

The altered GRP94 gene generally should not fully encode the same GRP94 protein native to the host animal and its expression product should be altered to aminor or great degree, or absent altogether. However, it is conceivable that a more modestly modified GRP94 gene will fall within the compass of the present invention if it is a specific alteration.

The DNA used for altering a target gene may be obtained by a wide variety of techniques that include, but are not limited to, isolation from genomic sources, preparation of cDNAs from isolated mRNA templates, direct synthesis, or a combination thereof.

A type of target cell for transgene introduction is the embryonal stem cell (ES). ES cells may be obtained from pre-implantation embryos cultured in vitro (Evans et al., (1981) Nature 292:154-156; Bradley et al., (1984) Nature 309:255-258; Gossler et al., (1986) Proc. Natl. Acad. Sci. 83:9065-9069). Transgenes can be efficiently introduced into the ES cells by standard techniques such as DNA transfection or by retrovirus-mediated transduction. The resultant transformed ES cells can thereafter be combined with blastocysts from a non-human animal. The introduced ES cells thereafter colonize the embryo and contribute to the germ line of the resulting chimeric animal.

One approach to the problem of determining the contributions of individual genes and their expression products is to use isolated GRP94 genes to selectively inactivate the wild-type gene in totipotent ES cells (such as those described above) and then generate transgenic mice. The use of gene-targeted ES cells in the generation of gene-targeted transgenic mice was described, and is reviewed elsewhere (Frohman et al., (1989) Cell 56:145-147; Bradley et al., (1992) Bio/Technology 10:534-539).

Techniques are available to inactivate or alter any genetic region to a mutation desired by using targeted homologous recombination to insert specific changes into chromosomal alleles. However, in comparison with homologous extrachromosomal recombination, which occurs at a frequency approaching 100%, homologous plasmid-chromosome recombination was originally reported to only be detected at frequencies between $10^{-6}$ and $10^{-3}$. Non-homologous plasmid-chromosome interactions are more frequent occurring at levels $10^5$-fold to $10^2$-fold greater than comparable homologous insertion.

To overcome this low proportion of targeted recombination in murine ES cells, various strategies have been developed to detect or select rare homologous recombinants. One approach for detecting homologous alteration events uses the polymerase chain reaction (PCR) to screen pools of transformant cells for homologous insertion, followed by screening of individual clones. Alternatively, a positive genetic selection approach has been developed in which a marker gene is constructed which will only be active if homologous insertion occurs, allowing these recombinants to be selected directly. One of the most powerful approaches developed for selecting homologous recombinants is the positive-negative selection (PNS) method developed for genes for which no direct selection of the alteration exists. The PNS method is more efficient for targeting genes which are not expressed at high levels because the marker gene has its own promoter. Non-homologous recombinants are selected against by using the Herpes Simplex virus thymidine kinase (HSV-TK) gene and selecting against its nonhomologous insertion with effective herpes drugs such as gancyclovir (GANC) or (1-(2-deoxy-2-fluoro-B-D arabinofluranosyl)-5-iodouracil, (FIAU). By this counter selection, the number of homologous recombinants in the surviving transformants can be increased.

As used herein, a "targeted gene" or "knock-out" is a DNA sequence introduced into the germline or a non-human animal by way of human intervention, including but not limited to, the methods described herein. The targeted genes of the invention include DNA sequences which are designed to specifically alter cognate endogenous alleles.

Methods of use for the transgenic mice of the invention are also provided herein. Therapeutic agents for the treatment or prevention of cancer may be screened in studies using GRP94 transgenic mice.

In another embodiment of the invention, GRP94 knockout mice may be used to produce an array of monoclonal antibodies specific for GRP94 protein.

In yet another embodiment of the invention, the GRP94 gene has been replaced with a GRP94 gene that is flanked by short sequences that can be deleted (i.e.—cut out of) from the genome. Methods employing two different bacteriophage recombinases for the excision and integration of foreign DNA into the genome have been described. Several prokaryotic and lower eukaryotic site-specific recombination systems have been shown to operate successfully in higher eukaryotes. In yeast, plant and animal cells functional site-specific recombination systems have been described from bacteriophages P1 (CRE-loxP)(see below) and Mu (Gin-gix), and from the inversion plasmids of Saccharomyces cerevisiae (FLP-frt) (Morris et al. 1991; Lyznik et al. 1996) and Zygosaccharomyces rouxii (R-RS) (Onouchi et al. 1991; Onouchi et al. 1995). This approach can be employed in tissue-specific manner or in developmentally-specific manner, by methods known in the art. Such mice, in which GRP94 in inactivated in selected cells and not in others, are termed "conditional knockout mice" and serve as animal models for disease. For example, the finding that GRP94 is essential for muscle development, provides an important animal model for genetic deficiencies of muscle tissues and muscle degeneration diseases.

The availability of GRP94 deficient mice and GRP94 deficient ES cells enables the production of cell lines that can be used for developing therapeutics. First, the GRP94 deficient cell lines can be used to develop assays that distinguish the functions of GRP94 from the functions of the other three members of the mammalian HSP90family. The stress responses that rely predominantly on GRP94 should be affected in these cells and therefore discernible (as has already been shown in the data herein). Second, the GRP94 deficient cell lines can be used to develop drugs that are specific for either HSP90 or for GRP94, thus allowing creation of better anti-tumor drugs than those which target all members of the family, with fewer unwanted side effects. Third, the GRP94 deficient ES cell lines can be used to create differentiated cell lines in culture, for tissue-specific or cell type-specific applications. For example, the liver cells (hepatocytes) or fat cells (adipocytes) that have already been generated from such cells and can be used to determine the role of GRP94 in normal and/or pathological liver functions and/or in adipose tissue biology, using whole-genome and whole-proteome techniques such as DNA arrays and protein arrays. GRP94 is a known sensor for glucose metabolism, so cell types of interest will also include pancreatic cells and muscle cells, where the absence of GRP94 will enable the investigation and generation of drugs that either rely on GRP94's sensor functions or on its absence to affect the physiology of these tissues.

In the context of cancer therapy, the availability of GRP94 deficient mice and ES cells enables genetic testing of the model promoted by Srivastava et al. for tumor immunotherapy. Tumors can be generated that lack GRP94 and they can be injected into mice to determine the in vivo role of GRP94 in stimulating the immune system. The utility of such lab tests will be the discovery of other proteins, either stress proteins or others, that also have immuno-modulating activities, and whose action has so far been masked by the presence of GRP94.

B. GRP94 Protein and Fragments Thereof

Purified GRP94, or fragments thereof, may be used to produce polyclonal or monoclonal antibodies which also may serve as sensitive detection reagents for the presence and accumulation of GRP94 (or complexes containing GRP94) in mammalian cells. Recombinant techniques enable expression of fusion proteins containing part or all of the GRP94 protein. The full length protein or fragments of the protein may be used to advantage to generate an array of monoclonal antibodies specific for various epitopes of the protein, thereby providing even greater sensitivity for detection of the protein in cells.

Polyclonal or monoclonal antibodies immunologically specific for GRP94 may be used in a variety of assays designed to detect and quantitate the protein. Such assays include, but are not limited to: (1) flow cytometric analysis; (2) immunochemical localization of GRP94 in tumor cells; and (3) immunoblot analysis (e.g., dot blot, Western blot) of extracts from various cells. Additionally, as described above, anti-GRP94 can be used for purification of GRP94 (e.g., affinity column purification, immunoprecipitation).

From the foregoing discussion, it can be seen that GRP94-encoding nucleic acids, GRP94 expressing vectors, GRP94 proteins and anti-GRP94 antibodies of the invention can be used to detect GRP94 gene expression and alter GRP94 protein accumulation for purposes of assessing the genetic and protein interactions involved in protein folding, antigen presentation and tumor rejection. According to another aspect of the invention, methods of screening drugs for cancer therapy to identify suitable drugs for restoring or augmenting GRP94 product functions are provided. The GRP94 deficient cell lines described above provide superior screening tools for this purpose.

The GRP94 polypeptide or fragment employed in drug screening assays may either be free in solution, affixed to a solid support or within a cell. One method of drug screening utilizes eukaryotic or prokaryotic host cells which are stably transformed with recombinant polynucleotides expressing the polypeptide or fragment, preferably in competitive binding assays. Such cells, either in viable or fixed form, can be used for standard binding assays. One may determine, for example, formation of complexes between a GRP94 polypeptide or fragment and the agent being tested, or examine the degree to which the formation of a complex between a GRP94 polypeptide or fragment and a known ligand is interfered with by the agent being tested. Such assays, using the cell lines of the invention, facilitate the identification of agents which demonstrate differential binding between HSP90 and GRP94.

Another technique for drug screening provides high throughput screening for compounds having suitable binding affinity to the GRP94 polypeptides and is described in detail in Geysen, PCT published application WO 84/03564, published on Sep. 13, 1984. Briefly stated, large numbers of different, small peptide test compounds are synthesized on a solid substrate, such as plastic pins or some other surface. The peptide test compounds are reacted with GRP94 polypeptide and washed. Bound GRP94 polypeptide is then detected by methods well known in the art.

Purified GRP94 can be coated directly onto plates for use in the aforementioned drug screening techniques. However, non-neutralizing antibodies to the polypeptide can be used to capture antibodies to immobilize the GRP94 polypeptide on the solid phase. A preferred method of attaching GRP94 to plates or other solid matrices is the use of modified GRP94 that has a C-terminal tag which directs site-specific biotin addition. Specifically, the authors showed that a biotinylation site can be created at the C-terminus of N1-355, N34-355 and N34-222.

This invention also contemplates the use of competitive drug screening assays in which neutralizing antibodies capable of specifically binding the GRP94 polypeptide compete with a test compound for binding to the GRP94 polypeptide or fragments thereof. In this manner, the antibodies can be used to detect the presence of any peptide which shares one or more antigenic determinants of the GRP94 polypeptide.

A further technique for drug screening involves the use of host eukaryotic cell lines or cells (such as described above) which have a nonfunctional GRP94 gene. These host cell lines or cells are defective at the GRP94 polypeptide level. The host cell lines or cells are grown in the presence of drug compound. The rate of growth of the host cells is measured to determine if the compound is capable of regulating the growth of GRP94 defective cells.

For example, tumor cells are distinguished from normal cells by their uncontrolled proliferation. Many cancer treatment regimes are therefore designed to selectively inhibit rapidly dividing cells. The growth regulation of cells depends on many receptor proteins in the external cells membrane and on enzymes termed "kinases" enclosed within the cell membrane and whose function is to phosphorylate (add phosphate moieties) other growth-regulatory proteins. Many of the receptors and the kinases involved in cell growth regulation interact with heat shock protein 90 (HSP90), and depend on this interaction for their proper function and accurate deposition within the cell. Notably, HSP90 has been sought as a possible anti-tumor drug target. However, HSP90 is very homologous to GRP94, shares structural elements with GRP94 and binds most of the same ligands that bind to GRP94. To date, all inhibitors that are designed to interfere with HSP90 activity also bind to and inhibit GRP94. This leads to unwanted side effects as a consequence of using anti-HSP90 drugs. Accordingly, use of the GRP94 deficient cell lines will enable identification of agents which demonstrate selective binding of either GRP94 or HSP90.

A second strategy against cancer is aimed not at the growth differences between cancerous and normal cells, but at the chemical differences between them. Due to the exquisite ability of T lymphocytes to detect differences in protein fragments that are hallmarks of tumor cells, it should be possible to enlist the T cell arm of the immune system to act and kill such cells. GRP94 has been shown, initially by Srivastava et al, and later by others, to stimulate the recognition of tumor cells by such T lymphocytes.

A variation on this technique is the growth of cells with defective GRP94 under various stress conditions of interest, determining the ability of the cells to cope with the stress and measuring the ability of drugs to modulate the cellular stress response. An important extension of this technique to whole animals is the measurements of stress responses in mice in which the GRP94 gene had been inactivated in specific tissues and/or cell types.

The goal of rational drug design is to produce structural analogs of biologically active polypeptides of interest or of small molecules with which they interact (e.g., agonists, antagonists, inhibitors) in order to fashion drugs which are, for example, more active or stable forms of the polypeptide, or which, e.g., enhance or interfere with the function of a polypeptide in vivo. See, e.g., Hodgson, (1991) Bio/Technology 9:19-21. In one approach, one first determines the three-dimensional structure of a protein of interest (e.g., GRP94 polypeptide) or, for example, of the GRP94-peptide complex, by x-ray crystallography, by nuclear magnetic resonance, by computer modeling or most typically, by a combination of approaches. Less often, useful information regarding the structure of a polypeptide may be gained by modeling based on the structure of homologous proteins. An example of rational drug design is the development of HIV protease inhibitors (Erickson et al., (1990) Science 249:527-533). In addition, peptides (e.g., GRP94 polypeptide) may be analyzed by an alanine scan (Wells, 1991, Meth. Enzym. 202:390-411). In this technique, an amino acid residue is replaced by Ala, and its effect on the peptides activity is determined. Each of the amino acid residues of the peptide is analyzed in this manner to determine the important regions of the peptide.

The discovery of the peptide binding site of GRP94, and the high degree of homology of sequence and/or structure with other members of the HSP90 family of proteins, presents another aspect of the invention relating to peptides and similar ligands that bind to the homologous sites in the other members of the family. Targeting htpG, for example, in bacteria, may lead to novel antibiotics. Targeting the HSP90 peptide binding site, as another example, may lead to modulation of its activity. Third, the knowledge of one peptide binding site will lead to rational, structure-based genetic engineering of the binding sites of all other members of the HSP90 family of stress proteins.

It is also possible to isolate a target-specific antibody, selected by a functional assay, and then to solve its crystal structure. In principle, this approach yields a pharmacore upon which subsequent drug design can be based. It is possible to bypass protein crystallography altogether by generating anti-idiotypic antibodies (anti-ids) to a functional, pharmacologically active antibody. As a mirror image of a mirror image, the binding site of the anti-ids would be expected to be an analog of the original molecule. The anti-id could then be used to identify and isolate peptides from banks of chemically or biologically produced banks of peptides. Selected peptides would then act as the pharmacore.

Thus, one may design drugs which have, e.g., improved GRP94 polypeptide activity or stability or which act as inhibitors, agonists, antagonists, etc. of GRP94 polypeptide activity. By virtue of the availability of cloned GRP94 sequences, sufficient amounts of the GRP94 polypeptide may be made available to perform such analytical studies as x-ray crystallography. In addition, the knowledge of the GRP94 protein sequence provided herein will guide those employing computer modeling techniques in place of, or in addition to x-ray crystallography.

III Therapeutics

A. Pharmaceuticals and Peptide Therapies

The GRP94 polypeptides/proteins, antibodies, peptides and nucleic acids of the invention can be formulated in pharmaceutical compositions. These compositions may comprise, in addition to one of the above substances, a pharmaceutcally acceptable excipient, carrier, buffer, stabilizer or other materials well known to those skilled in the art. Such materials should be non-toxic and should not interfere with the efficacy of the active ingredient. The precise nature of the carrier or other material may depend on the route of administration, e.g. oral, intravenous, cutaneous or subcutaneous, nasal, intramuscular, intraperitoneal routes.

Whether it is a polypeptide, antibody, peptide, nucleic acid molecule, small molecule or other pharmaceutically useful compound according to the present invention that is to be given to an individual, administration is preferably in a "prophylactically effective amount" or a "therapeutically effective amount" (as the case may be, although prophylaxis may be considered therapy), this being sufficient to show benefit to the individual.

B. Methods of Gene Therapy

As a further alternative, the nucleic acid encoding the authentic biologically active GRP94 polypeptide could be used in a method of gene therapy, to treat a patient whose immune system requires modulation, or who is suffering from cancer, etc. In one approach, a modified version of GRP94 can be administered that is not susceptible to pan-HSP90 drugs, in this manner increasing the specificity of anti-HSP90 drugs and preventing the unwanted side effects due to simultaneous targeting of GRP94. In another approach, GRP94 may be used in gene therapy of diseases involving proteins that are not secreted efficiently and require GRP94 for efficient secretion, such as immunoglobulins, Toll-like receptors (Randow, F., and B. Seed. 2001. Endoplasmic reticulum chaperone gp96 is required for innate immunity but not cell viability. Nat Cell Biol 3:891), etc.

A major advantage of using a minimal and sufficient version of the GRP94 gene for gene therapy (and of a mini-protein for protein-based therapy) is that unwanted effects and activities of the administered gene/protein are minimized. GRP94, like all other HSP90s, has modular structure. It consists of distinct domains with unique activities. For example, at least 3 proteins are known to bind to the C-terminal domain of HSP90, and at least one binds to the middle domain (Young, J. C., I. Moarefi, and F. U. Hartl. 2001. *Hsp90: a specialized but essential protein-folding tool*. J Cell Biol 154:267; Buchner, J. 1999. *Hsp90 & Co.—a holding for folding*. Trends Biochem Sci 24:136). By limiting the therapy to a construct that consists of only the ligand binding domain and the charged domain of GRP94, there is no possibility for the other interactions to take place, making the introduced gene/protein a more specific therapy.

A second advantage of using a minimal-chaperone module is that a small protein is easier to produce in recombinant form. A small 355 amino acid protein is obtained in higher yields and in better activity (presumably due to higher percentage of protein molecules that fold correctly) than the full length GRP94, in either bacterial, insect cell or mammalian cell expression systems.

Vectors such as viral vectors have been used in the prior art to introduce genes into a wide variety of different target cells. Typically the vectors are exposed to the target cells so that transformation can take place in a sufficient proportion of the cells to provide a useful therapeutic or prophylactic effect from the expression of the desired polypeptide. The transfected nucleic acid may be permanently incorporated into the genome of each of the targeted tumor cells, providing long lasting effect, or alternatively the treatment may have to be repeated periodically.

A variety of vectors, both viral vectors and plasmid vectors are known in the art, see U.S. Pat. No. 5,252,479 and WO 93/07282. In particular, a number of viruses have been used as gene transfer vectors, including papovaviruses, such as SV40, vaccinia virus, herpes viruses including HSV and EBV, and retroviruses. Many gene therapy protocols in the prior art have employed disabled murine retroviruses.

Gene transfer techniques which selectively target the GRP94 nucleic acid to tumor tissues are preferred. Examples of this include receptor-mediated gene transfer, in which the nucleic acid is linked to a protein ligand via polylysine, with the ligand being specific for a receptor present on the surface of the target cells.

The following examples are provided to illustrate certain embodiments of the invention. They are not intended to limit the invention in any way.

EXAMPLE 1

Identification of the N-Terminal Peptide Binding Site of GRP94

Glucose Regulated Protein 94 (GRP94), also known as gp96, is a member of the HSP901 family of molecular chaperones and can dramatically stimulate T cell responses by two mechanisms: enhancement of peptide presentation to the adaptive arm of the immune system [1] and stimulation of innate immunity [2]. Because of these activities, tumor-derived GRP94 can be used to elicit immune response against the tumor and is potentially a powerful immunotherapeutic tool [3]. The antigen-presentation activity was shown not to be due to any mutation in GRP94 that would enhance its immunogenicity, but rather due to its ability to bind peptides [1, 4]. The GRP94-peptide complexes are known to be taken up by a subset of antigen presenting cells via receptor mediated endocytosis [5] and the chaperoned peptides are then represented on endogenous antigen presenting cells to MHC class I molecules on the cell surface. While peptide binding is a general activity of many molecular chaperones, it has been argued that GRP94 is among the most effective of such chaperones in enhancing antigen presentation. Despite its importance, the GRP94-peptide interaction and the identity of the peptide-binding site have not been characterized in detail. They are crucial issues towards understanding the immunostimulatory action of GRP94. The mode of peptide binding by GRP94 may also inform about its activity as a chaperone of selected membrane-bound and secreted proteins [6], though the connection between the two activities has yet to be elucidated. The same questions are also unanswered for all other HSP90 chaperones, despite the central role of these cytosolic chaperones in organizing signaling complexes and regulating transcription factors [7]. Several peptides derived from vesicular stomatitis virus (VSV) have been shown to bind GRP94. VSV8 is an octamer (RGYVYQGL) SEQ ID NO: 5) from the N protein of VSV and is the dominant T cell epitope of the virus, presented via MHC class I Kb to specific T cells [8]. The structure of a complex of this peptide with MHC class I has been solved [9]. VSV8 has been eluted from GRP94 purified from a VSV N protein-transfected cell line [10] and the peptide has been shown to bind directly to purified GRP94 in vitro [1]. Peptide A is a 15-mer KRQIYTDLEMNRLGK (SEQ ID NO: 6) from the glycoprotein of the virus and is not known to be immunogenic [1,11,12]. However, this peptide binds GRP94, as do other peptides, including LSSLFRPKRRPIYKS (SEQ ID NO: 27) from VSV G protein [1]. No common sequence motif is obvious from comparing these peptides. Spee and Neefjes used radioactive peptides with photo-reactive side chains to explore the peptide preferences of GRP94 [13]. No obvious size preference was found, and even 40mers could bind the chaperone. The only sequence specificity found was that 9mers with basic or acidic amino acids in positions 2 and 9 bind relatively weakly to GRP94. Thus, either sequences or the structural features that are compatible with binding to GRP94 are still not known.

The limited amount of information about GRP94's peptide binding activity is due in part to the low stoichiometry of binding (only about 1% of the protein had been shown to bind peptides [14]) and slow binding kinetics [15]. These technical obstacles also hindered the identification of structural determinants of the peptide binding site and its regulation. We showed that the N-terminal third of GRP94 constituted a peptide-binding entity and demonstrated that peptide binding to this fragment is specific, is inhibited by the pan-HSP90 inhibitors radicicol and geldanamycin, and has a binding stoichiometry close to 1 mole peptide per mole of GRP94 [15]. In addition, our data indicated that the peptide specificity of this site is different from that of another ER-resident stress protein, BiP [15]. In the present example we use molecular modeling, biochemical characterization and site-directed mutagenesis to identify a peptide binding site located within the N-terminal domain, on the face opposite the radicicol binding site, and show that His125 is located in the binding site and is directly involved in the binding activity.

The following materials and methods are provided to facilitate the practice of Example 1.

Recombinant Proteins

N1-355: The construct for expression of N1-355 in insect cells and the purification procedure are described in [15]. Recombinant N1-355 contained an N-terminal His6 tag, followed by the first 355 amino acids of a mature sequence of GRP94 and a C-terminal ER1 targeting signal KDEL.

N34-355: The sequence coding for the first 33 amino acids of N1-355 was deleted by PCR cloning. The resultant PCR product was inserted into the pQEXa vector (Qiagen) using BamH1 and XmaI so as to add a His6 tag followed by a factor Xa recognition sequence at amino terminus. The plasmid was transformed into M15 *E. coli*, which were allowed to grow to midlog phase and then incubated with 1 mM IPTG for 4 hrs at 27° C. to induce protein expression. Bacteria were harvested and lysed in 1% NP40 (Sigma Chemicals) in 20 mM phosphate buffer pH 7.2, containing 500 mM NaCl and 20 mM imidazole. N34-355 was purified from the detergent lysates by affinity chromatography on Ni-NTA columns (Qiagen), according to the manufacturer's instructions. Bound proteins were eluted with 500 mM imidazole, dialysed and concentrated. The protein was stored in 25 mM HEPES (pH 7.2), 110 mM KOAc, 20 mM NaCl, 1 mM Mg(OAc)2, 0.1 mM CaCl2 (buffer A) containing 10-20% sucrose at −80° C. When needed, the amino terminal extension containing the His6 tag was removed by digestion with factor Xa (Novagen) according to the manufacturer instructions. The reaction mixture was re-purified over a small Ni-NTA column and the flow through containing only the cleaved N34-355 was used. The cleaved protein appeared 2-3 kDa smaller on SDS-PAGE compared to the parent protein, consistent with the removal of 17 amino acids (not shown). After digestion, the heptamer PYNGTGS (SEQ ID NO: 7) precedes Ala34 or the mature N34-355 sequence.

Constructs for mini-GRP94 (e.g., amino acids 34-355, 70-221) and/or for mini-HSP90 recombinant proteins were created by PCR amplification of the desired sequences and cloning into the multiple cloning site of the expression vector pQE30 (Qiagen Corp.), by standard procedures. A hexa-histidine site is provided by this vector at the N-terminus of the expressed protein, to enable affinity purification.

The HSP90 fragment consisting of amino acids 1-210 will be used, expressed as described for GRP94. In preference to using the normal HSP90 sequence, we will mutate the region between amino acids 100-134 (see FIG. 4 of example 1). Site directed mutagenesis will be guided by the amino acids in GRP94 that contact the bound peptides, and will include, but will not be limited to, Thr90, Ile81, Pro82 and insertion of residues before amino acid 130, to match the GRP94 sequence.

Mutant proteins: Amino acids substitutions were introduced into the vector encoding N34-355 with the QuikChange kit (Stratagene). Mutations were verified by sequencing and, when appropriate by restriction enzyme analyses. The proteins were expressed in bacteria and purified as described above.

Peptides

Peptides were synthesized at the University of Chicago facility and verified by mass spectroscopy. The sequences of the two binder peptides are: VSV8, RGYVYQGL, (SEQ ID NO: 5) from the VSVN protein; Pep A, KRQIYTDLEMNR-LGK, (SEQ ID NO: 6) from the VSV G protein. Stock solutions were prepared in water and stored at −80° C. Peptide concentrations were determined by a BCA assay (Pierce). Where indicated, peptides were iodinated by the IodoBead method (Pierce) and unincorporated iodine was removed by passage over a short Dowex AG1X8 column. The specific radioactivity of the peptides was routinely 2×1014-1×1015 cpm/mole.

Peptide Binding Assays

Two types of binding assays were used. The solution binding assay was performed as described in [15]. Briefly, recombinant proteins were incubated with iodinated peptide under saturating conditions and radioactivity associated with protein-peptide complexes was measured after separation of free peptide over spin columns containing 0.8 μl of packed P-30 beads (Bio Rad) in buffer A. Iodinated peptide without protein was used as background control for spin column separation.

A solid phase binding assay (referred to as plate assay in the text) is described and validated elsewhere (Biswas et al., manuscript in preparation). Briefly, 96-well plates (Costar 3590 High Binding, Corning, N.Y.) were coated with peptides prior to assay and the recombinant proteins in 100 μl of buffer A were allowed to bind for 90 min. Binding was quantified by HRP-rabbit anti-His$_6$ (Amersham) and color development was monitored at 415 nm with a BioTek plate reader. Since both N1-355 and N34-355 normally reached saturation at the input level of 0.7 or 1 μg, the OD415 value at this level was defined as 1 and all data points were normalized to it. Inhibition by 300 μM radicicol (Sigma; stock solution in DMSO) was used as a specificity control.

Since peptide binding to GRP94 is saturable and specific, yet the off rate is exceedingly slow [15], Ka values were estimated graphically from the fractional occupancy curves (OD415 value at a given protein input relative to OD415 value at saturation as a function of protein input). When the binding reaction is not in equilibrium, these values are valid as comparative parameters among the various mutants.

Gel Electrophoresis

Analysis of protein conformation by blue native gel electrophoresis was accomplished by using 5-15% gradient acrylamide gels in the Laemli gel system without SDS [40], with Coomassie brilliant blue G 250 (Sigma Chemicals) included in the cathode buffer. Thyroglobulin, ferritin and BSA were used as molecular weight standards.

Protein Modifications

Binding of the fluorescent dye 8-ANS (Molecular Probes, Eugene, Oreg.) to proteins was performed by incubating 5 μM ANS with 0.5 μM of the appropriate N355 construct in 500 μl of buffer A.

For acrylodan (6-acryloyl-2-dimethylaminonaphthalene) modification, recombinant protein (10 μM) was incubated at 40° C. overnight in the presence of 100 μM acrylodan (Molecular Probes) in 50 mM ammonium acetate buffer, pH 6.9, and free acrylodan was removed using a spin column. For the experiments measuring the effect of peptide on N355-acrylodan, peptide was added to the final concentration of 100 μM; equivalent volume of buffer was added to control samples. The mixtures were heat-shocked at 50° C. for 10 min, diluted to 500 μl and fluorescence measurements were performed on PTI fluorimeter. Samples were excited at 350 nm for ANS and 390 nm for acrylodan and the emission spectra collected between 400 and 600 nm. The slit widths were set at 2 nm for excitation and 2-6 nm for emission.

Before modification of histidines with DEPC, wild type or H125D N34-355 (800 μg each) were treated with 24 units Factor Xa (Novagen) in buffer A overnight at 25° C., and then repurified using Xarex Agarose (Novagen) to remove factor Xa and Ni-NTA Agarose to remove the His6 containing peptide. The His-cleaved proteins were reacted with peptide A (or solvent alone) at 12 μM protein and 2.8 mM peptide in buffer A overnight at 25° C. Free peptide was removed and the buffer exchanged to 50 mM ammonium acetate, pH 6.8, using P10 spin columns. Both free N34-355 and the protein-peptide complexes were reacted with 1 mM DEPC (Sigma Chemicals) at 25° C. or with EtOH as a solvent control. Incubation for 15-20 min gave complete His modification, as determined by monitoring the reaction at 240 nm [25]. Where indicated, the carbethoxyhistidine was reverted back to histidine by treatment with 400 mM hydroxylamine for 15 min at 25° C. [26].

Mass Spectrometry

Samples were diluted to 20 μM final concentration in sinapinic acid saturated with acetonitrile and 1% TFA. 1-2 μl of each sample was adsorbed onto a Ciphergen gold chip and allowed to air dry. Masses were measured by the SELDI-TOF ProteinChip Reader (Ciphergen).

RESULTS

GRP94-Bound Peptide is Contained Within a 188-residues Fragment

Figure 1B:
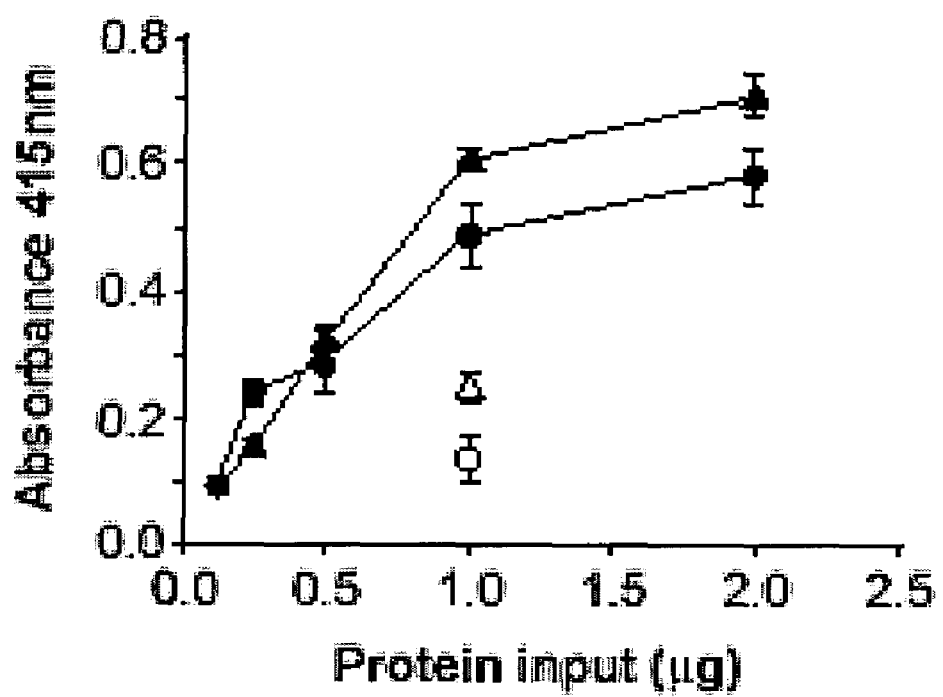
FIG. 1B. Peptide binding ability of N1-355 and N34-355. The two versions of recombinant chaperone were tested, at the doses indicated, for binding of the 8-mer peptide VSV8 in the 96-well plate assay (see Experimental Procedures). Filled triangles, N1-355; filled squares, N34-355; empty symbols show inhibition of peptide binding by radicicol.
Figure 1C:
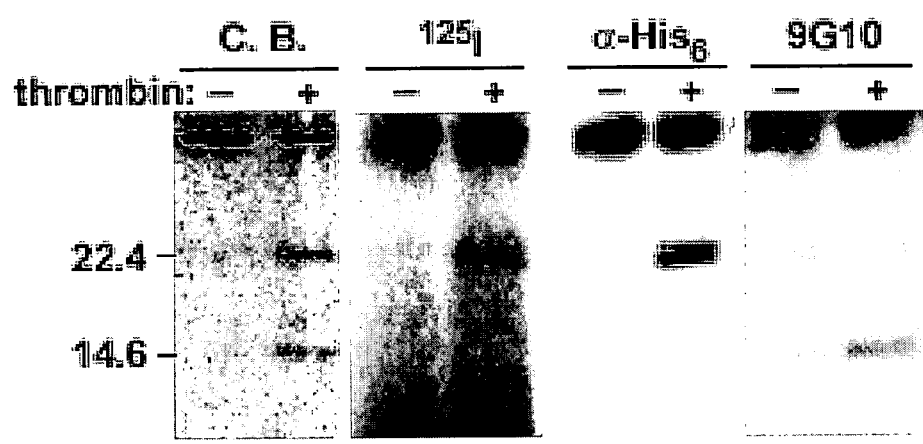
FIG. 1C. Thrombin digestion of N1-355—iodinated peptide complex. C. B., Coomassie blue stained gel after partial proteolysis with thrombin, showing the cleavage of the recombinant protein into two fragments. $^{125}$I, autoradiography of the same gel, showing that the iodinated peptide co-migrates with the larger thrombin fragment. α-His, western blot for the N-terminal His tag identifying the 22.4 kDa band as the N-terminal fragment. 9G10, western blot for the epitope residing in the acidic domain identifying the 14.6 kDa band as the C-terminal fragment. The larger band at the top of the gels is undigested material.

Previously we demonstrated that a truncated version of GRP94, containing amino acids 1-355 is sufficient to account for the ability of the full-length protein to bind immunologically relevant peptides, such as the VSV major T cell antigen, VSV8. We also showed that this activity was subject to regulation by the pan-HSP90 inhibitors radicicol and geldanamycin [15]. To further locate this peptide-binding site, a shorter version of recombinant GRP94 that lacked the first 33 amino acids of the mature protein (N34-355; FIG. 1A) was cloned and overexpressed in *E. coli*. This recombinant protein bound VSV8 with a binding curve very similar to that of N1-355 (FIG. 1B), showing that the first 33 amino acids are not essential for the peptide binding activity. To define an even smaller fragment containing the peptide-binding site, we took advantage of the single thrombin site in N34-355, C-terminal to Arg222, and asked whether a complex of N34-355 and peptide remains intact after cleavage with thrombin. Following the digestion, two bands were detectable by Coomassie blue staining corresponding to the predicted N-terminal 22.4 kDa and C-terminal 14.6 kDa fragments (FIG. 1C). The assignment of the fragments was confirmed by antibodies specific to either the N-terminus of N34-355 (anti-His$_6$) or to residues 261-276 near the C-terminus (9G10 [16]). Because the GRP94-peptide complex is resistant to SDS [1], peptide-bound protein fragments can be detected after SDS-PAGE by the radioactivity of the bound iodinated peptide. In the absence of thrombin, a radioactive band corresponding to the uncleaved complex was detectable. After partial thrombin digestion, an additional radiolabeled band of apparent molecular weight of 22.4 kDa is detected after SDS-PAGE separation, whilst the other 14.6 kDa fragment is not labeled (FIG. 1C). These data suggest, therefore, that amino acids 34-222 of GRP94 are sufficient to retain the bound peptide.

Molecular Modeling of the GRP94-peptide Complex

We next took advantage of previously published data [17] [18] to create a computer model of potential peptide-binding sites. First, we used the crystal structure of the N-terminal domain of HSP90 (PDB files 1YER and 1A4H) to generate an energy minimized, predicted structure of the highly homologous segment of GRP94 (51% identity between yeast HSP82 and mouse GRP94). Second, we used the known structure of the antigenic peptide VSV8, which was determined in association with MHC class I (2 MHC; [9]). Third, making the simplifying assumption that the conformation of VSV8, when bound to GRP94, is essentially similar to its conformation when bound to MHC class I, we used the docking algorithm PatchDock [19] to predict potential binding sites. The algorithm searches the protein surface for locations with highest geometric shape complementarity to the ligand molecule and docks the ligand into these locations. Such docking solutions usually produce clusters in different protein cavities, since binding in cavities enables greater shape complementarity. In addition, statistical data about atomic contacts of VSV8 with MHC class I was collected and used to score the docking solutions. The highest scoring solutions in terms of shape complementarity and statistical score were selected.

The Peptide-binding Site is Distinct from the Radicicol-binding Pocket

Figure 2A:
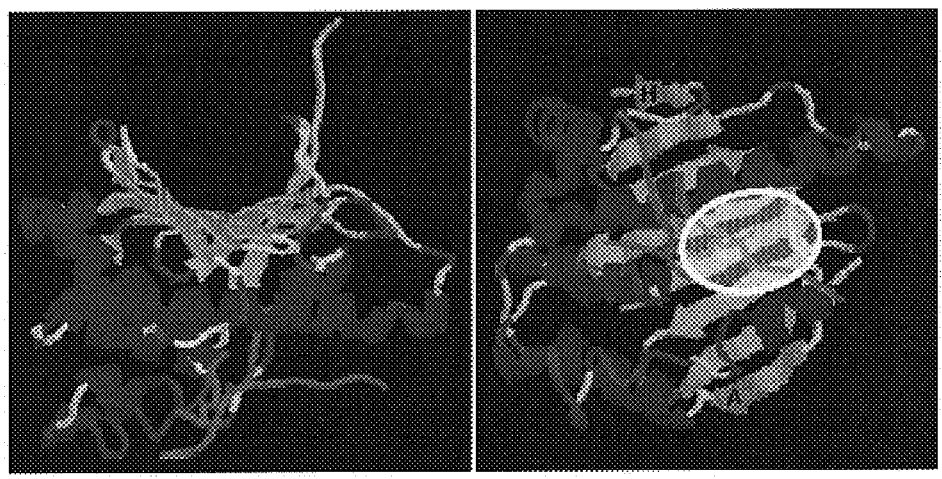
FIG. 2A. Three peptide docking solutions partially overlap with the radicicol/geldanamycin binding site. Left panel, side view from the C-terminal end along the axis of the β sheet. Right panel, bottom view. White oval, outline of the radicicol-binding site.
Figure 3A:
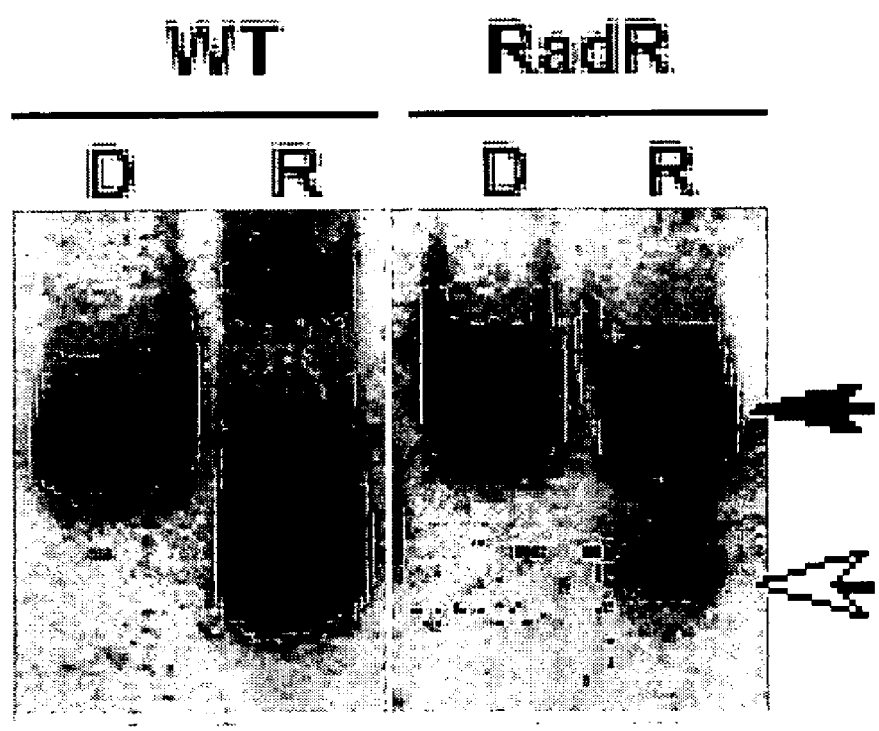
FIG. 3A. D128N, G132A mutant of N34-355 (RadR) is refractive to radicicol treatment N34-355 (WT) and RadR proteins were incubated for 15 min with either DMSO or radicicol and resolved on a blue native gel. Radicicol-bound WT protein migrates through the gel more rapidly, due to a conformational change in the protein [15]. The ability of the RadR protein to bind radicicol is dramatically reduced. Black arrow, unmodified protein; white arrow, radicicol bound protein.
Figure 3B:
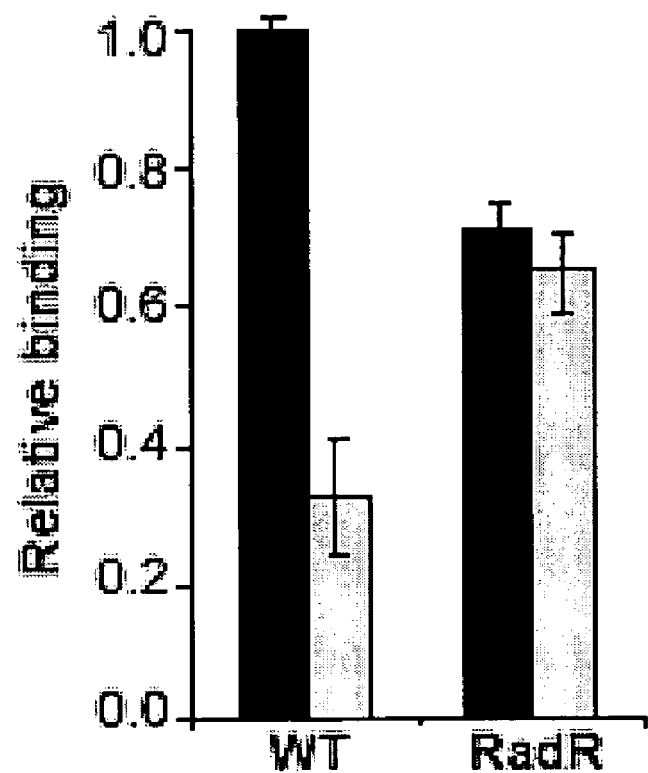
FIG. 3B. Peptide binding by RadR mutant is not affected by radicicol and is similar at saturation to that of WT protein. Binding of N34-355 and RadR proteins to VSV8 peptide was measured by the plate assay (see Experimental Procedures). Black bars, binding in the absence of inhibitor; grey bars, binding in the presence of radicicol. Data are averages of triplicate samples.
Figure 3C:
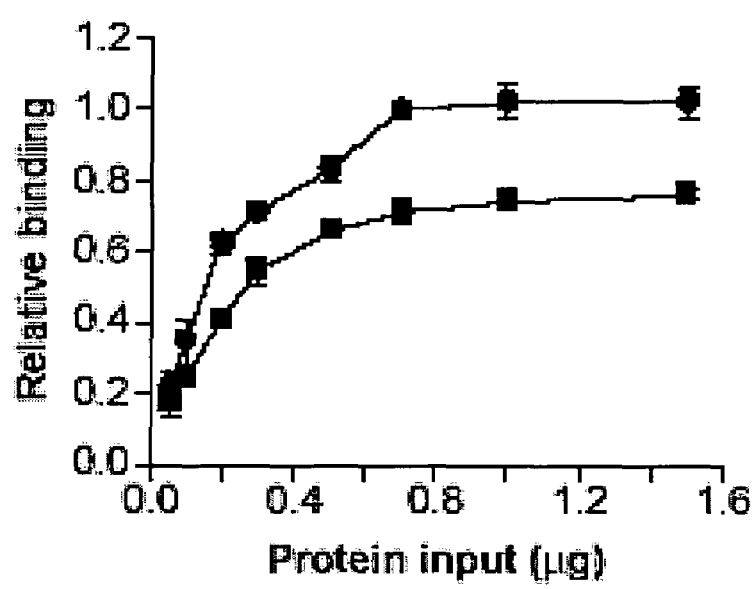
FIG. 3C. Dose binding of N34-355 and RadR proteins. Binding to VSV8 peptide was measured in a plate assay. Circles, WT protein; squares, RadR mutant. Data are averages of triplicate samples.

The seven best solutions mapped to two potential docking sites. One site overlaps with the radicicol-binding pocket (FIG. 2A), the largest cavity in the protein. This site was considered unlikely, because previous data showed that radicicol and peptide can bind simultaneously [15]. We therefore asked whether mutants that did not bind radicicol could still bind peptides. Relying on the solved structure of the complex between yeast HSP90 N-terminal domain and radicicol [18] and on the similarity between HSP90 and GRP94 [19], we mutated residues Asp128 and Gly132 simultaneously, to Asn and Ala, respectively. Asp93 in HSP90 (corresponding to Asp128 in GRP94) makes a crucial hydrogen bond with radicicol, and Gly97 packs tightly against the inhibitor and also serves to position helix 4, an important portion of the binding pocket [17, 18, 20]. The D93N mutant of HSP90 does not bind ATP [21], so the double mutant of GRP94 was expected to be unable to bind radicicol. Recombinant N34-355 D128N,G132A mutant (RadR) was soluble, mostly monomeric and expressed the conformational-sensitive epitope for the antibody 9G10, like the wild type protein. To test whether the RadR mutant binds radicicol, we used two functional tests (see [15] for details): loss of the 9G10 epitope and acquisition of a compact conformation with increased mobility in native blue gels. Both changes have been shown to reflect the conformational change in the protein upon radicicol binding [15]. The resultant mutant was refractive to treatment with radicicol, as judged by the continued exposure of the 9G10 epitope (data not shown) and lack of acquisition of a compact conformation (FIG. 3A). Despite lack of radicicol binding, the RadR protein bound peptide effectively (FIG. 3C), with only a small reduction in the apparent association constant compared to the WT protein. Consistent with lack of radicicol binding, the peptide binding activity of RadR mutant was not inhibited by pre-treatment with radicicol, whereas the activity of wild type N34-355 was inhibited significantly (FIG. 3B). We conclude that not only is the peptide-binding site within N34-355 distinct from the radicicol-binding site [15], but abolition of inhibitor binding does not affect the ability to bind peptides.

Peptide Binding Affects the Environment of the Binding Site for Two Hydrophobic Probes.

Figure 2B:
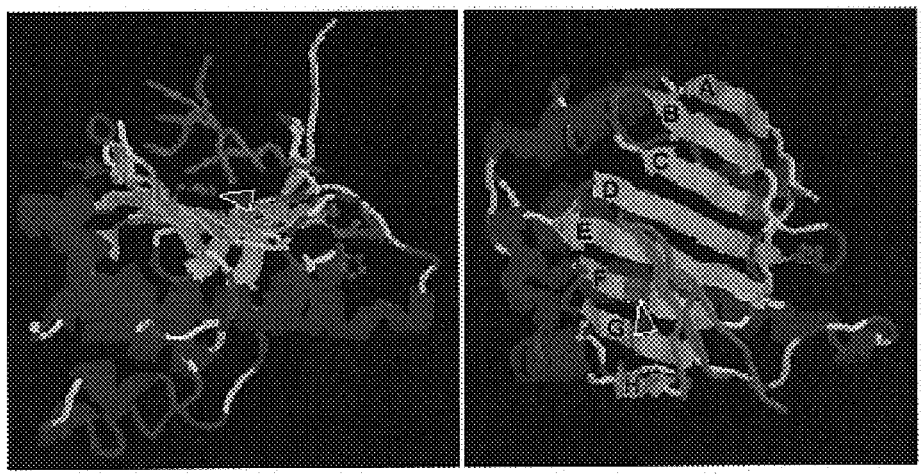
FIG. 2B. Four docking solutions map over part of the β sheet. Left panel, view along the axis of the β sheet, same as in A. Right panel, top view. The sole cysteine and three histidines are shown in ball-and-stick representation, in yellow and light blue, respectively. Red arrow, Cys117; red arrowhead, His125; A-H, strands of the β sheet.

The other potential peptide docking site is on the opposite side of the β sheet, where there is a large saddle-like surface made of 8 β strands. Side barriers to this saddle are provided by two loops—Asp170-Arg222 and Lys119-Asn122, plus part of a strand H (Val260-Ser263) that is the end of the modeled sequence (FIG. 2B). Four of the highest scoring solutions predicted that VSV8 could fit well within this saddle (FIG. 2B). The peptides would fit at an angle of approximately 70 degrees relative to the long axis of the β sheet across strands E-H, and most of the surface contact would be with the β sheet.

Figure 4A:
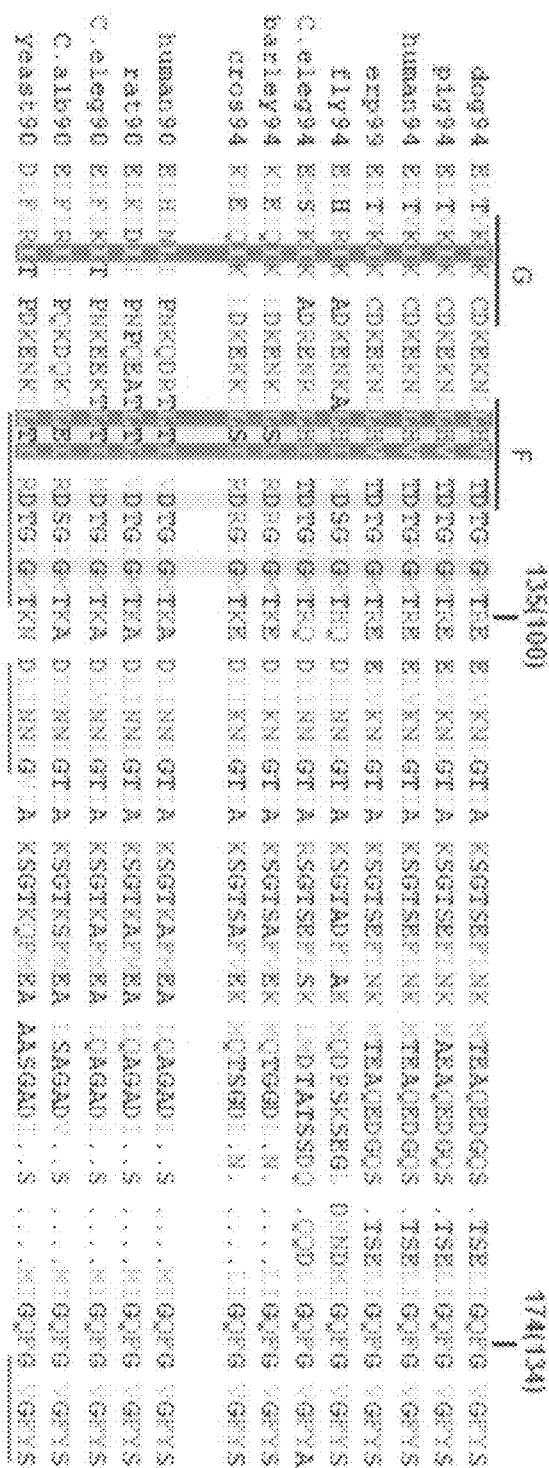
FIG. 4A. Multiple sequence alignment of parts of the N-terminal domains of GRP94 and HSP9O. (SEQ ID NO: 14), (SEQ ID NO: 15), (SEQ ID NO: 16), (SEQ ID NO: 17), (SEQ ID NO: 18), (SEQ ID NO: 19), (SEQ ID NO: 20), (SEQ ID NO: 21), (SEQ ID NO: 22), (SEQ ID NO: 23), (SEQ ID NO: 24), (SEQ ID NO: 25), (SEQ ID NO: 26) Black lines above the sequence, strands G and F (see panel B), containing Cys117 and His125, respectively. Red lines below the sequence, inhibitor-binding pocket constituents [17, 20] within the partial sequence. Green line, 35 amino acids in HSP90 whose position is different between the geldanamycin-bound and free conformations. These are HSP90 residues 100-134 (numbers in parentheses), corresponding to residues 135-174 in GRP94. Yellow highlight, position 125; grey highlights, Asp128 and Gly132, residues mutated in the RadR mutant; green highlights, Ile115, Leu124 and Val126, residues contributing to the hydrophobic pocket. Other residues from the hydrophobic pocket are Leu80, Ile84, Leu240, Ile243, Val247, Ile254, Ile258, Pro259 and Val260. Amino acids are colored blue for E or D, red for K, R or H, purple for N or Q, green for F or Y, brown for C, black for A, G, P, S, T, and yellow for I, L, M, V.
Figure 4B:
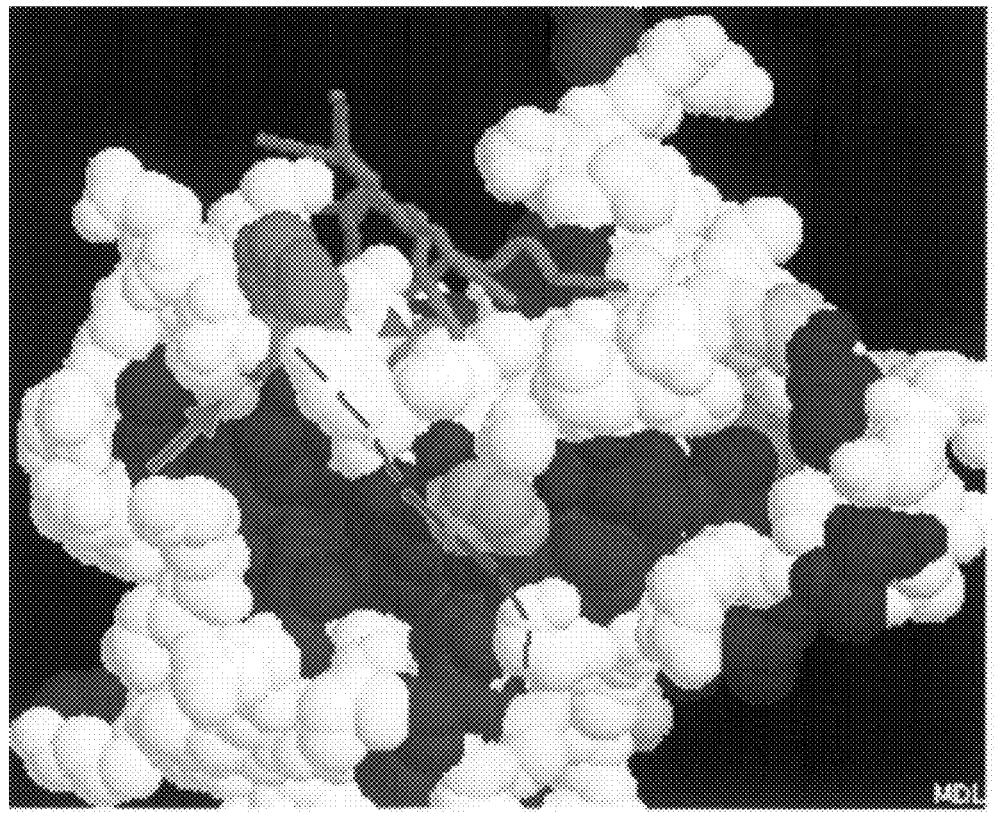
FIG. 4B. Model of the hydrophobic pocket. A spacefill model showing the protein in the same view as in FIG. 2B, left panel. Peptides are shown in light green. Dark green residues, I, L and V; blue, F; purple, T; brown, P; yellow, C; light blue, H. Red arrow, Cys117, red arrowhead, His125. Red dashed line, approximate location of the residues shown to crosslink to bis-ANS [22].
Figure 5A:
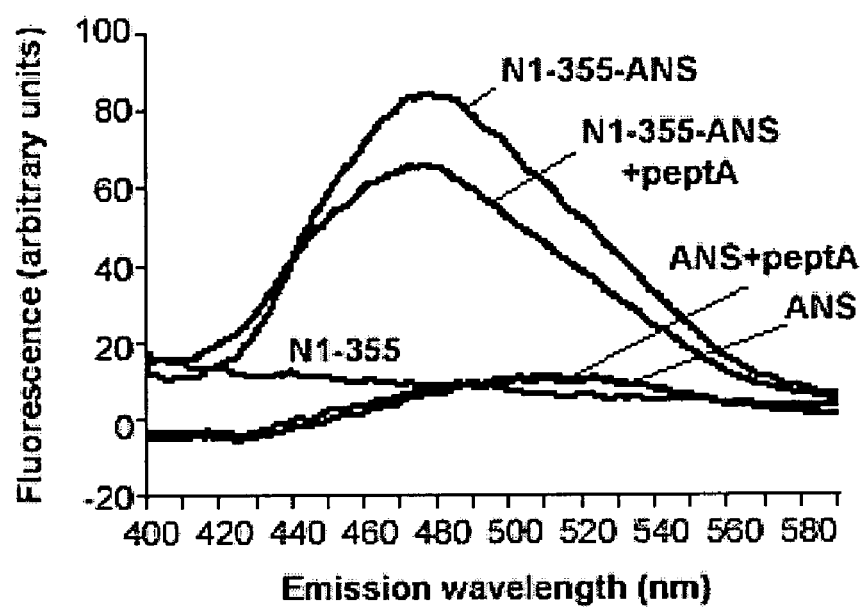
FIG. 5A. Peptide A binding affects the emission of N1-355-bound ANS. N1-355 was first reacted with ANS(N-1-355-ANS) and then bound to saturating amount of peptide A (N-1-355-ANS+peptA). Emission maximum of N1-355-ANS is 478 nm, indicating a highly hydrophobic environment. Addition of peptide A partially quenches the fluorescence of N1-355-ANS, but not that of free ANS. N1-355 itself does not fluoresce in the wavelength range shown.

This putative peptide-binding site is in close proximity to a deep hydrophobic pocket (FIG. 4). Hydrophobic residues from strands E, F, G and H, as well as from the helix and loop leading to the strand H and the long helix are predicted to form this pocket. The edge strand (H) of the β sheet and preceding loop, which form a part of an entrance to this pocket (FIG. 4B), have been shown to contribute to the binding site of the hydrophobic dye bis-ANS [22]. We therefore speculated that this pocket can accommodate various hydrophobic probes, such as bis-ANS, ANS, acrylodan and Nile Red, which have been reported to bind to GRP94 [12,22]. The emission spectrum of ANS-labeled N1-355 had a maximum around 474 nm (FIG. 5A), as expected if ANS was indeed bound in a hydrophobic environment [23]. When ANS-labeled N1-355 was incubated with peptide A, the intensity of ANS fluorescence decreased and its emission maximum was blue shifted slightly (FIG. 5A). Such decreased ANS fluorescence is consistent with peptide A binding affecting, either directly, or via conformational changes, the environment of the fluorophore. Alternatively, if ANS and peptide compete for the same binding site, it may be due to the release of ANS. The latter explanation can be ruled out due to blue shift of ANS emission, so we favor the notion that peptide binds in proximity to the hydrophobic pocket.

Figure 5B:
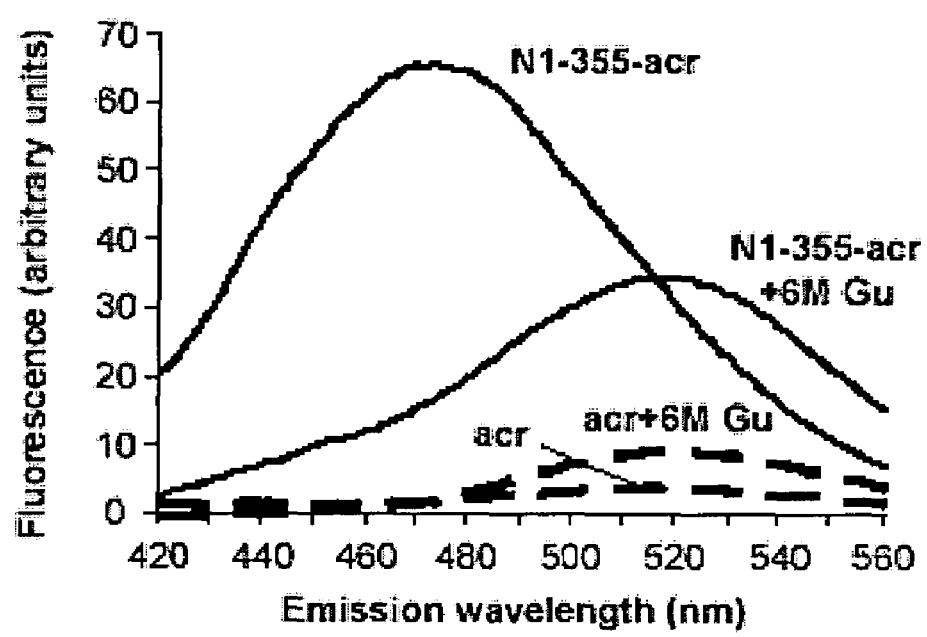
FIG. 5B. Acrylodan binds covalently to the Cys within the predicted hydrophobic pocket. N1-355 and N34-355 were reacted with acrylodan overnight at 40° C. A sample with identical amount of acrylodan without protein served as a control. Half of each sample was then supplemented with guanidine chloride to a final concentration of 6M and another with equivalent volume of buffer. The emission maximum of N1-355-bound acrylodan under nondenaturing conditions was around 473 nm, indicating highly hydrophobic environment. In 6M guanidine chloride, the emission maxima were around 522 nm for both N1-355-bound and free acrylodan, while the fluorescence intensity of the protein-bound acrylodan was significantly higher than that of the free dye, indicating covalent linkage.

If peptide in fact binds as predicted, it should also affect the environment of other hydrophobic probes. Strand G has the sole cysteine residue (Cys 17) in N1-355, whose sidechain points into the hydrophobic pocket (FIG. 4), so we modified the protein with the Cys-specific naphthalene derivative acrylodan [12]. While acrylodan has a very low quantum yield in aqueous solutions, its fluorescence is markedly increased upon reaction with thiols [24], and then the fluorescence is highly sensitive to the hydrophobicity of its environment. As shown in FIG. 5B, when excited at 390 nm, acrylodan-modified N1-355 had emission maximum around 474 nm, as expected if the fluorophore was in a highly hydrophobic environment. Free acrylodan had a maximum at about 520 nm. Denaturation of the N1-355-acrylodan conjugate with 6M guanidine hydrochloride abolished the fluorescence at 474 nm and gave rise to the same emission maximum as free acrylodan in 6M guanidine, indicating that the observed fluorescence is dependent on the tertiary structure of the protein. As expected for the covalent modification, the fluorescence intensity of the denatured N1-355-acrylodan conjugate was significantly higher than that of free acrylodan (FIG. 5B). These spectral properties fulfill the expectation that acrylodan is located in a hydrophobic pocket when bound covalently to Cys117. Therefore, acrylodan modification of N1-355 provides a defined fluorescence probe for detection of molecular changes.

Figure 5C:
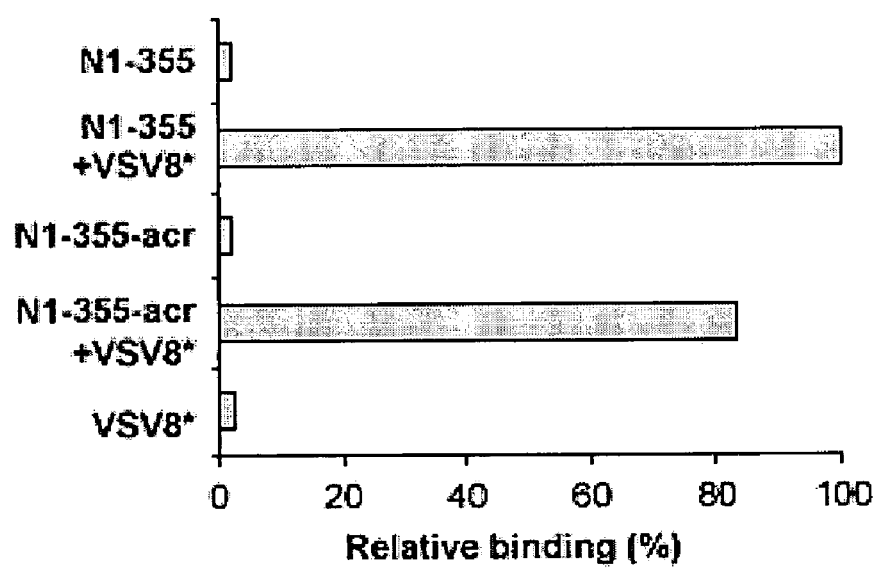
FIG. 5C. Acrylodan conjugated N1-355 binds peptide to the same extent as unconjugated N1-355. Free or acrylodan-conjugated protein (3.6 μM) was reacted with 800 mM $^{125}$I-VSV8 under saturating conditions and unbound peptide was removed using a spin column [15]. Free $^{125}$IVSV8 was used to control for the efficiency of removal of the unbound peptide. N1-355 and N1-355-acr, free and acrylodan-conjugated protein respectively; N1-355+VSV8* and N1-355-acr+VSV8*, same proteins bound to $^{125}$I-VSV8; VSV8*, free $^{125}$I-VSV8 peptide.
Figure 5D:
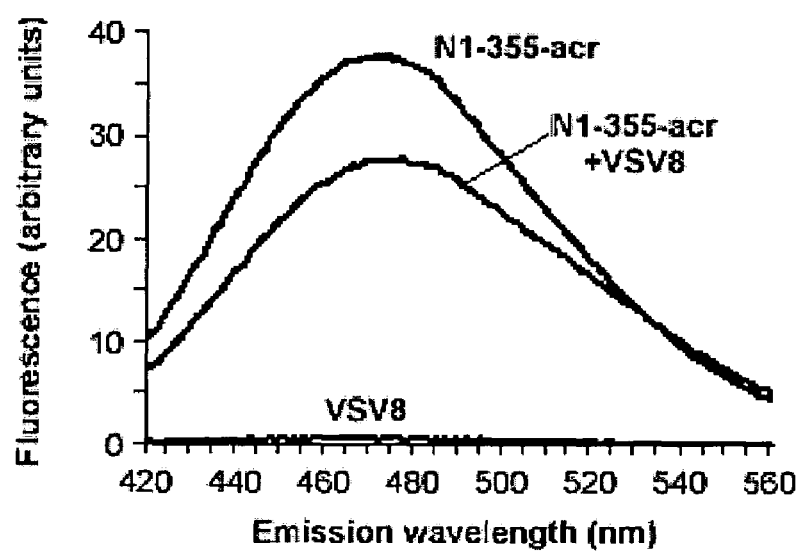
FIG. 5D. Fluorescence of acrylodan covalently bound to N1-355 is affected by the addition of peptide. Fluorescence emission scans of acrylodan-conjugated N1-355 in the presence of either VSV8 (800 mM final concentration) or equivalent volume of buffer were taken at excitation wavelength 390 nm. VSV8 alone had no fluorescence in the measured wavelength range.

To test whether modification with acrylodan affects peptide binding by N1-355, we incubated acrylodan-modified and unmodified proteins with saturating amount of iodinated VSV8 and measured peptide binding to each. Acrylodan-conjugated protein was capable of binding peptide essentially like the unmodified protein (FIG. 5C), showing that acrylodan does not interfere with the binding activity. Importantly, the fluorescence of acrylodan was partly quenched in the presence of peptide (FIG. 5D). These data are in good agreement with the model in FIG. 2B, which predicts that the peptide-binding site is distinct from but in close proximity to the hydrophobic pocket. These data cannot, however, distinguish quenching due to peptide binding in close proximity to the acrylodan from that due to conformational changes as a result of peptide binding to a more distant site. However, we have shown previously [15] that peptide binding does not induce the same conformational change as inhibitor binding, nor does it alter protease sensitivity of N355 (data not shown), arguing against global conformational changes. This, together with the data presented below (Table 1), argue in favor of peptide binding in proximity to Cys117.

Peptide Binding is Sensitive to Modification of Histidine Residues

Figure 6A:
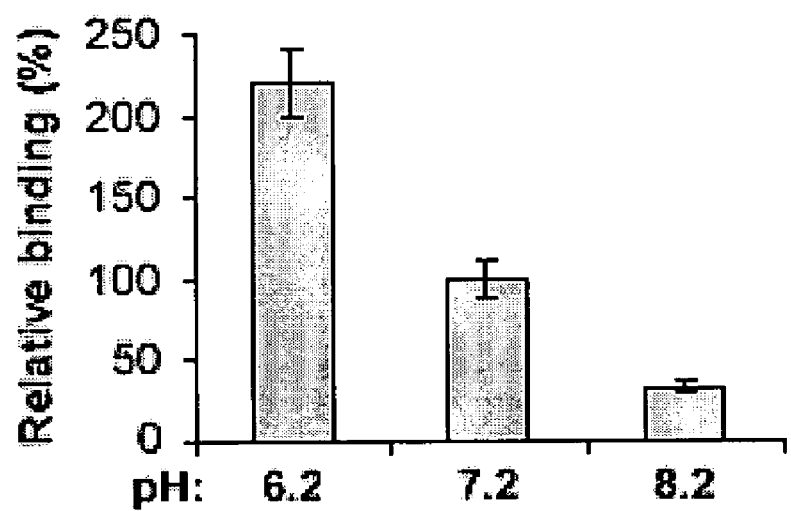
FIG. 6A. Peptide binding is pH dependent. Binding of N1-355 to the peptide VSV8 was assessed at various pH values using the solution binding assay described in [15]. At pH 7.2, either Hepes or Pipes were used with equal results, and the average set to 100%. Hepes was used at pH 8.2, and Pipes was used at pH 6.2, with the average binding values normalized to that obtained at the standard pH of 7.2.
Figure 6B:
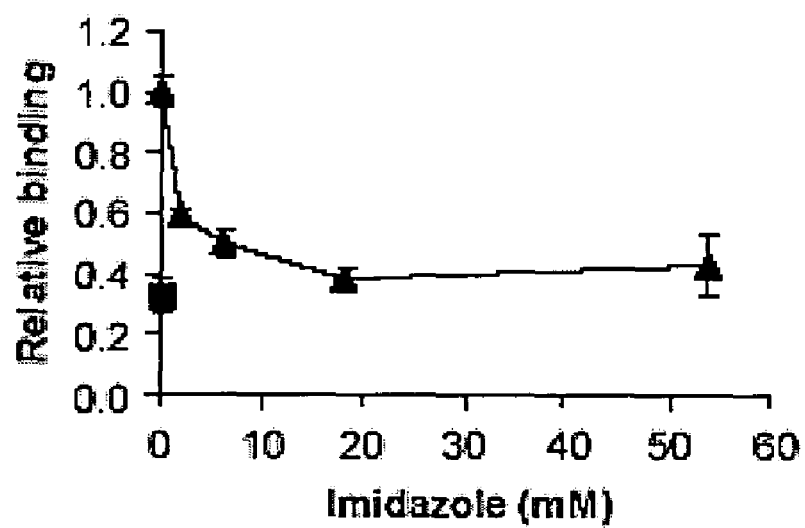
FIG. 6B. Peptide binding is sensitive to imidazole. Binding of N34-355 to peptide A was measured using the 96-well plate assay (Experimental Procedures). Imidazole was added to the indicated final concentrations and the binding at each concentration normalized to that without imidazole. Peptide binding in the presence of radicicol is shown as a measure of the nonspecific binding. Triangles, binding in the absence on the inhibitor; squares, binding in the presence of radicicol.
Figure 6C:
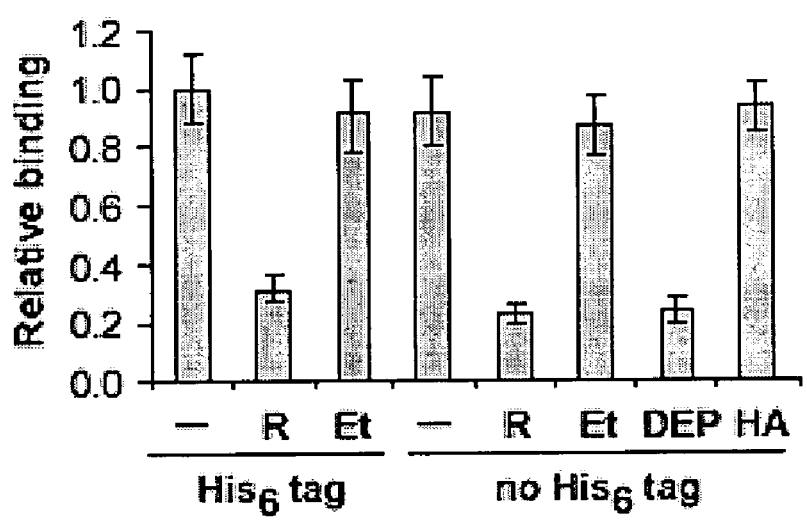
FIG. 6C. Binding activity is abolished by DEPC modification. The His6 tag of recombinant N355 was cleaved with factor Xa according to the manufacturer's instructions (Novagen) and the protein re-purified over a Ni-NTA column. The protein was treated with DEPC, as described herein, to modify histidines selectively. A portion of the modified protein was treated with 0.4M hydroxylamine (HA), to reverse the DEPC effect. Modification with ethanol was used as a solvent control. Radicicol treatment was used to measure specific peptide binding. The untreated and modified proteins were allowed to bind to peptide A-coated plates (0.7 μg protein per well) and binding was quantified by indirect reaction with 9G10 Mab (Affinity Bioreagents) followed by HRP-goat anti-rat (Jackson Labs). Triplicate data points are from a representative experiment. DEPC decreased binding to the background level while HA completely reversed the DEPC effect. Removal of the His6 tag had no effect on either efficiency or specificity of binding. R, radicicol; Et, ethanol; DEP, treatment with DEPC; HA, treatment with DEPC followed by hydroxylamine.

The third approach to defining the peptide-binding site derived from the observation that peptide binding was pH sensitive (FIG. 6A and ref. [1]). Binding was inhibited above pH 7.2 and was stimulated at pH near 6.0. In addition, binding was sensitive to imidazole; the presence of 6 mM imidazole reduced peptide binding by half (FIG. 6B). Both observations suggested that histidine residues might be involved in peptide binding by GRP94. Diethyl pyrocarbonate (DEPC) N-carbethoxyiates the imidazole ring of histidine in a highly specific manner under certain conditions [25, 26] and is therefore useful in defining the role of histidines. DEPC treatment of N34-355 (after cleavage of the His6 tag) abolished the peptide-binding activity of the protein as effectively as the inhibitor radicicol, while the ethanol solvent alone had no inhibitory effect (FIG. 6C). Hydroxylamine (HA) treatment restored the activity of the DEPC modified protein (FIG. 6C), confirming that only modified His residues and not other amino acids [26] were important for the change in activity.

His125 is Important for Peptide Binding

Figure 7A:
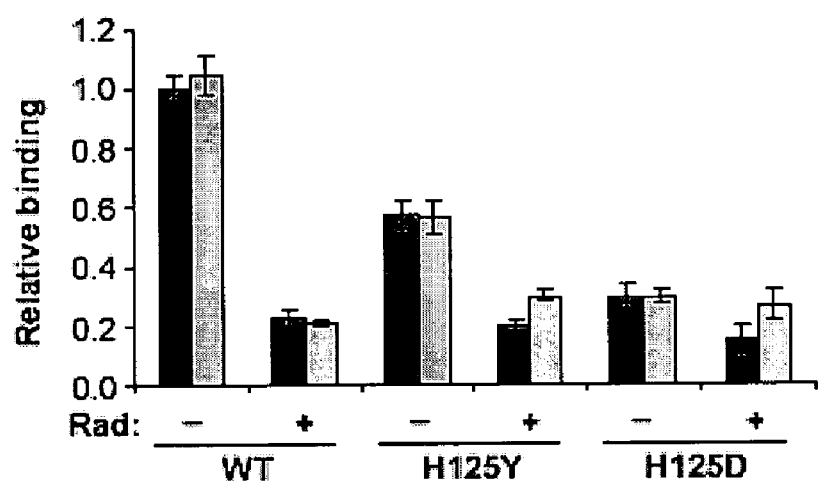
FIG. 7A. Alteration of His125 affects N34-355 binding to peptide A. Wild type N34-355, H125Y or H125D proteins were purified by metal chelate chromatography and their ability to bind peptide was tested in the plate assay (see Methods). Inhibition by radicicol (300 μM) served as a specificity control (Rad). The binding was measured at two protein input levels (0.7 or 2 μg) based on the level of saturation binding for the WT protein. The data shown are averages and standard error of triplicate points in two experiments. Black bars, 0.7 μg protein; grey bars, 2 μg protein.
Figure 7B:
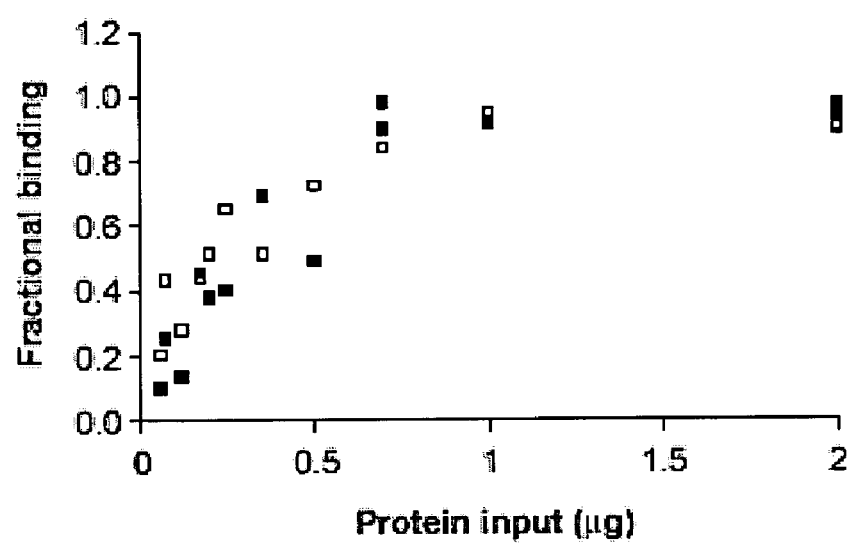
FIG. 7B. Fractional occupancy curves of wild type and H125Y. The amounts of peptide-bound protein, calculated as a fraction of the saturation binding level for each protein, is shown as a function of the input of protein. Filled squares, values from three independent dose-binding experiments for the wild type protein. Empty squares, values from three independent experiments for H125Y.
Figure 7C:
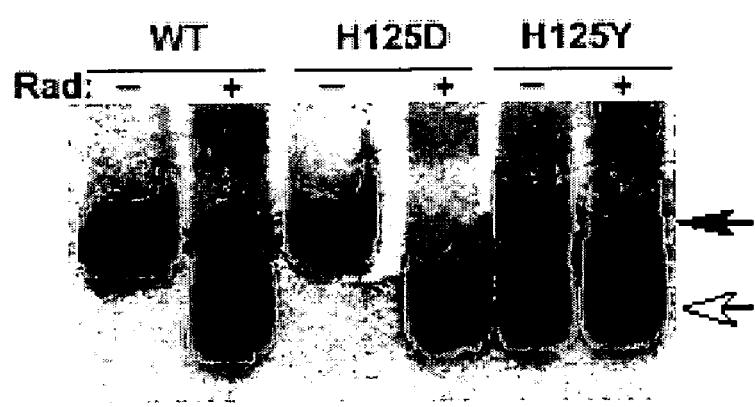
FIG. 7C. The H125D mutant shows the expected structural change upon radicicol binding. H125D and H125Y were compared to WT protein using blue native gel electrophoresis. Each protein (10 μg) was treated with either 300 μM radicicol or with DMSO and then loaded on each of two adjacent gel lanes. After electrophoresis, the gel was stained with Coomassie blue. Wild type and H125D proteins migrated predominantly as monomers and the characteristic radicicol-induced mobility shift was observed for both. Although H125Y protein also migrated as a monomer, it was present in two different conformations. Approximately half of H125Y showed increased mobility even in the absence of radicicol, while the other half showed both expected mobility and radicicol-induced conformational change. Black arrow, unbound protein; white arrow, radicicol-bound protein.

The N34-355 protein has 4 His residues, at positions 125, 194, 200 and 353. Based on the model (FIG. 2B), His125 was deemed to be the histidine residue most likely to be involved in peptide binding site. We therefore mutated His125 to either Asp, altering the charge, or to Tyr, replacing the imidazole ring with a phenol ring. The mutated H125D protein had almost no peptide binding activity, and the H125Y protein—only partial activity (FIG. 7A). Because the binding reaction has an unusually slow off rate [15] and therefore is not in equilibrium, Hill plots cannot be used to calculate the affinity, but the fractional occupancy plot can be used to estimate the association constants. The fractional occupancies calculated for the wild type and H125Y proteins are super-imposable (FIG. 7B), showing no significant difference between the association constants of the wild type and H125Y proteins. Because the saturation level of H125Y is approximately 0.6 of that of wild type, this analysis suggests that the H125Y mutation affects the active fraction of the protein, rather than binding by the active fraction. The loss of binding activity is not due to global misfolding of the mutant proteins. First, both were purified as soluble proteins and displayed chromatographic properties akin to the wild type protein. Second, both H125D and H125Y expressed the monoclonal 9G10 epitope (data not shown). Third, H125D retained its ability to bind the inhibitor radicicol and respond to it by altering its conformation, as shown by the native gel mobility test in FIG. 7C. The same test shows that approximately half of the H125Y mutant is found in the fast migrating conformation even in the absence of radicicol, supporting the conclusion that the H125Y mutation decreases the fraction of active protein. However, the population of this protein that shows correct mobility (approximately 50%) does appear to be capable of radicicol binding induced conformational change (FIG. 7C). The relative abundance of this population is in agreement with the peptide saturation level of H125Y (approximately 0.6 of that of wild type, FIG. 7A). Therefore, tyrosine at position 125 of N34-355, while decreasing the proportion of active protein, does not preclude peptide binding per se. Since, in contrast to histidine and tyrosine, aspartic acid at position 125 abolishes peptide binding, we propose that the nature of residue 125 is critical for peptide binding, confirming a strong prediction of the structural model.

His125 is in Physical Proximity to the Bound Peptide

Although the data above show that the environment of Cys117 changes upon peptide binding and that His125 modification either by DEPC or by a charge-altering mutation abolishes peptide binding, they can be explained in terms of transmission of conformational changes and thus do not formally show physical association. Therefore, we used the DEPC modification procedure in a peptide-protection experiment. The extent of DEPC modification was compared between a peptide-bound and peptide-free N34-355 (from which the His6 tag was removed), reasoning that if peptide is bound as modeled, it should protect His125 from modification. The proteins were analyzed by SELDI-TOF mass spectrometry (Table 1). Each Ncarbetoxylation adds 72 Da per His residue modified. The mass of N34-355 modified with DEPC increased by 289 Da compared to the unmodified protein, as expected from modification of all four His residues. That only His were modified was shown by the reversibility of the mass increase upon subsequent treatment with hydroxylamine [26]. When N34-355 was saturated with peptide A prior to the modification with DEPC, the mass gain was 73 Da less than in the absence of peptide (Table 1), as expected if one residue was protected from DEPC modification. Mass spectrometry of proteolytic fragments of DEPC-modified proteins confirms that the protected residue is His125 (data not shown). When the H125D mutant was used in the same manner, its mass increased by only 211-215 Da after modification with DEPC, whether peptide was present or not, as expected from a protein with only 3 His and unable to bind peptide (Table 1). These modification experiments argue that of the four histidines, only His125 is involved in peptide binding, and it is physically associated with the peptide.

TABLE 1

Protection of His125 from modification by peptide binding

| Protein and treatment | Observed MW | Observed Difference[a] | Expected Difference[b] |
|---|---|---|---|
| Wild type | 37742 | — | — |
| Wild type + DEPC | 38031 | +289 | +288 (4) |
| Wild type + DEPC + HA | 37758 | +16 | 0 |
| Wild type + peptid A + DEPC | 37955 | +213 | +216 (3) |

TABLE 1-continued

Protection of His125 from modification by peptide binding

| Protein and treatment | Observed MW | Observed Difference[a] | Expected Difference[b] |
|---|---|---|---|
| H125D | 37767 | — | — |
| H125F + DEPC | 37978 | +211 | +216 (3) |
| H125D + DEPC + HA | 37737 | −30 | 0 |
| H125D + peptide A + DEPC | 37982 | +215 | +216 (3) |

Wild type N34-355 or the H125D mutant proteins were incubated with saturating concentration of peptide A (or buffer alone) and the complexes purified by spin column gelfiltration. Proteins or protein-peptide complexes were then modified with DEPC (or the ethanol solvent alone) and adsorbed onto gold Ciphergen Protein chips. Masses of the treated proteins were determined by SELDI-TOF on a Ciphergen mass spectrometer calibrated with a standard set of proteins and peptides. The values given are for the single ionized peaks in each sample. They are from one experiment. a, the observed differences were calculated with respect to the unmodified protein (either wild type of H125D). The calculated molecular weight of wild type N34-355 is 37781 daltons and that of the H125D mutant is 22 daltons smaller. The differences obtained in two additional experiments were essentially identical. b, the expected differences were calculated based on modification of 3 or 4 His residues (indicated in parenthesis) and the addition of 72 daltons to the mass of the protein by N-carbethoxy-modification of each His.

DISCUSSION

Central to understanding the chaperone activity of GRP94, or its ability to stimulate peptide-specific T cell responses, is deciphering how it binds peptides. The work presented here provides an important part of the answer by locating the peptide-binding site. Together with our previous data [15], we show that the peptide-binding site of the chaperone GRP94 is located in a large groove in the N-terminal domain, opposite the nucleotide/geldanamycin/radicicol binding site. This peptide binding site was predicted by a computer docking algorithm and the following experimental observations are consistent with the prediction. a) Residues 1-33 and 223-355 are dispensable for retention of bound peptide, if not for binding; b) peptide binding is not hydrophobic in nature, consistent with the rather hydrophilic nature of the site; c) Cys117, located in a hydrophobic pocket, is affected by peptide binding, but can be modified covalently without inhibiting peptide binding; d) alteration of the binding site for the inhibitor radicicol does not prevent peptide binding; e) the nature of residue 125 is critical for peptide binding and His-125 is protected from modification with DEPC when peptide is bound; f) none of the other 3 histidines in N1-355 seems to be involved.

Substitution of Asp for His125 is sufficient to abolish the peptide binding activity of the protein. While mutations that reduce or abolish peptide binding can lie outside the binding pocket and act by affecting protein conformation, we show physical association between His125 and peptide, because of the protection from modification by the small molecule DEPC when peptide is bound. Therefore, we propose that the curved β sheet in the N-terminal domain is a peptide-binding site of this chaperone, at least in vitro, and is not merely a regulatory site. A more extensive survey of amino acids by mutagenesis and other biochemical methods to map the extent of the binding site is in progress.

If the computer-generated model is correct also in predicting the mode of peptide association, then binding is along the axis of the groove with contacts along the entire length of the peptide, reminiscent of the interactions of peptides with the groove of MHC class I proteins. The saddle-like geometry of the proposed binding site would allow GRP94-binding peptides to 'slide' along the axis of the groove, accounting for the observation that VSV8 binds with similar kinetics to VSV19, a peptide whose middle 8 amino acids are the VSV8 sequence. This aspect of the binding site would also explain the ability of GRP94 to bind peptides of different lengths, from 8-mers to 40-mers, with similar affinity [1, 13, 15].

While chaperones are generally thought to recognize hydrophobic peptides, as is true for HSP70s [27, 28], the features of peptides recognized by GRP94 seem different. The GRP94 groove identified here is lined with basic side chains (lysines and a histidine) and hydroxylic side chains (e.g. threonines), with only few hydrophobic side chains. The two binder peptides used in the present invention are also quite hydrophilic, their binding is sensitive to pH and is dissociated with high salt [15]. Thus, binding of at least these peptides seems to be driven by polar and electrostatic interactions, not hydrophobic. This observation is also consistent with the nature of the His125 mutations that affect binding: replacing the imidazole ring with a Tyr side chain still allowed partial binding, and substituting with Asp completely inhibited binding.

The β strands that form the floor for the peptide-binding site separate it from the radicicol-binding pocket. The β sheet in the center of the domain appears to play a role in both activities of the N-terminal domain. This is clearly demonstrated here for strand F of this β sheet (FIG. 4A). It contains at least one residue, Asp 128, whose side chain is directed toward, and is important for binding to radicicol, as predicted from the homology with HSP90 [18] and shown directly in this work. The same strand F also houses His125, whose central role in peptide binding is demonstrated here. Yet, despite their proximity, substitution of residues on the side of the strand that contacts the inhibitor does not significantly affect the contacts on the other side of the strand with bound peptide, and vice versa. We show that a radicicol-refractive mutant is able to bind peptide, and that a mutant in peptide binding still responds normally to radicicol. Peptide binding can be inhibited by binding of radicicol, but the inhibitor has to occupy its binding site first [15]. This suggests that binding of radicicol transmits a unidirectional change, either across the β sheet or more indirectly, so as to alter the peptidebinding groove.

The crystal structure of HSP90 has been solved both in the presence and absence of geldanamycin/radicicol/ATP and the differences in structure help define the conformational change induced by occupation of the nucleotide site [17, 18, 20, 29]. The two forms differ in three helices and a loop, about 35 residues altogether, which mostly either enable or constrain the entrance to the nucleotide binding pocket. The corresponding region in GRP94 is amino acids 135-174 (FIG. 4A). There is no obvious difference in the β sheet that would explain the inhibition of peptide binding by geldanamycin or radicicol. The observed inhibition, therefore, could be due to subtle changes or to more indirect transmission of conformational change from the 135-174 region to the opposite side of the molecule.

The identification of the peptide-binding site of GRP94 has direct relevance to all HSP90 proteins, since they have been reported to bind peptides, but none of their binding sites has yet been mapped. Scheibel et al. showed that the N-terminal 210 amino acids of yeast HSP90 form a monomeric domain sufficient to bind peptides, in geldanamycin- and ATP-sensitive manner [30], much like the minimal GRP94 construct described here. Addition of the negatively charged domain to the N-terminal domain increases peptide-binding affinity without affecting specificity [31]. Another similarity between yeast HSP90 and murine GRP94 is the apparent non-equilibrium nature of peptide binding ([15, 31] and this invention). Comparison of residues contributing to the saddle-like binding site shows that His125 is absent from all HSP90s, replaced by Thr in most HSP90 sequences. Because the HSP90 1-210 domain binds VSV8 less tightly than longer peptides [31], it is possible that the HSP90 N-terminal site is not as efficient in peptide binding as that of GRP94, or that its peptide specificity is different.

It is instructive to compare peptide binding by GRP94 with other peptide-binding sites. In HSP70 proteins, peptides also bind on top of a β sheet delineated by loops from the β sandwich domain [32, 33]. The peptide makes contacts with three β strands, is perpendicular to them and the binding groove has both hydrophobic and polar amino acids, but no charged residues [32, 33]. In comparison, the GRP94 peptide groove is wider, is made up of mostly polar residues and the peptide makes contacts more or less along the axis of three strands (strands G, F, and H). The interaction of GRP94 with peptide has several features in common with MHC proteins. In both MHC class I and class II the association constants are low and the off rates very slow. GRP94-peptide complexes are very stable, resistant even to SDS, like many MHC-peptide complexes [34]. When complexed with the Kb class I protein, the same VSV8 peptide used in the current work lies at approximately a 45o across a three-strand β sheet, constrained between two α helices [9], a topology that is similar to the one we suggest for the GRP94 binding groove. Interestingly, just like strand F, which provides important contact residues also on the other face of the β sheet with the inhibitors geldanamycin or radicicol, the same three β strands in MHC class I that interact with peptide also provide important contacts on the other face of the sheet with the $\beta_2$m subunit of the protein [35]. Depending on the MHC allele [36], mutations in $\beta_2$m can alter such contacts and affect peptide loading on the other face of the β sheet [37].

MHC-peptide complexes are designed to leave one face of the bound peptide solvent accessible, available for subsequent contacts with a T cell receptor. In HSP70 proteins, on the other hand, the bound peptide is buried, locked in place by an α helical domain acting as a reversible latch, whose motion is controlled by a nucleotide-induced conformational change [33]. Our present data are not sufficient to decide whether GRP94-peptide complexes resemble one or the other models. It is possible that the second, acidic domain of GRP94 provides a locking mechanism for peptide, because it is needed for at least one activity of the N-terminal domain [19] and because it is involved a conformational change induced by binding of inhibitor to the N-terminal domain [15]. The recently published structure of the N-terminal residues 48-316 of GRP94 [38] (residues 69-337 in the nomenclature used in that paper) shows no obvious part acting to constrain the bound peptide from above. On the other hand, the acidic domain is unordered in the crystal structure and therefore can potentially regulate access to the peptide binding pocket, in analogy to the long helix in HSP70 proteins [33].

The peptide-binding site identified in this work plays a key role in the T cell stimulatory activity of GRP94. Together with the data showing that the N-terminal GRP94 fragment can bind to antigen presenting cells and activate T cells [39], our data indicate that immunologically relevant peptides bind at this site and that the N34-355 fragment of GRP94 appears to account for peptide-specific activation of T cells. Because this site can be regulated by ligands that bind to the nucleotide site and to the hydrophobic pocket, binding of peptide to this site can be regulated by intracellular co-factors that are yet to be discovered.

REFERENCES FOR EXAMPLE 1

1. Blachere, N. E., Li, Z., Chandawarkar, R. Y., Suto, R., Jaikaria, N. S., Basu, S., Udono, H., and Srivastava, P. K. (1997) *J. Exp. Med.* 186, 1315-1322.
2. Singh-Jasuja, H., Scherer, H. U., Hilf, N., Arnold-Schild, D., Rammensee, H. G., Toes, R. E., and Schild, H. (2000) *Eur J Immunol* 30, 2211-2215.
3. Tamura, Y., Peng, P., Liu, K., Daou, M., and Srivastava, P. K. (1997) *Science* 278, 117-120.
4. Suto, R., and Srivastava, P. K. (1995) *Science* 269, 1585-1588.
5. Binder, R. J., Han, D. K., and Srivastava, P. K. (2000) *Nat Immunol* 1, 151-155.
6. Argon, Y., and Simen, B. B. (1999) *Semin Cell Dev Biol* 10, 495-505.
7. Young, J. C., Moarefi, I., and Hartl, F. U. (2001) *J Cell Biol* 154, 267-273.
8. Imarai, M., Goyarts, E. C., van Bleek, G. M., and Nathenson, S. G. (1995) *Cell Immunol* 160, 33-42.
9. Zhang, W., Young, A. C., Imarai, M., Nathenson, S. G., and Sacchettini, J. C. (1992) *Proc Natl Acad Sci USA* 89, 8403-8407.
10. Nieland, T. J., Tan, M. C., Monne-van Muijen, M., Koning, F., Kruisbeek, A. M., and vanBleek, G. M. (1996) *Proc. Natl. Acad. Sci. USA* 93, 6135-6139.
11. Wearsch, P. A., and Nicchitta, C. V. (1997) *J. Biol. Chem.* 272, 5152-5156.
12. Wearsch, P. A., Voglino, L., and Nicchitta, C. V. (1998) *Biochemistry* 37, 5709-5719.
13. Spee, P., and Neefjes, J. (1997) *Eur. J. Immunol.* 27, 2441-2449.
14. Baker-LePain, J. C., Reed, R. C., and Nicchitta, C. V. (2003) *Curr Opin Immunol* 15, 89-94.
15. Vogen, S. M., Gidalevitz, T., Biswas, C., Simen, B. S., Stein, E., Gulmen, F., and Argon, Y. (2002) *J. Biol. Chem.* 277, 40742-40750.
16. Robert, J., Menoret, A., Basu, S., Cohen, N., and Srivastava, P. R. (2001) *Eur J Immunol* 31, 186-195.
17. Prodromou, C., Roe, S. M., O'Brien, R., Ladbury, J. E., Piper, P. W., and Pearl, L. H. (1997) *Cell* 90, 65-75.
18. Roe, S. M., Prodromou, C., O'Brien, R., Ladbury, J. E., Piper, P. W., and Pearl, L. H. (1999) *J. Med. Chem.* 42, 260-266.
19. Schulte, T. W., Akinaga, S., Murakata, T., Agatsuma, T., Sugimoto, S., Nakano, H., Lee, Y. S., Simen, B. B., Argon, Y., Felts, S., Toft, D. O., Neckers, L. M., and Sharma, S. V. (1999) *Mol. Endocrinol.* 13, 1435-1448.
20. Stebbins, C. E., Russo, A. A., Schneider, C., Rosen, N., Hartl, F. U., and Pavletich, N. P. (1997) *Cell* 89, 239-250.
21. Prodromou, C., Siligardi, G., O'Brien, R., Woolfson, D. N., Regan, L., Panaretou, B., Ladbury, J. E., Piper, P. W., and Pearl, L. H. (1999) *EMBO J.* 18, 754-762.
22. Wassenberg, J. J., Reed, R. C., and Nicchitta, C. V. (2000) *J. Biol. Chem.* 275, 22806-22814.
23. Slavik, J. (1982) *Biochim BiophysActa* 694, 1-25.
24. Prendergast, F. G., Meyer, M., Carlson, G. L., Iida, S., and Potter, J. D. (1983) *J Biol Chem* 258, 7541-7544.

25. Kalkum, M., Przybylski, M., and Glocker, M. O. (1998) *Bioconjug Chem.* 9, 226-235.
26. Rai, S. S., and Wolff, J. (1998) *J Biol Chem* 273, 31131-31137.
27. Blond-Elguindi, S., Cwirla, S. E., Dower, W. J., Lipshutz, R. J., Sprang, S. R., Sambrook, J. F., and Gething, M. J. (1993) *Cell* 75, 717-728.
28. Gragerov, A., and Gottesman, M. E. (1994) *J. Mol. Biol.* 241, 133-135.
29. Prodromou, C., Roe, S. M., *Piper*, P. W., and Pearl, L. H. (1997) *Nat. Struct. Biol.* 4, 477-482.
30. Scheibel, T., Weikl, T., and Buchner, J. (1998) *Proc. Natl. Acad. Sci. USA* 95, 1495-1499.
31. Scheibel, T., Siegmund, H. I., Jaenicke, R., Ganz, P., Lilie, H., and Buchner, J. (1999) *Proc Natl Acad Sci USA* 96, 1297-1302.
32. Burkholder, W. F., Zhao, X., Zhu, X., Hendrickson, W. A., Gragerov, A., and Gottesman, M. E. (1996) *Proc. Natl. Acad. Sci. USA* 93, 10632-10637.
33. Zhu, X., Zhao, X., Burkholder, W. F., Gragerov, A., Ogata, C. M., Gottesman, M. E., and Hendrickson, W. A. (1996) *Science* 272, 1606-1614.
34. Collins, E. J., and Frelinger, J. A. (1998) *Immunol Rev* 163, 151-160.
35. Shields, M. J., Assefi, N., Hodgson, W., Kim, E. J., and Ribaudo, R. K. (1998) *J Immunol* 160, 2297-2307.
36. Smith, R. A., Myers, N. B., Robinson, M., Hansen, T. H., and Lee, D. R. (2002) *J Immunol* 169, 3105-3111.
37. Shields, M. J., Kubota, R., Hodgson, W., Jacobson, S., Biddison, W. E., and Ribaudo, R. K. (1998) *J Biol Chem* 273, 28010-28018.
38. Soldano, K. L., Jivan, A., Nicchitta, C. V., and Gewirth, D. T. (2003) *J. Biol. Chem.*
39. Baker-LePain, J. C., Sarzotti, M., Fields, T. A., Li, C. Y., and Nicchitta, C. V. (2002) *J Exp Med* 196, 1447-1459.
40. Schagger, H., Cramer, W. A., and von Jagow, G. (1994) *Analytical Biochemistry* 217, 220-230.

EXAMPLE 2

The Endoplasmic Reticulum Chaperone GRP94 is Essential for Mouse Gastrulation and Mesoderm Induction The endoplasmic reticulum chaperone GRP94 is expressed ubiquitously, but has few known client proteins, none of them involved in important developmental checkpoints. Targeted disruption of the murine GRP94 gene shows that it has an essential function in embryonic development. Grp94−/− embryos die in utero on day 7 of gestation, at the egg cylinder stage of development. They fail to develop mesoderm, a primitive streak, and the proamniotic cavity, the main differentiation events that normally occur at that stage and do not express key genes involved in mesoderm induction. The developmental defect is not due to dilution of maternal GRP94 and seems to reflect the activities of the chaperone. Grp94−/− cells divide at similar pace to their wild type counterparts. Furthermore, despite the known transcriptional regulation of GPR94 by low glucose tension, mutant ES cells proliferated like wild type cells in low glucose medium. On the other hand, mutant cells were much more sensitive to serum deprivation as well as to perturbation of calcium homeostasis. These data suggest that the requirements for GRP94 are very selective. We hypothesize that some secreted or cell-surface proteins, critical for mesoderm induction, depend on GRP94 for their proper expression, and that in the absence of this chaperone they fail to be efficiently presented when cell-cell interactions specify the proper fates of embryonic cells.

There is little known about GRP94 expression during mammalian development, although much of differentiation and organogenesis can be considered as involving natural metabolic stress responses. GRP94 transcripts are found ubiquitously, including in oocytes and 2-cell stage embryos [6]. At the protein level, it was not detected in undifferentiated F9 cells, whereas GRP78/BiP, another major ER stress protein, was found to be constitutively expressed. However, upon stress induced by a $Ca^{++}$ ionophore, both GRP94 and GRP78 protein expression was induced, just as in adult differentiated cells [6]. A 100 kDa protein, which is likely to be GRP94, but was not rigorously identified, was shown to be expressed on cells of the developing mouse embryo as early as the 4-cell stage [7]. At the egg cylinder stage and in 7- to 8.5-day embryos, expression was highest in the embryonic and extra-embryonic ectoderm and much lower in the visceral endoderm [8]. Additionally, mesoderm cells emerging from the primitive streak were positive [7]. At later stages (E9.5-13.5), during organogenesis, GRP94 was found to be constitutively expressed and localized most obviously within the developing heart, neuroepithelium, and surface ectoderm tissues [9]. These patterns of expression are often considered with respect to energy metabolism in the developing embryo: GRP94 expression is highest when and where there is most demand for its function as a stress protein.

The important functions of GRP94 have been investigated by several genetic methods. Antisense [10] or ribozyme-mediated depletion of GRP94 levels [8] affect both GRP94 and GRP78/BiP proteins and has shown that while their induction by stress conditions can be inhibited, their basal expression remains and is sufficient to support cell growth and proliferation. GRP94 shares many of its transcriptional regulatory elements with GRP78/BiP [11]. A GRP94-deficient murine pre-B lymphocyte line, 70Z/3, was isolated by Randow and Seed [12] based on sensitivity to lipopolysaccharide (LPS) stimulation, and shown to be capable of growth in culture. In *Arabidopsis*, a null grp94 mutation shows the protein to be important for plant development [13]. Both the Shepherd mutation and the 70Z/3 cell line show genetically that loss of GRP94 is not cell-lethal, but rather affects selected processes. These studies and the absence of GRP94 from yeast, are consistent with the correlation between GRP94 expression and multi-cellularity.

The above conclusion is probably related to another unusual feature of GRP94, which distinguishes it from most other chaperones: its small number of client proteins. In the GRP94-deficient cell line, only the surface expression of some, but not all integrins and Toll-like receptors was shown to be affected [12]. Similarly, we have shown that immunoglobulin biosynthesis is sensitive to pharmacological inhibition of GRP94, while the biosynthesis of MHC class I is not. Among the secreted and membrane proteins that are known to associate with GRP94 during their folding, there is no identifiable common structural element. It is therefore not presently possible to predict GRP94 substrates based on protein structure. Because of the apparent selectivity of GRP94 it was of interest to determine the effects of ablating GRP94 expression in the mouse.

Here we report that despite its ubiquitous expression in mouse tissues, targeting the murine gene for GRP94 gives rise to an embryonic lethal phenotype with a specific defect in a critical developmental checkpoint—the induction of mesoderm.

The following materials and methods are provided to facilitate the practice of Example 2.

Cloning and Mapping of grp94

Srivastava et al. [41] have shown that there is one mouse GRP94-encoding gene, located on chromosome 10, but only a partial genomic sequence is available. We used the porcine grp94 gene [42] as a guide to map the exon/intron organization of murine grp94. Nine phages encoding overlapping portions of murine GRP94 were isolated from a Sv129 genomic λ phage library (Stratagene), and their grp94 gene content mapped by exon PCR analysis. Phages containing approximately 23 kb genomic DNA each (data not shown) were used to construct the targeting vector.

The targeting construct was assembled in the vector pPNT1 [43]. An 8 kb EcoRV fragment extending from the intron between exons 3 and 4 to exon 8 was used as the right arm. The left arm was PCR-amplified and fully sequenced. It contains 1.5 kb of the grp94 starting in the 5'UTR and ending inside exon 3. The two arms are separated by a neomycin resistance cassette inserted in the opposite transcriptional direction. This created a stop codon, predicting a protein product that contains only 61 of the 781 amino acids of the mature GRP94 protein (plus 3 additional amino acids derived from the vector). Upstream of the grp94 sequence the targeting construct contained a thymidine kinase (tk) gene for negative selection.

Generation of grp94 Gene Targeted Mice

The targeting construct was electroporated into C1 ES cells (a kind gift from Dr. B. Hendrikson, the University of Chicago) and clones resistant to both ganciclovir and G418 were isolated and expanded. Twelve correctly targeted clones were identified, corresponding to a ratio of approximately 1 in 4 targeted to non-targeted ES clones. Six of these clones were expanded further and injected into blastocysts from pseudopregnant C57B1/6 WT female mice. The blastocysts were implanted and the females allowed to progress to term and produce chimeric animals. Seven male chimeric offspring with a brown coat color percentage of more than 75% were then bred to WT C57B1/6 females and the resulting offspring genotyped. Heterozygotes were inter-crossed to yield the F1 generation. Two independent mouse lines with germline transmission of the disrupted gene were derived. The phenotype of both lines was indistinguishable, so the data reported here were derived from line 18. The data are from mice backcrossed to the C57B1/6 background for at least 6 generations.

Generation of ES Cell Lines from Targeted Mice

ES cells from grp94+/− intercrosses were isolated by flushing the uterine ducts of E3.5 pregnant females with M2 medium (Sigma) using a 30½" gauge needle. Blastocysts were seeded in gelatinized tissue culture dishes in complete ES medium (DMEM, 20% FCS, Pen-Strep Glutamine, β-mercaptoethanol, non-essential amino acids, Hepes, 1000 u/mlESGRO). The inner cell mass was isolated after 4 days and expanded on irradiated murine embryonic fibroblasts. Colonies with ES cell morphology were genotyped and expanded.

Cell Proliferation and Survival Assays

Proliferation assays were performed using the CellTiter 96 AQueous Non-Radioactive Proliferation assay kit (Promega). Cells were grown for 2 weeks in medium containing different levels of glucose before proliferation assays were performed. Glucose-free medium and high glucose medium (4.5 g/L) were purchased from Invitrogen. In some experiments, cells were grown in the presence of 1 mM EGTA and their proliferation was quantified over a number of cell divisions. Serum deprivation experiments were set up by plating a known number of cells at 60% confluency or higher, and replacing the growth medium with serum-free medium when the cells were properly attached to the gelatin-coated plates. At the indicated time points, the plates were washed and the remaining attached cells were assayed for trypan blue (Fisher) exclusion. The detached cells were mostly trypan blue positive and were not able to attach upon replating. For the thapsigargin sensitivity assays, cell cultures were treated with drug concentrations of 0.25-3 μM between 3 and 24 hrs.

Immunohistochemistry and Whole Mount In Situ Hybridization

Decidual swellings were isolated from uterine muscular tissue and fixed over night in 4% paraformaldehyde at 4° C. The tissue was embedded in paraffin, sectioned at 5-7 μm and mounted on Superfrost slides (Fisher). For immunohistochemistry, the slides were dewaxed, blocked with $H_2O_2$ and treated with boiling 10 mM Citrate pH 6.0 for 10 minutes and then cooled to room temperature before antibody detection with 9G10 (Neomarkers). For H&E staining, slides were dewaxed and rehydrated, then stained for 4 minutes in Harris' hematoxylin (Sigma), rinsed until clear with tap water, dipped in 1% acid alcohol (1% HCl in 70% ethanol) to decolorize, rinsed in running tap water, and dipped in 100% ethanol. Slides were then dipped 3-4 times in eosin-phloxine (Fisher), dehydrated, cleared with xylene (Fisher) and mounted. FACS analysis of splenocytes was performed with fluorescent anti-IgM and anti-CD3 monoclonal antibodies (Pharmingen), using standard procedures.

For whole mount in situ hybridization, embryos (E6.5 and E7.5) were dissected from freshly isolated decidua, fixed for 45 minutes in cold 4% paraformaldehyde, and processed as described [44]. Briefly, embryos were re-hydrated, bleached in $H_2O_2$, permeabilized with proteinase K, and re-fixed. After treatment with sodium borohydride, the embryos were washed and pre-hybridized 1 h at 63° C. DIG-labeled probe (2 μg/ml)(Company for DIG) was added and hybridization proceeded for 20 hours at 63° C. Following washes at increasing stringency, probe binding was detected with Purple AP (Roche). The embryos were photographed through a dissection microscope using T-100 tungsten film (Kodak).

All riboprobes, except brachyury (T), were synthesized using T3 RNA polymerase (Promega) from cDNAs cloned into pBluescriptII KS+ (Stratagene). The brachyury template construct, a kind gift from Dr. Hermann, Max-Planck-Institut für Entwicklungsbiologie, Tubingen, Germany, was transcribed with T7 RNA polymerase (Promega).

LPS Assay

B cells from freshly isolated and homogenized mouse spleens were purified with Lympholyte M (Accurate Chemical) according to the manufacturer's instructions. Cells were plated in triplicates in 96 well plates in the absence or presence of 5 μg LPS (E. coli serotype 0127:B8, Sigma) per $10^6$ cells in 200 μl medium. The cells were incubated 72 hours at 37° C., 7.5% $CO_2$ and supernatants analyzed by enzyme-linked immunosorbent assay (ELISA) using alkaline phosphatase-labeled anti-mouse IgG (Southern Biotechnology Associates Clonotyping System) and 1 mg/ml PNPP substrate in substrate buffer (0.24 M $MgCl_2*6H_2O$, 0.9 M diethanolamine in 500 ml, pH 9.8) for detection.

RNA and cDNA Preparation

To prepare total RNA, entire embryos were homogenized by pipetting in 100 μl Trizol (Sigma). 10 μg glycogen was added as carrier, and the RNA was extracted with phenol/ chloroform and precipitated with ethanol. RNA from other embryos was prepared using the Qiagen RNeasy Mini kit (Qiagen). Typically, half of each RNA sample was used for cDNA preparation. Random primers (Gibco or Invitrogen) and dNTP mixture were added, incubated for 5 minutes at 65° C. and rapidly cooled on ice. After addition of reaction buffer and Placental RNase inhibitor (Roche), was added and the first strand synthesized using either Superscript II enzyme (Invitrogen) at for 50 minutes at 42° C., or Sensiscript reverse transcriptase (Qiagen) for 1 hour at 37° C. RNase H was subsequently used to remove the RNA template and minimize interference with PCR analysis.

Results

Targeting the Murine grp94 Gene.

Because GRP94 is found only in multi-cellular organisms, is not necessary for cell growth, and has a limited substrate range, this chaperone is probably not necessary for the folding of most proteins in the secretory pathway. We therefore hypothesized that targeted ablation of mouse grp94 would yield a defined phenotype rather than a catastrophic growth defect.

Figure 8A:
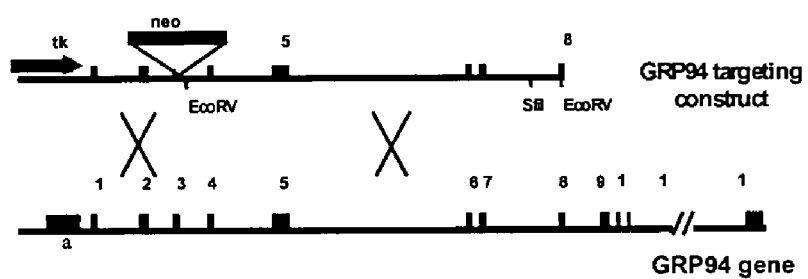
FIG. 8. Targeted disruption of the mouse GRP94 gene. Schematic of the murine gene and the targeting vector. The 18 exons of the GRP94 gene (black boxes) and the introns (thin lines, lengths determined by exon primer PCR and/or sequencing analysis) are drawn to scale, with a gap between exons 11 and 18. The targeting vector contains 1.2 kb 5' homology generated by PCR amplification and 8.0 kb 3' homology in an EcoRV fragment. The neo resistance cassette interrupts the coding region at the end of exon 3, 61 amino acids into the mature protein. Its transcriptional orientation is opposite that of the GRP94 gene, as marked by the arrow. The 5' homology region is flanked by tk, the herpes virus thymidine kinase gene used for negative selection.
FIG. 8B. Correct targeting in two mice was determined by Southern blotting with probe A located 5' of the insertion (see arrow in panel A), after digestion with HindIII (H) or EcoRI (R).

The murine grp94 gene, located on chromosome 10 [14], was targeted in strain129 C1 ES cells (FIG. 8A) and six correctly targeted clones, resistant to both ganciclovir and G418, were selected and injected into blastocysts from pseudo-pregnant C57B1/6 wild type (WT) female mice. Seven males exhibiting more than 75% coat color chimerism from two independent lines were then bred to WT C57B1/6 females and the resulting offspring genotyped. Heterozygotes were interbred as well as backcrossed to WT C57B1/6 for 12 generations.

Figure 8B:
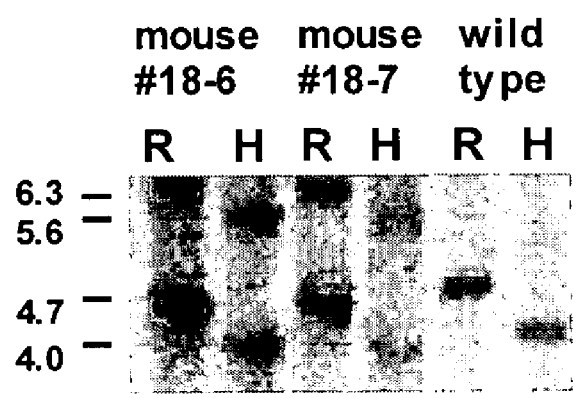

The expected protein product from this targeting construct contains 61 amino acids of the mature GRP94 protein (out of 781), plus three additional amino acids derived from the vector. This fragment is insufficient for either of the known activities of the protein—peptide binding and nucleotide binding [15-17]. A Southern blot analysis on genomic DNA isolated from one WT and two heterozygous F1 mice, using a 3' probe external to the targeting construct, is shown in FIG. 8B. RT-PCR analysis extended this finding by showing the absence of GRP94 transcripts from −/− embryos (FIG. 4A). Absence of GRP94 protein was verified by immunoblots of embryonic tissues and cells (see below) with the 9G10 monoclonal anti-GRP94, which recognizes an epitope between amino acids 266 and 347 [18].

Homozygous Deletion of grp94 has an Embryonic Lethal Phenotype

As seen in Table 2, viable grp94−/− mice were never obtained out of more than 900 progeny of intercrosses between heterozygotes. The fraction of heterozygous liveborn mice was 55.4%, instead of the 66.7% expected in the absence of −/− mice. Therefore, it appears that in addition to the homozygous mutant lethality, there is skewed inheritance of the knockout allele, a phenotype that is yet to be explored.

To determine the stage of embryonic lethality, we dissected out embryos at different stages of embryogenesis. At E14.5 and E10.5, no −/− embryos were found and even at E8.5, only few mutant embryos were identified (Table 2). Between E8.5 and E9.5, resorbing embryos were common. Between E5.5 and E7.5, however, we found a genotype distribution consistent with the expected 1:2:1 Mendelian ratio.

Figures 9A, 9B, 9C, 9D, 9E, 9F, 9G, 9H:
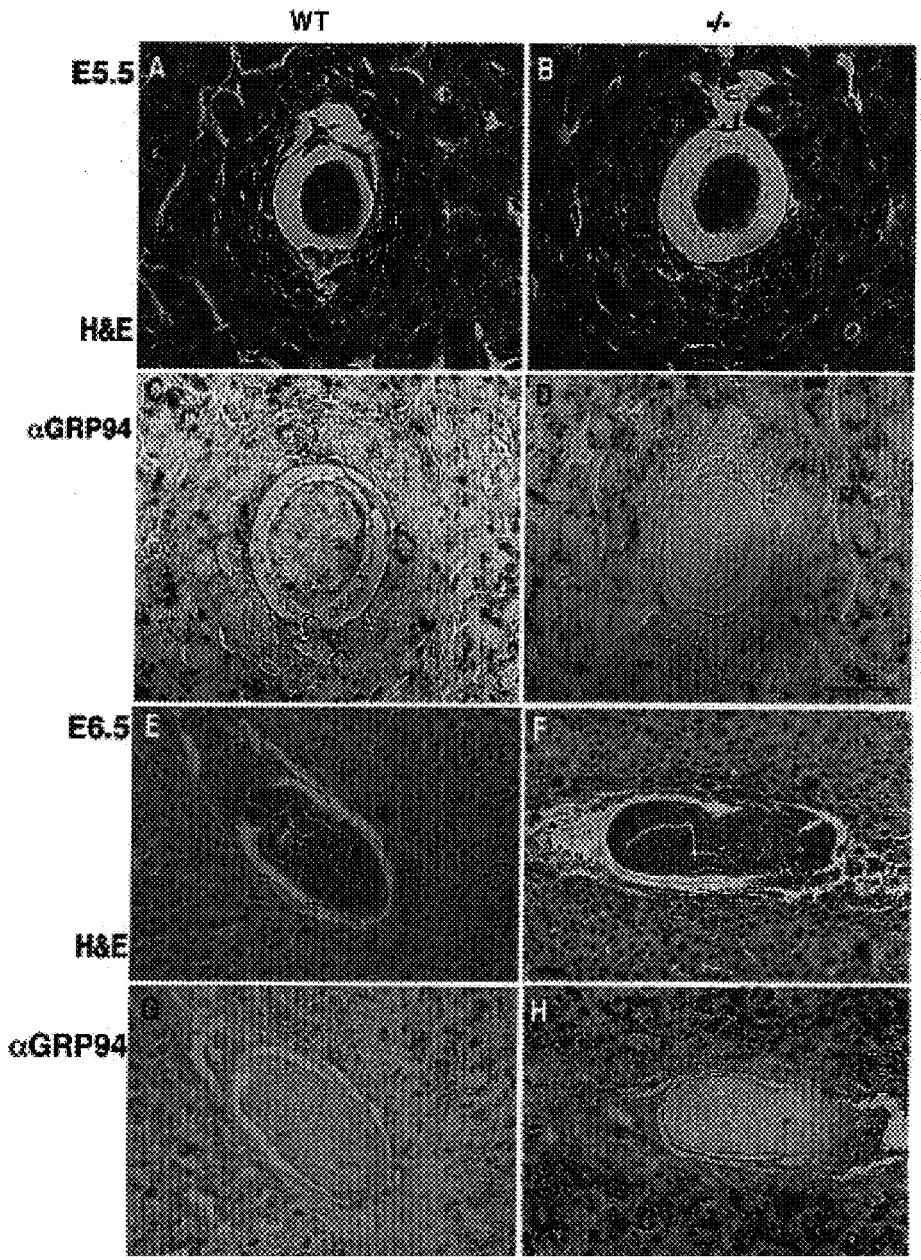
FIGS. 9A-H. Histological and immuno-staining analysis of WT (left panels) and mutant (right panels) embryos. E5.5 embryos (A-D) and E6.5 embryos (E-H) were fixed, sectioned and stained, as described in Materials and Methods, with either hematoxylin and eosin (H&E, A-B, E-F) or Mab 9G10 (αGRP94, C-D, G-H). VE, visceral endoderm; EPC, ectoplacental cone. * in panels E-F mark the developing pro-amniotic cavity.
Figures 9I, 9J, 9K, 9L:
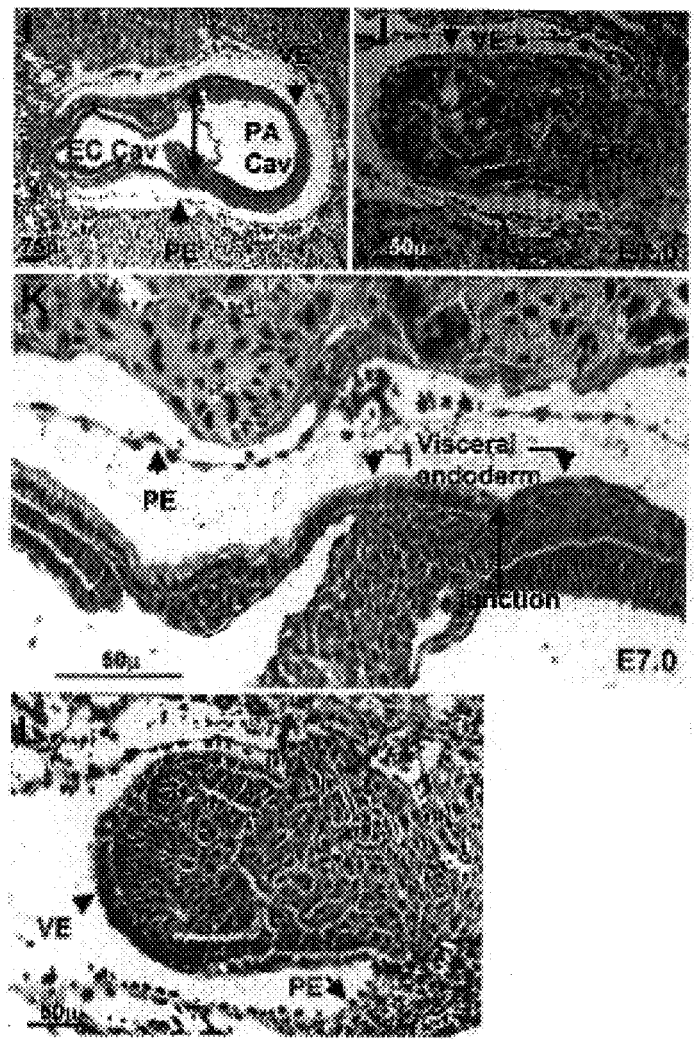
FIGS. 9I-L. Histological analysis of E7.5 embryos, showing the lack of mesoderm formation and lack of cavitation in mutant embryos (J) compared to WT embryos (I). PA Cav, pro-amniotic cavity; EC Cav, exoceolomic cavity; PE, parietal endoderm. The double arrow in panel I and the arrow in panel K mark the junction between the embryonic and extra-embryonic regions. K, higher magnification image of WT endoderm, showing the cuboidal architecture of cells on the extra-embryonic side of the junction and the squamous morphology of the endoderm cells on the embryonic side of the junction. L, a similar view of a mutant embryo, where the VE cells on both sides of the junction are cuboidal. Note also the lack of any evidence for pro-amniotic cavity. The PE cells do not look different in the mutant and WT embryos.

Up to the egg cylinder stage of development, grp94−/− embryos were morphologically indistinguishable from grp94+/+ embryos (FIGS. 9A-D). GRP94 protein expression was readily detected throughout the WT embryo (FIG. 9C). A day later, the grp94−/− embryos were still almost indistinguishable from WT embryos (FIGS. 9E-F). However, by E7.0-7.5, a dramatic difference was observed between grp94−/− and grp94+/embryos (FIGS. 9I and J). The grp94−/− embryos were much smaller than normal embryos and lacked any apparent lateral symmetry. Since they do not elongate properly, there is extra space in the yolk sac around the distal tip. Neither amnion nor chorion was formed and no proamniotic cavity was evident (FIG. 9J). The junction between the epiblast and the extra-embryonic region was less pronounced than in WT embryos, and the endodermal cell layer appeared abnormal (FIG. 9K). In normal embryos at this stage, the extra-embryonic region of the endoderm was composed of cuboidal/columnar cells with apical vacuoles and microvilli, and the embryonic region of the endodermal layer, beyond the junction, mostly consisted of squamous cells. In contrast, the endoderm of grp94−/− embryos appeared to consist of cuboidal cells in both the embryonic and the extra-embryonic regions (FIG. 9L, black arrowheads). The parietal endoderm, attached to Reichert's membrane, seemed normal in the −/− embryos (FIG. 9L).

Remarkably, −/− embryos only occasionally exhibited ingression of primitive ectodermal cells as they start to form mesoderm, and only two germ layers were evident in these embryos, while normal ones clearly elaborated three germ layers (FIGS. 9I-L).

TABLE 2

| | Genotype distribution with age | | |
|---|---|---|---|
| Stage | +/+ | +/− | −/− |
| Newborn | 414 | 515 | 0 |
| E14.5 | 8 | 5 | 0 |
| E10.5 | 3 | 2 | 0* |
| E8.5 | 3 | 5 | 1** |
| E7.5 | 40 | 81 | 43 |
| E6.5 | 8 | 12 | 6 |

Figures 10A, 10B:
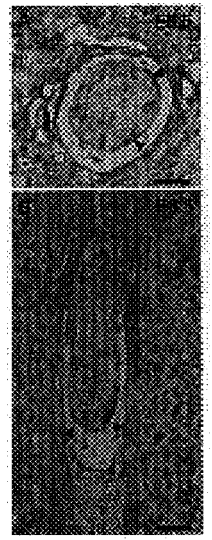
FIG. 10. Expression of GRP94 in pre-gastrulation embryos. Immunohistochemistry of E5.5 (A) and E6.5 (B) WT embryos with the anti-GRP94 monocloncal antibody 9G10. The sections shown are representative of multiple samples and were stained as described in Materials and Methods. Arrowhead point to clusters of visceral endoderm cells that display high protein expression. Bars, 50 μm in (A) and 100 μm in (B).

All genotype assignments are based on PCR reactions of genomic DNA isolated from either embryos or mice at the indicated ages.
*two empty sacs were found.
**one empty sac The Defect in grp94−/− Development Occurs at the Time of Gastrulation At the time the defect in development becomes evident in the grp94−/− embryos, normal embryos initiate gastrulation. During this process, the visceral endoderm cells are replaced and all three germ layers are derived from the epiblast. The visceral endoderm cells contribute only to the yolk sac and part of the extra-embryonic region, but have nevertheless been shown to have a role in the formation of body axes [19, 20]. Immunochemical staining for GRP94 showed it to be expressed in all cells at either E5.5 (FIG. 10A) or E6.5 (FIG. 10B). However, the staining is not uniform and there are clearly clusters of visceral endoderm cells that express more GRP94 than other endoderm or ectoderm cells (FIG. 10). Importantly, the level of expression in the embryo proper and in the extra-embryonic tissue is not significantly different from that in the surrounding maternal tissue.

Figures 11A, 11B, 11C, 11D, 11E, 11F, 11G:
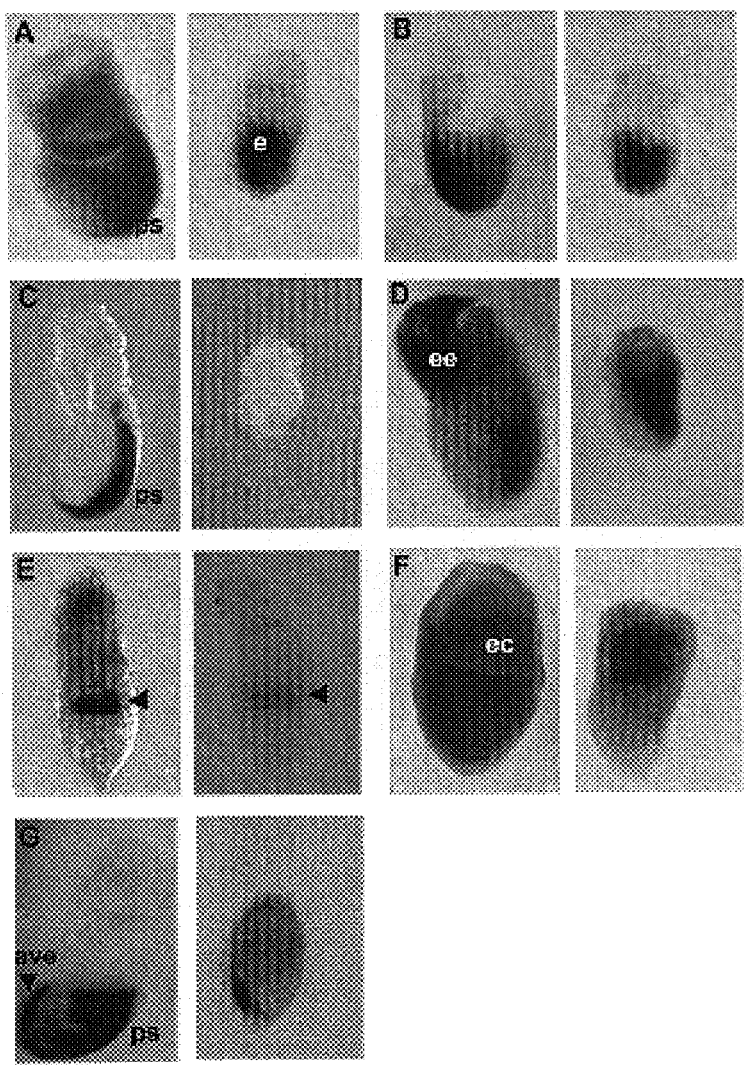
FIG. 11A. Oct4 is normally expressed throughout the epiblast at E6.5 and later localized to the primitive streak (ps) at E7.5 in WT embryos. Mutants show sustained overall epiblast (e) expression.
FIG. 11B. Otx2 expression at E7.5 is localized to the anterior region of normal embryos, but is expressed in the entire epiblast of the mutant.
FIG. 11C. Brachyury is expressed in the primitive streak at E7.5 in normal embryos, but is not detectable in E7.5 mutant embryos.
FIG. 11D. Eomes is expressed in the extra-embryonic ectoderm (ee) and developing primitive streak at E6.5 and is later localized to the primitive streak at E7.5 in WT embryos. Mutant embryos at E7.5 resemble WT embryos at E6.5.
FIG. 11E. Bmp4 expression in E6.5. Bmp4 is expressed normally in the proximal extra-embryonic ectoderm of both normal and mutant embryos (arrows).
FIG. 11F. Bmp4 expression is also detected at E7.5 in the extra-embryonic mesoderm lining the exocoelomic cavity (ec) of WT embryos. Mutant embryos express Bmp4 only in the proximal extra-embryonic ectoderm, as shown by arrows.
FIG. 11G. Lim1 is expressed in the AVE and mesodermal wings of WT E7.5 embryos, but in mutants, mesoderm expression is absent.

The progression of gastrulation is commonly monitored by the expression of transcription factors involved in cell fate specification, and therefore we analyzed grp94−/− embryos by in situ hybridization and semi-quantitative RT-PCR. Oct4, a transcription factor whose expression is detected in normal embryos already at E4.5 [21], is expressed throughout the epiblast at E6.5, and over the next day becomes progressively concentrated in the primitive streak (FIG. 11A). In E7.5−/− embryos, the distribution of Oct4 transcripts resembles that of E.6.5 WT embryos (FIG. 11A). Otx2 is a homeobox transcription factor expressed ubiquitously in the embryonic ectoderm and visceral endoderm before gastrulation and is progressively restricted to the anterior region of the embryo between E6.5 and 7.5, as the primitive streak elongates [45]. In E7.5 grp94−/− embryos, Otx2 expressed in the entire ectoderm of the mutant embryos, similar to its distribution in E6.5 WT embryos. Both of these markers confirm at a molecular level the conclusion that grp94−/− embryos do not progress past the E6.5 stage.

Figures 12A, 12B, 12C, 12D:
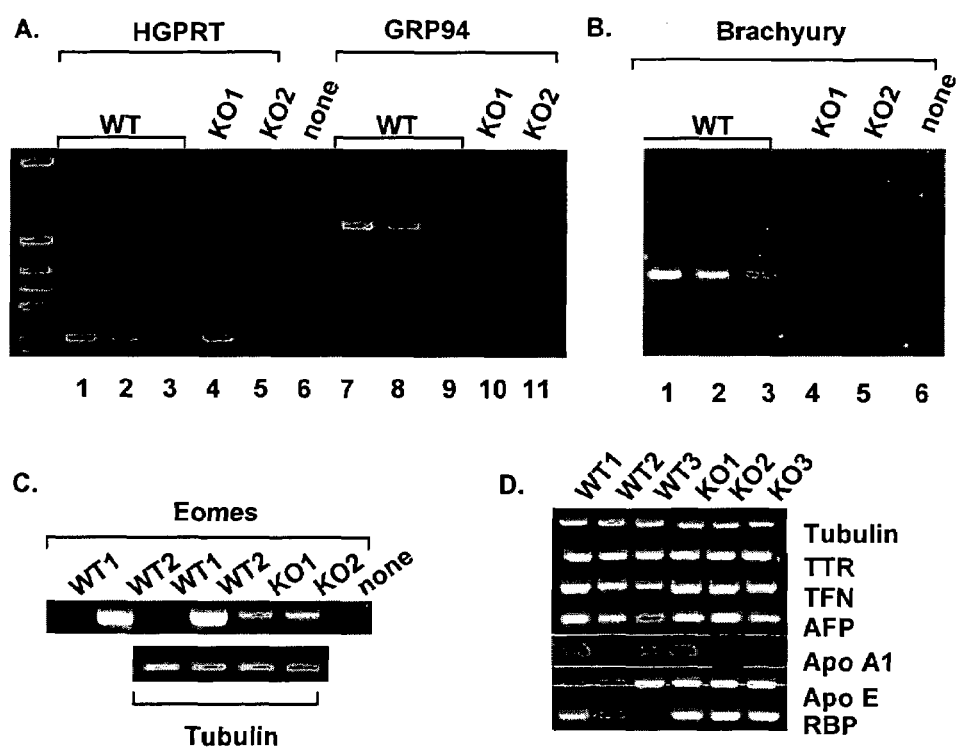
FIG. 12A. cDNA was prepared from whole E7.5 embryos carefully dissected away from maternal tissue. One wild type (WT) and two grp94−/− embryos (KO1 and KO2) are shown. The amount of input cDNA was normalized using HPRT primers in the linear range of the PCR reaction (lanes 1-6). Lane 1-3, 7-9: 0.25, 0.125, 0.063 μl WT cDNA, respectively. Lanes 4-5, 10-11: 1.5 μl grp94−/− cDNA from two separate −/− embryos.
FIG. 12B. The same cDNAs as in A were used to estimate the expression of brachyury, the canonical early mesoderm marker. Adjusting for the differences of input cDNA, the signal from KO1 is approximately 4 times more intense than the signal from KO2, but 2 orders of magnitude weaker than that from WT cDNA. The experiment shown is one out of four.
FIG. 12C. RT-PCR quantitation of Eomes expression. cDNA input was normalized using amplification of β-tubulin. Two WT and two mutant (KO) embryos are shown, out of 5 each.
FIG. 12D. RT-PCR analysis of VE marker expression. cDNAs from 3 WT and 3 KO embryos were compared, normalized as per β-tubulin expression. TTR, transthyretin; TFN, transferrin; AFP, α fetoprotein; ApoA1, apolipoprotein A1; ApoE, apolipoprotein E; RBP, retinol binding protein.

To determine if distinct regions of the embryo were specifically affected, we tested the expression of a number of markers for the anterior visceral endoderm (AVE). The expression of lim-1, which at E6.5-7.5 is restricted to the AVE [22], seemed reasonably normal in mutant embryos, though the domain of expression did not extending as proximally as in WT embryos of equivalent age (FIG. 10G). Similarly, a second AVE marker, Hex [23], is expressed anteriorly in mutant embryos (data not shown). Because a functional visceral endoderm is crucial for proper gastrulation [24], several other VE markers were tested by RT-PCR. Transcripts for transthyretin, transferrin, α fetoprotein, apolipoprotein A1 and E and retinol binding protein were all expressed equivalently in WT and mutant embryos (FIG. 12D). In conclusion, this marker analysis indicates that at least part of the axial differentiation program, formation of the AVE organizer, is not disrupted by the deficiency in GRP94.

Another region examined was the extra-embryonic ectoderm. Both normal and mutant embryos display expression of the marker Bmp4 [46] in the extra-embryonic ectoderm at E6.5 (FIG. 11E). At E7.5, grp94−/− embryos express Bmp4 only in the proximal extra-embryonic ectoderm, while in WT embryos it is expressed in the extra-embryonic mesoderm lining the exocoelomic cavity (FIG. 11F). This is again consistent with arrested differentiation at E6.5 without an obvious effect on the extra-embryonic ectoderm.

In contrast, the expression of brachyury (T), an early mesoderm marker [47], was markedly affected. E7.5 grp94−/− embryos were negative by in situ hybridization to a T antisense probe, while in the normal littermates brachyury was expressed in the primitive streak (FIG. 11C). Absence, or very low expression of brachyury was also confirmed by RT-PCR (FIG. 12). Amplification of transcripts from individual E7.5 embryos with brachyury-specific primers showed only a marginal brachyury signal in the grp94−/− samples, while hgprt transcripts were easily amplified. However, a second T-box protein, Eomes, which is involved in gastrulation and mesoderm induction at an earlier stage than brachyury [25], was expressed in −/− embryos. By whole mount in situ hybridization eomes is expressed in WT E7.5 embryos primarily at the primitive streak and in the extra-embryonic region [26]. In mutant embryos, the expression domain of eomes comprised a larger portion of the egg cylinder, including the area where the primitive streak would be expected to develop (FIG. 11D). The eomes expression pattern in E7.5 grp94−/− embryos is very similar to that of E6.5 WT embryos [26]. Consistent with this result, RT-PCR analysis shows that eomes transcripts are readily detected in mutant embryos at a level intermediate within the range seen in WT E7.5 embryos (FIG. 12C). The variability in WT embryos is consistent with the progressively restricted expression of eomes between E6.5 and E7.5 [26]. Finally, a later mesoderm marker, pMesogenin1 [27], was undetectable by RT-PCR (data not shown, N=2 mutant embryos). Together, the RT-PCR, hybridization analysis and the morphological data indicate that the defect in grp94−/− development is at an early gastrulation stage when the primitive streak should develop. Furthermore, GRP94 activity appears to be needed between the initial wave of eomes expression and the normal time of brachyury expression.

Live-Born Heterozygotes are Normal

Figures 13A, 13B, 13C:
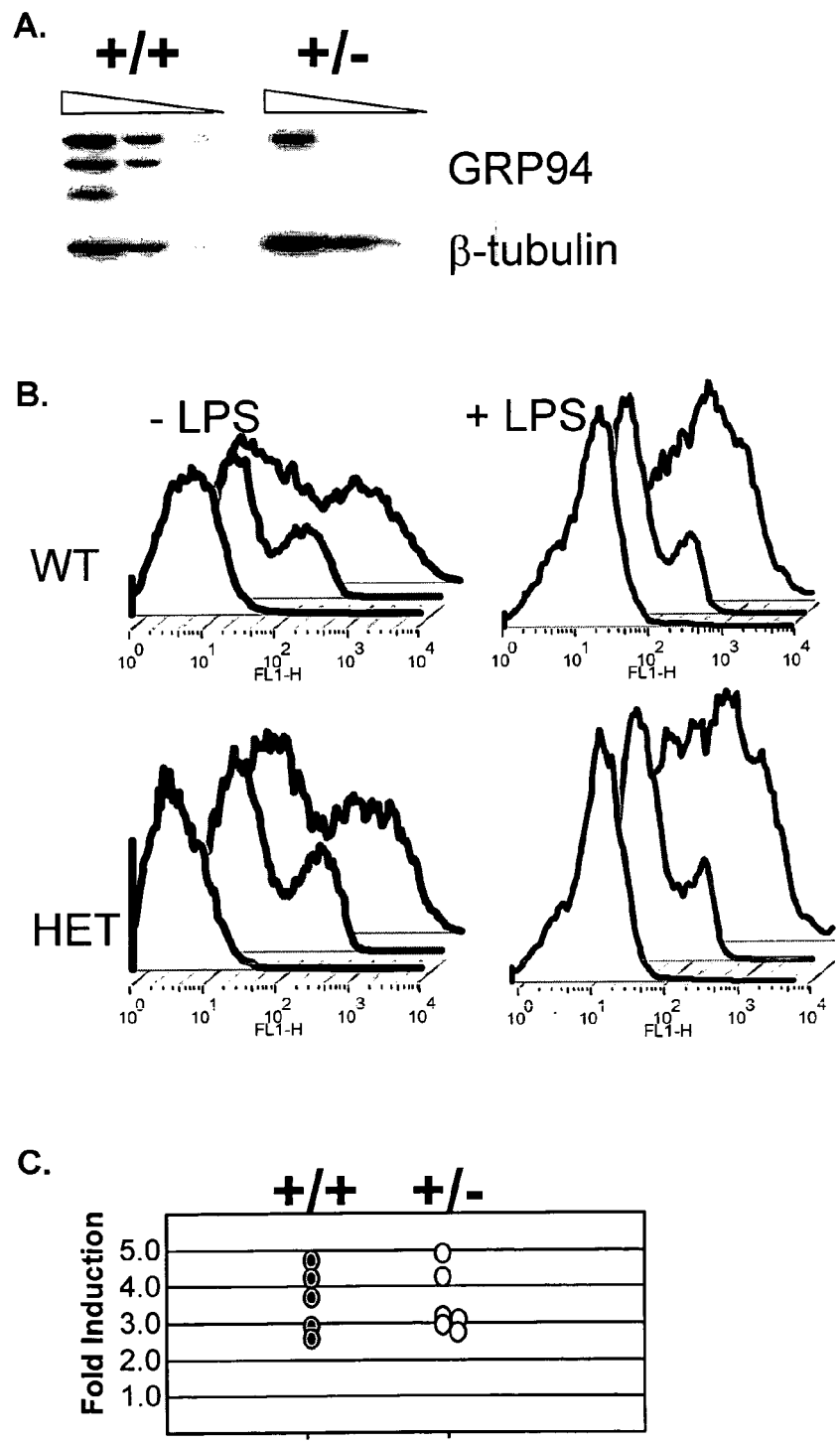
FIG. 13A. grp94+/− mice have a 50% reduction in GRP94 protein. Liver homogenates were prepared from heterozygous and WT mice and equal amounts of total protein were loaded in dilution series from left to right (100, 50, 25 μg) and analyzed by immuno-blotting with anti-GRP94 (9G10) (top panel) or with anti-β tubulin (bottom panel). The three GRP94 bands are the full-length protein and two smaller degradation products that are commonly seen in liver extracts. The blot shown is representative of four repetitions. Essentially the same result was also obtained by analysis of spleen lysates.
FIG. 13B. Expression of surface markers on splenocytes. Spleen cells from heterozygous (HET) or WT mice where cultured, treated with 50 µg/ml LPS to initiate proliferation of B cells and differentiation to Ig secreting cells. Three days later stained with either anti-CD3 antibodies to mark T cells (light gray) or with anti-IgM antibodies to mark B cells (dark grey). Black traces, unstained cells.
FIG. 13C. Induction of Ig secretion in splenocytes. Spleen cells from heterozygous or WT mice where treated with 50 µg/ml LPS as above, and three days later the levels of Ig in the medium were determined by ELISA with either anti-µ or anti-κ antibodies. The ratio of Ig in the medium before and after LPS treatment was calculated for each spleen culture and is plotted as the magnitude of the induction.

No phenotypic differences were observed between live-born heterozygote and WT mice. Appearance, weight, life span and fertility were all normal (data not shown). To investigate whether this was due to upregulation of GRP94 expression from the remaining allele, total protein was isolated from livers and spleens of grp94+/+ and grp94+/− mice and GRP94 expression was quantified by immuno-blotting. As shown in FIG. 13A, the amount of GRP94 in heterozygous tissues was close to 50% of WT levels, indicating that there was no upregulation of expression from the WT allele. Furthermore, the levels of three other major ER chaperones were quantified. The levels of BiP, calnexin, and ERp72 were identical in heterozygotes and WT animals (S. Vogen and T. Gidalevitz, data not shown), showing that these ER chaperones did not compensate for the decreased expression of GRP94. We conclude that half the normal expression of GRP94 is sufficient for normal murine physiology.

Since GRP94 is upregulated during the differentiation of resting B lymphocytes into immunoglobulin (Ig) secreting plasma cells [28, 29], we examined the effect of having only half as much GRP94 on B cell differentiation and on Ig secretion. Spleen cells were examined by FACS for surface Ig expression and by ELISA for Ig secretion before and after stimulation with LPS. As seen in FIG. 13B, there was no difference in the level of surface Ig expression either before or after 3 days of ex vivo LPS stimulation. Numbers of both T and B cells were also similar in mice of both genotypes. Third, no significant difference was detected in the level of IgM secreted by grp94+/− and grp94+/+ splenocytes (FIG. 13C). Therefore, 50% of the normal level of GRP94 is sufficient to support Ig secretion, a physiological response that entails massive upregulation of ER chaperones [28, 29].

Differential Requirements for GRP94 Under Different Stress Conditions.

Figures 14A, 14B, 14C, 14D, 14E, 14F:
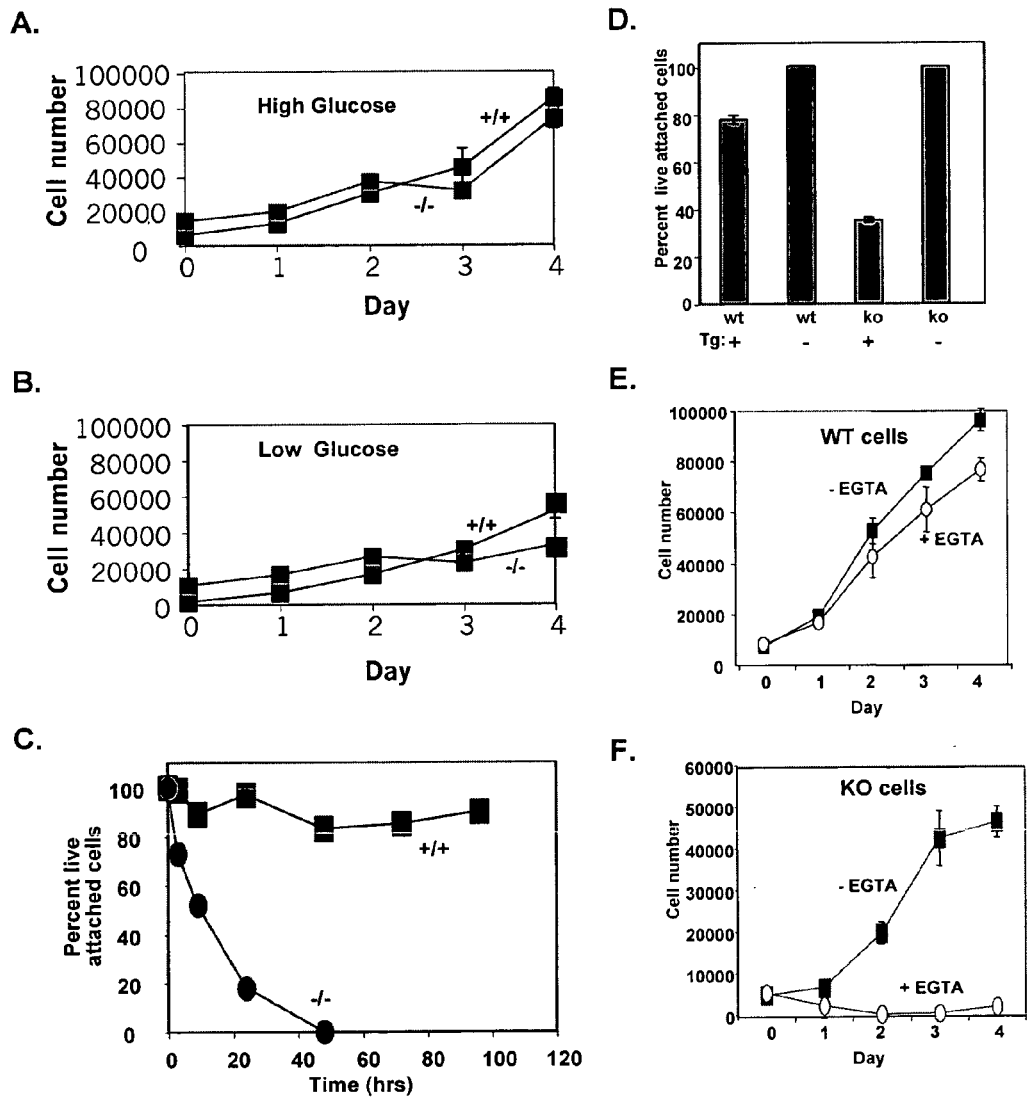
FIG. 14C, sensitivity of mutant cells to serum deprivation. Serum was withdrawn at time 0 and the live, attached cell counted at the indicated times (n=4). All the detached cells were trypan blue positive and failed to grow when re-plated in complete medium. Blue squares, WT cells of clone 42.1. Red circles, mutant cells of clone 14.1.
FIG. 14D. Differential sensitivity to Thapsigargin (Tg). WT and mutant ES cells were treated with 300 nM Thapsigargin (+), or mock treated (−), and their viability assessed after 6 hrs, a time where toxicity to WT cells was still marginal.
FIGS. 14E-F. WT and mutant ES cells were grown for the indicated times in the presence of absence of 1 mM EGTA and their viability was assessed.

An early embryonic lethal phenotype like that seen in grp94−/− embryos might be caused by slow proliferation, for instance due to a partial cell cycle block. Another possibility is that mutant embryos survive only as long as the cells contain a sufficient level of maternally-derived GRP94. To address these possibilities, we derived ES cell lines from pre-implantation E3.5 blastocysts. A matching pair of ES cell clones was established from grp94−/− and +/− littermate embryos. The grp94−/− ES cells (clone termed 14.1) were able to proliferate in culture for multiple generations, just like the +/+ ES clone (termed 42.1) (FIG. 14A). Thus, GRP94 is not required for cell growth and division per se. Furthermore, this observation provides evidence that the development arrest of mutant embryos is not simply due to dilution of maternal GRP94 during early embryogenesis.

Since GRP94 is a well-known stress protein, we examined the sensitivity of the GRP94-deficient cells to three cellular stress conditions: growth in low glucose, response to serum withdrawal and perturbation of calcium homeostasis. Surprisingly, grp94−/− cells grew as well as normal cells under low glucose tension (FIG. 14B), even as low as 2.5% of the normal glucose level. Thus, despite its transcriptional regulation by glucose depletion, GRP94 is not essential for cell survival under this stress condition. On the other hand, grp94−/− cells do not tolerate serum deprivation. Within 3 hrs after withdrawal of serum, 25% of mutant cells were dying, and only 20% survived after 24 hrs without serum, while there is no appreciable cell death of WT cells even after 48 hrs (FIG. 14C). GRP94 deficient cells are also more sensitive to treatment with thapsigargin, an inhibitor of the ER $Ca^{++}$-ATPase [30], with extensive cell death after 7 hrs in the presence of 300 nM thapsigargin (FIG. 14D). Furthermore, while WT cells can grow for 5 days in the presence of 1 mM EGTA, −/− cells cannot grow under such $Ca^{++}$-chelating conditions (FIG. 14E-F). These studies show that the requirement for GRP94 as a stress protein is selective, just like the requirement for GRP94 as a chaperone: it is essential for some stress responses, but not for all, presumably reflecting its limited substrate profile.

Figure 15:
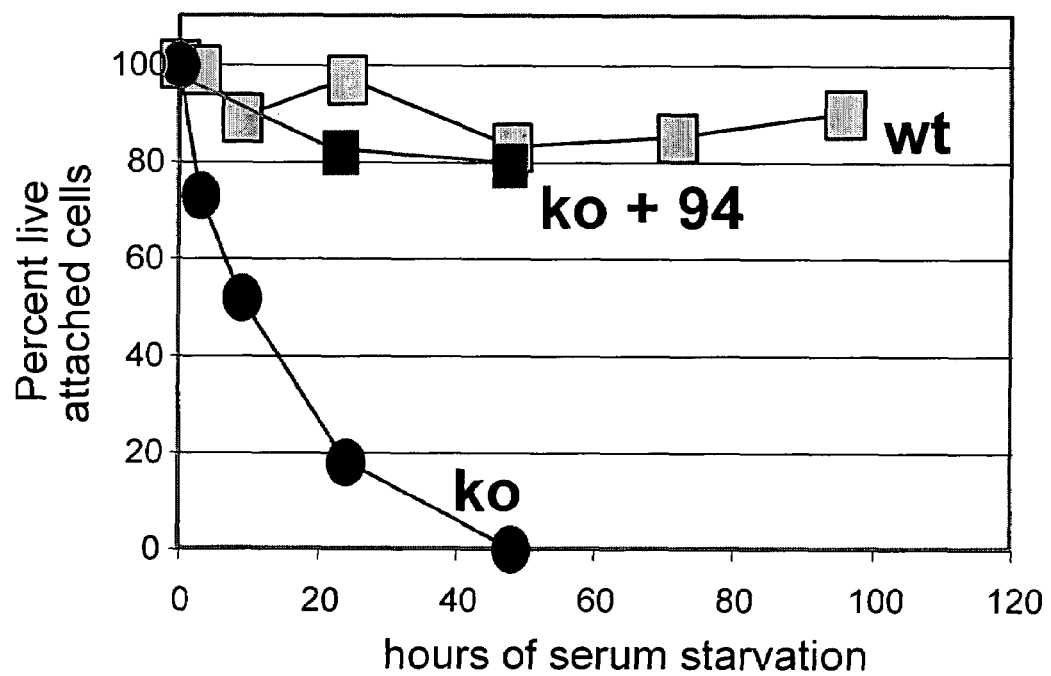
FIG. 15. A graph showing that GRP94-deficient cells are sensitive to serum withdrawal.
Figure 16:
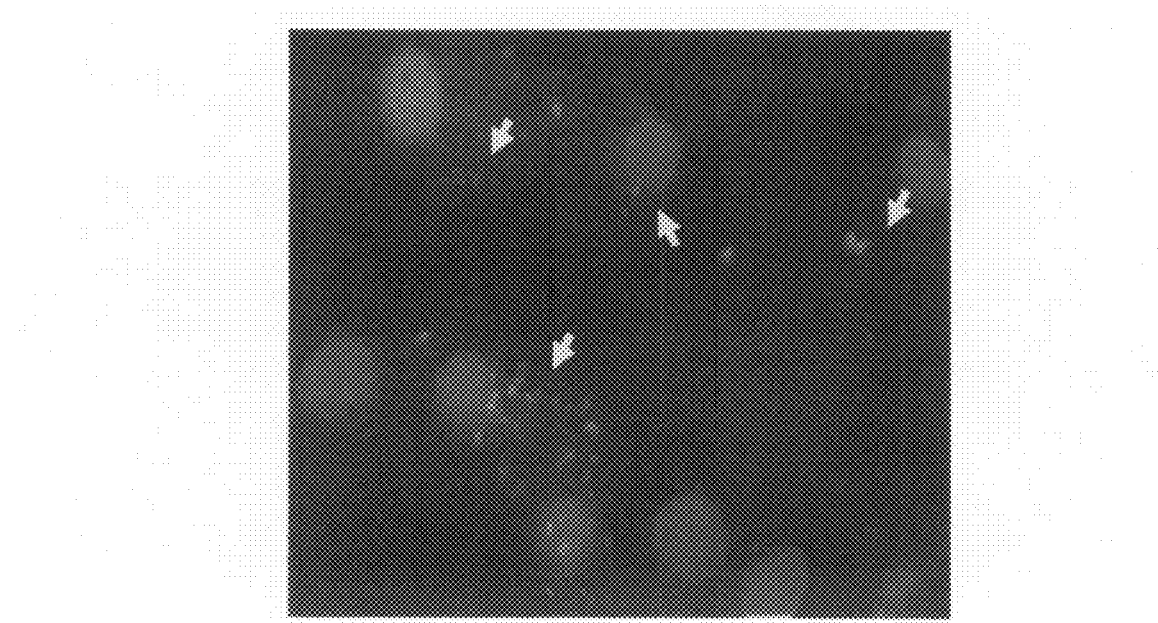
FIG. 16. A micrograph and binding assay showing that The N-terminal domain of GRP94 is taken up by dendritic cells.
Figure 16:
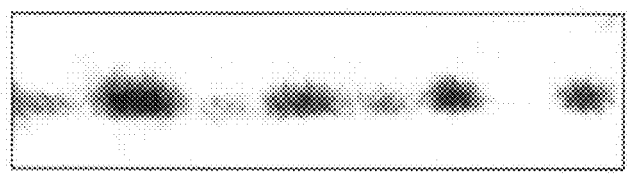

FIG. 15 shows that GRP94-deficient cells are sensitive to serum withdrawal. ES cell cultures were shifted from normal growth medium to serum-free medium and live cells were measured at the indicated times. As can be seen, wild type ES cells survive this stress for at least 4 days, while GRP94−/− cells dies rapidly. FIG. 16 demonstrates that the N-terminal domain of GRP94 is taken up by dendritic cells. The N-terminal domains of GRP94, either N1-355 or N34-355 are bound to purified mouse dendritic cells at 40° C., and are internalized upon warming to 37° C. into endosomal vesicles. The proteins are visualized by Texas-red-Streptavidin binding to their C-terminal biotinylated Lys370. A binding assay is shown to the right of the micrograph and quantifies the binding of N34-355 to dendritic cells. The protein was allowed to bind to the cells at 4° C. for 1 hr, either alone or in the presence of alpha 2 macroglobulin or in the presence of fucoidin, the inhibitors of the CD91 receptor and the Scavenger Receptor A, respectively. After the incubation, the cells were washed, lysed and analysed by immunoblotting. The extent of binding was quantified by phosphorimaging.

Figure 17:
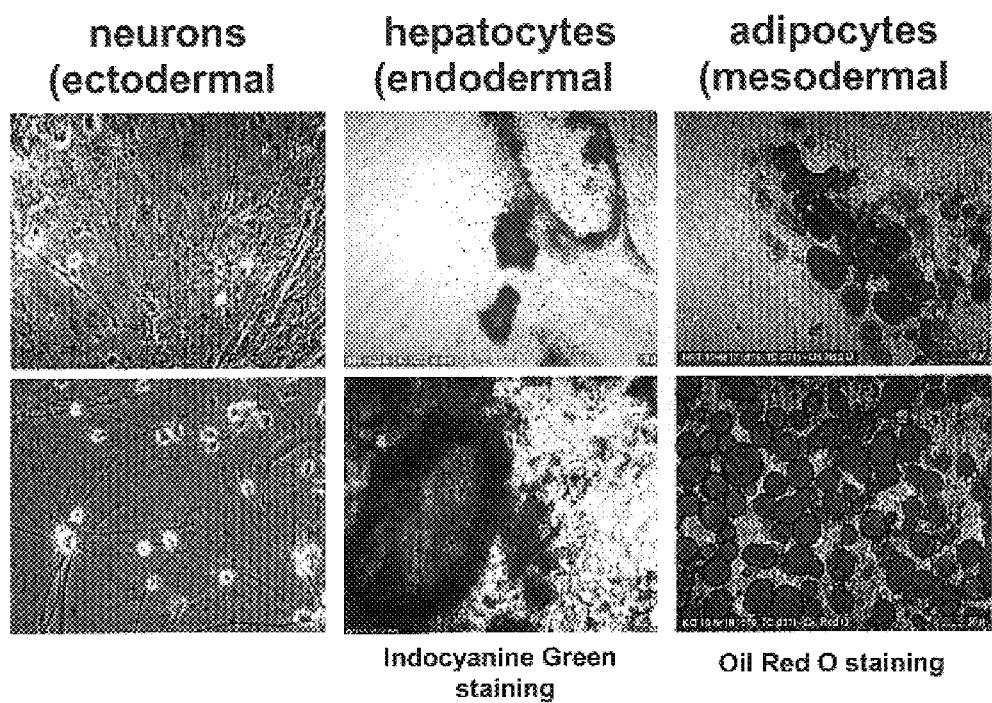
FIG. 17. A series of micrographs showing that GRP94 knockout (KO) cells can differentiate into cell types from all three germ layers.

GRP94 knockout (KO) cells can differentiate into cell types from all three germ layers as shown in FIG. 17. GRP94−/− or +/− cells were aggregated in hanging drops to form embryoid bodies, which were then induced to differentiate into various cells types by inclusion of DMSO or retinoic acid in the medium. Neurons (left panel) were identified by their morphology as well as by staining with neuron-specific antibodies to intermediate filament proteins. Hepatocytes (middle panel) were identified by indocyanine green stain as well as by PCR amplification of marker proteins. Adipocytes (right panel) were identified by Oil Red O staining of their lipid granules.

Figure 18:
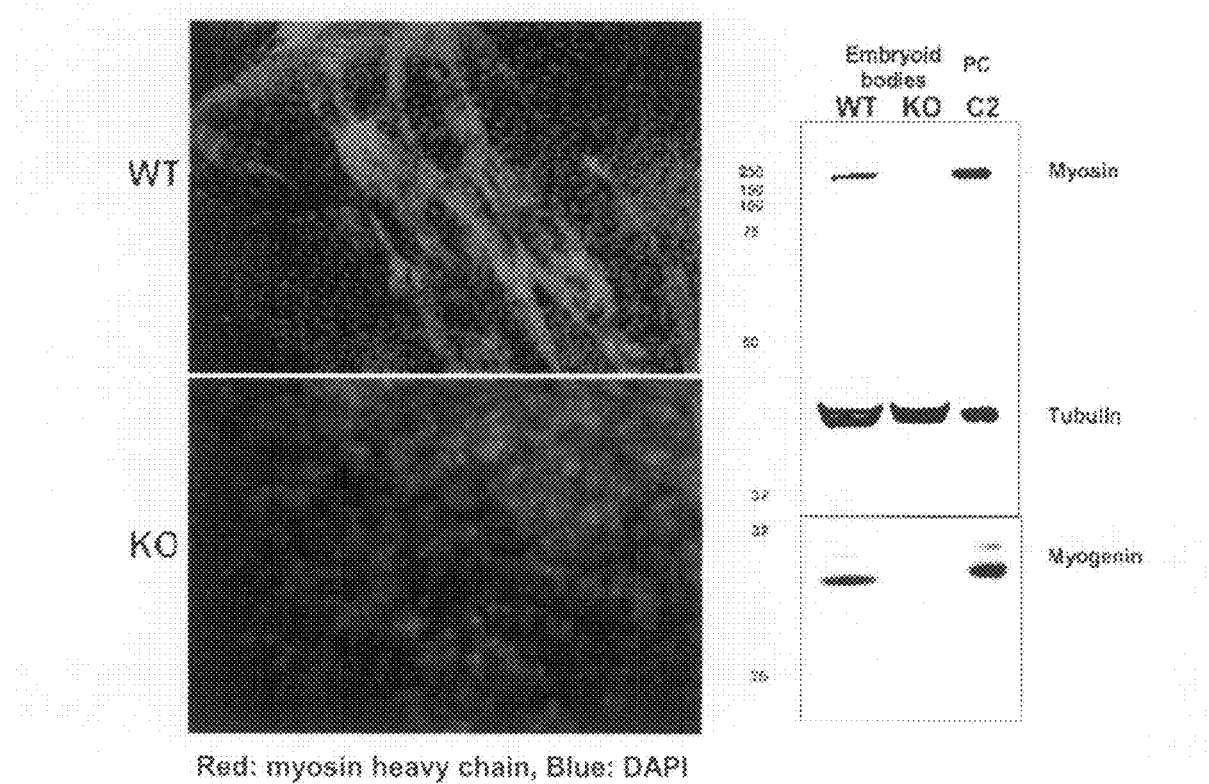
FIG. 18. A series of micrographs and blot showing that GRP94 deficient cells do not differentiate into muscle.

FIG. 18 reveals that GRP94 deficient cells do not differentiate into muscle. −/− ES cells were never able to give rise to skeletal myocytes (Left, bottom panel) although +/+ ES cells readily differentiated into myosin heavy chain positive cells (top panel).

Figure 19:
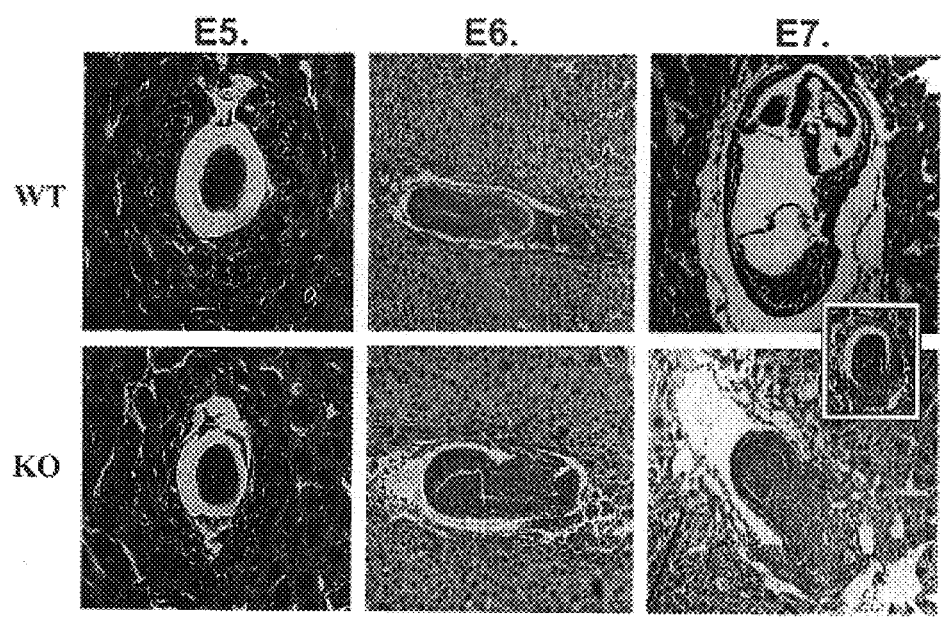
FIG. 19. A series of micrographs showing that knockout (KO) embryos arrest around E6.5.

FIG. 19 shows that knockout (KO) embryos arrest around E6.5. A-H. Histological analysis of WT (top panels) and mutant (bottom panels) embryos. Embryos at 5.5, 6.5 or 7.5 days of gestation were fixed, sectioned and stained with hematoxylin and eosin. Note the formation of cavities, amnion and chorion in E7.5 wild type embryo and the formation of left-right and dorsal-vetral asymmetry axes, whereas mutant embryos fail to exhibit any of these developmental hallmarks.

DISCUSSION

Many molecular chaperones are expressed abundantly and ubiquitously. It was therefore quite possible that ablation of one such chaperone, GRP94, would yield a catastrophic growth defect at the cellular level as soon as maternal GRP94 reached a threshold level. Alternatively, its function might be redundant and simply filled by another chaperone. Therefore, the phenotype of the targeted disruption of grp94 described here is surprising in its specificity. The embryonic lethality shows that grp94 is an essential gene for mouse development. Furthermore, in-depth analysis of the defect showed that the first stage which critically depends on GRP94 is gastrulation and mesoderm induction. This is earlier than the first stage that requires HSP90β, a cytosolic family member of GRP94, whose ablation arrests mouse development at E9.0-9.5 due to defective placental development [31]. The requirement for GRP94 is also earlier than that for calreticulin, another $Ca^{++}$-binding ER chaperone, whose ablation causes defective cardiac development [32].

The developmental arrest of grp94−/− embryos is not due to dilution of maternally inherited protein, and is likely autonomous to the embryo. GRP94 is expressed throughout post-implantation embryos as early as E4.5, if not before ([Li, 1991 #1038] and this work). Even more importantly, GRP94-deficient cells are capable of division and even of differentiation in culture, showing that GRP94 is not essential for cell proliferation per se. This conclusion extends the observations of Randow and Seed [12] and Ishiguro et al. [13] using a GRP94-deficient pre-B cell line and a naturally occurring *Arabidopsis* null mutant, respectively. Therefore, our interpretation of the rather precise stage of the developmental arrest is that GRP94s activity is necessary for proper execution of some aspect of an important checkpoint during embryogenesis.

In the absence of GRP94, embryonic development is arrested at the egg cylinder stage without formation of the primitive streak and the resultant induction of mesoderm. Analysis of transcripts of several mesoderm markers, in particular the transcription factors brachyury and eomesodermin, suggests that the differentiation program is arrested somewhere between the expression of eomes and brachyury. The visceral endoderm and the AVE develop normally in GRP94 deficient embryos, as judged by localization of Lim-1 and Hex transcripts and by quantitation of transcripts for transferrin receptor, retinol binding protein, and several other markers. Nevertheless, the differentiation of the anterior region is not entirely normal. First, the expression domain of Lim-1 and Hex is smaller than that in WT embryos, is much more localized and does not extend the entire circumference of the embryo. Second, the endoderm cells around the embryo proper remain cuboidal rather then becoming squamous. The relation of these defects to the major primitive streak defect is uncertain.

The developmental defect is also reflected in the phenotypes of grp94−/− ES cells in culture. These cells are more susceptible to stress caused by serum deprivation, as well as to disruption of calcium homeostasis, but surprisingly are no more susceptible to low glucose tension than WT ES cells. These biochemical phenotypes underscore the selectivity of GRP94 even in its role as a stress protein. Furthermore, the grp94−/− ES cells are capable of differentiation in culture, giving rise to multiple lineages derived from all three germ layers, but fail to give rise to either cardiac or skeletal muscle cells, again showing some specificity in the requirement for GRP94 (S. Wanderling, O. Ostrovsky and Y. Argon, manuscript in preparation).

The exact molecular defect that results from the absence of GRP94 has not been defined yet, but it seems reasonable to propose that the deficiency of this chaperone unmasks a critical requirement for GRP94 in the maturation of a developmentally important client protein. Since GRP94 is an ER chaperone, the putative client(s) could be either secreted or membrane-bound, and is likely to participate in cell-cell interactions that are required for mesoderm formation, a highly inductive process. It is noteworthy that the mesoderm induction defect in the mesd mouse has recently been identified as due to a defect in an ER resident protein with the capacity to interact with the LRP-5/6 membrane receptors [33]. The GRP94-induced embryonic deficiency may be due to a similar paradigm. Identifying GRP94 client proteins is made more difficult by the absence of structural information on the specificity of GRP94. Only a handful of substrates have been positively identified, and their small number precludes definition of a common motif. The only known client proteins with potential functions in early development are the Toll-like receptors 1, 2 and 4. Significantly, Toll was originally identified in *Drosophila* embryos as critically important for axis formation [34]. A similar function was subsequently identified in *Xenopus* embryos [35]. However, in higher eukaryotes, multiple Toll-like receptors are present and none has so far been shown to function in early mammalian development. If GRP94 recognizes a structural motif common to multiple Toll-like receptors, folding of all might be compromised in the absence of the chaperone, and potentially manifest as a defect in axis formation.

Conversely, genetic ablation of a number of other proteins have established their importance at the time of primitive streak formation and gastrulation. These include fibroblast growth factor receptors, activin receptors, bone morphogenetic receptors, and several of their respective ligands [36] [[37-40]. None of these proteins have been investigated in terms of dependence on GRP94 for membrane expression or secretion, but all are potential clients due to their biosynthesis in the endoplasmic reticulum.

In summary, we hypothesize that ER maturation of one or more developmentally important proteins depends critically on the activity of GRP94. In the absence of this molecular chaperone, the substrate(s) will not fold properly and cannot be released by the ER quality control machinery for transport to the cell surface. This in turn prevents critical ligand-receptor interactions from taking place and certain intercellular interactions required for mesoderm induction are precluded.

The following conclusions can be made based on the foregoing results: 1) Grp94 Is needed during mammalian development for mesoderm induction; 2) Grp94 is needed for differentiation in vitro of muscle cells, but is not needed for differentiation of other lineages; 3) Grp94 protects embryonic stem cells from apoptosis when deprived of serum, by supporting the secretion of a survival factor(s); 4) The peptide binding site of Grp94 is located in its N-terminal nucleotide binding domain; 5) His 125 is important for peptide binding and contacts the bound peptide; and 6) The same fragment which is sufficient for peptide binding is also sufficient for binding to, and internalization by dendritic cells.

REFERENCES FOR EXAMPLE 2

1. Lee, A. S., et al., *Transcriptional Regulation of Two Genes Specifically Induced by Glucose Starvation in a Hamster Mutant Fibroblast Cell Line.* J. Biol. Chem., 1983. 258: p. 597-603.
2. Drummond, I. A., et al., *Depletion of intracellular calcium stores by calcium ionophore A23187 induces the genes for glucose-regulated proteins in hamster fibroblasts.* J. Biol. Chem., 1987. 262(26): p. 12801-5.
3. Little, E. and A. S. Lee, *Generation of a mammalian cell line deficient in glucose-regulated protein stress induction through targeted ribozyme driven by a stress-inducible promoter.* J. Biol. Chem., 1995. 270(16): p. 9526-34.
4. Kim, Y. K., K. S. Kim, and A. S. Lee, *Regulation of the glucose-regulated protein genes by β-mercaptoethanol requires de novo protein synthesis and correlates with inhibition of protein glycosylation.* J. Cell. Physiol., 1987. 133 (3): p. 553-559.
5. Gass, J. N., N. M. Gifford, and J. W. Brewer, *Activation of an unfolded protein response during differentiation of antibody-secreting B cells.* J Biol Chem, 2002. 277(50): p. 49047-54.
6. Kim, S. K., Y. K. Kim, and A. S. Lee, *Expression of the glucose-regulated proteins (GRP94 and GRP78) in differentiated and undifferentiated mouse embryonic cells and the use of the GRP78 promoter as an expression system in embryonic cells.* Differentiation, 1990. 42: p. 153-159.
7. McCormick, P. J. and B. Babiarz, *Expression of a glucose-regulated cell surface protein in early mouse embryos.* Dev Biol, 1984. 105(2): p. 530-4.
8. Li, X. A. and A. S. Lee, *Competitive inhibition of a set of endoplasmic reticulum protein genes (GRP78, GRP94, and ERp72) retards cell growth and lowers viability after ionophore treatment.* Mol. Cell. Biol., 1991. 11(7): p. 3446-3453.
9. Barnes, J. A. and I. W. Smoak, *Immunolocalization and heart levels of GRP94 in the mouse during post-implantation development.* Anat. Embryol. (Berl), 1997. 196(4): p. 335-41.
10. Li, L. J., et al., *Establishment of a Chinese hamster ovary cell line that expresses grp78 antisense transcripts and suppresses A23187 induction of both GRP78 and GRP94.* J. Cell. Physiol., 1992. 153(3): p. 575-582.
11. Little, E., et al., *The glucose-regulated proteins (GRP78 and GRP94): functions, gene regulation, and applications.* Crit. Rev. Eukaryot. Gene Expr., 1994. 4(1): p. 1-18.
12. Randow, F. and B. Seed, *Endoplasmic reticulum chaperone gp96 is required for innate immunity but not cell viability.* Nat Cell Biol, 2001. 3(10): p. 891-6.
13. Ishiguro, S., et al., *SHEPHERD is the Arabidopsis GRP94 responsible for the formation of functional CLAVATA proteins.* Embo J, 2002. 21(5): p. 898-908.
14. Maki, R. G., et al., *Mapping of the genes for human endoplasmic reticular heat shock protein gp96/grp94.* Somat. Cell Mol. Genet., 1993. 19(1): p. 73-81.
15. Vogen, S. M., et al., *Radicicol-sensitive peptide binding to the N-terminal portion of GRP94.* J. Biol. Chem. 2002. 277: p. 40742-40750.
16. Rosser, M. F. N. and C. V. Nicchitta, *Ligand interactions in the adenosine nucleotide binding domain of the Hsp90 chaperone, GRP94. I. Evidence for allosteric regulation of ligand binding.* J. Biol. Chem., 2000. 275(30): p. 22798-22805.
17. Schulte, T. W., et al., *Interaction of radicicol with members of the heat shock protein 90 family of molecular chaperones.* Mol. Endocrinol., 1999. 13(9): p. 1435-1448.
18. Robert, J., et al., *Phylogenetic conservation of the molecular and immunological properties of the chaperones gp96 and hsp70.* Eur J Immunol, 2001. 31(1): p. 186-95.
19. Variet, I., J. Colignon, and E. J. Robertson, *nodal expression in the primitive endoderm is required for specification of the anterior axis during mouse gastrulation.* Development, 1997. 124(5): p. 1033-44.
20. Dufort, D., et al., *The transcription factor HNF3beta is required in visceral endoderm for normal primitive streak morphogenesis.* Development, 1998. 125(16): p. 3015-25.
21. Palmieri, S. L., et al., *Oct-4 transcription factor is differentially expressed in the mouse embryo during establishment of the first two extraembryonic cell lineages involved in implantation.* Dev Biol, 1994. 166(1): p. 259-67.

22. Barnes, J. D., et al., *Embryonic expression of Lim-1, the mouse homolog of Xenopus Xlim-1, suggests a role in lateral mesoderm differentiation and neurogenesis.* Dev Biol, 1994. 161(1): p. 168-78.
23. Thomas, P. Q., A. Brown, and R. S. Beddington, *Hex: a homeobox gene revealing peri-implantation asymmetry in the mouse embryo and an early transient marker of endothelial cell precursors.* Development, 1998. 125(1): p. 85-94.
24. Duncan, S. A., A. Nagy, and W. Chan, *Murine gastrulation requires HNF-4 regulated gene expression in the visceral endoderm: tetraploid rescue of Hnf-4(−/−) embryos.* Development, 1997. 124(2): p. 279-87.
25. Russ, A. P., et al., *Eomesodermin is required for mouse trophoblast development and mesoderm formation.* Nature, 2000. 404(6773): p. 95-9.
26. Ciruna, B. G. and J. Rossant, *Expression of the T-box gene Eomesodermin during early mouse development.* Mech Dev, 1999. 81(1-2): p. 199-203.
27. Yoon, J. K., R. T. Moon, and B. Wold, *The bHLH class protein pMesogenin1 can specify paraxial mesoderm phenotypes.* Dev Biol, 2000. 222(2): p. 376-91.
28. Lewis, M. J., R. A. Mazzarella, and M. Green, *Structure and assembly of the endoplasmic reticulum. The synthesis of three major endoplasmic reticulum proteins during lipopolysaccharide-induced differentiation of murine lymphocytes.* J. Biol. Chem., 1985. 260: p. 3050-3057.
29. Wiest, D. L., et al., *Membrane biogenesis during B cell differentiation: most endoplasmic reticulum proteins are expressed coordinately.* J. Cell Biol., 1990. 110(5): p. 1501-11.
30. Thastrup, O., et al., *Thapsigargin, a tumor promoter, discharges intracellular Ca2+ stores by specific inhibition of the endoplasmic reticulum Ca2+-ATPase.* Proc. Natl. Acad. Sci. USA, 1990. 87: p. 2466-2470.
31. Voss, A. K., T. Thomas, and P. Gruss, *Mice lacking HSP90beta fail to develop aplacental labyrinth.* Development, 2000. 127(1): p. 1-11.
32. Guo, L., et al., *Cardiac-specific expression of calcineurin reverses embryonic lethality in calreticulin-deficient mouse.* J Biol Chem, 2002. 277(52): p. 50776-9.
33. Hsieh, J. C., et al., *Mesd encodes an LRP5/6 chaperone essential for specification of mouse embryonic polarity.* Cell, 2003. 112(3): p. 355-67.
34. Anderson, K. V., L. Bokla, and C. Nusslein-Volhard, *Establishment of dorsal-ventral polarity in the Drosophila embryo: the induction of polarity by the Toll gene product.* Cell, 1985. 42(3): p. 791-8.
35. Prothmann, C., N. J. Armstrong, and R. A. Rupp, *The Toll/IL-1 receptor binding protein MyD88 is required for Xenopus axis formation.* Mech Dev, 2000. 97(1-2): p. 85-92.
36. Yamaguchi, T. P. and J. Rossant, *Fibroblast growth factors in mammalian development.* Curr Opin Genet Dev, 1995. 5(4): p. 485-91.
37. Mishina, Y., et al., *Multiple roles for activin-like kinase-2 signaling during mouse embryogenesis.* Dev Biol, 1999. 213(2): p. 314-26.
38. Roelen, B. A., et al., *Differential expression of BMP receptors in early mouse development.* Int J Dev Biol, 1997. 41(4): p. 541-9.
39. Gu, Z., et al., *The type I activin receptor ActRIB is required for egg cylinder organization and gastrulation in the mouse.* Genes Dev, 1998. 12(6): p. 844-57.
40. Weinstein, M., et al., *Failure of egg cylinder elongation and mesoderm induction in mouse embryos lacking the tumor suppressor smad2.* Proc Natl Acad Sci USA, 1998. 95(16): p. 9378-83.
41. Srivastava, P. K., C. A. Kozak, and L. J. Old, *Chromosomal assignment of the gene encoding the mouse tumor rejection antigen gp96.* Immunogenetics, 1988. 28(3): p. 205-7.
42. Dechert, U., et al., *A protein kinase isolated from porcine brain microvessels is similar to a class of heat-shock proteins.* Eur. J. Biochem., 1994. 225(3): p. 805-9.
43. Tybulewicz, V. L., et al., *Neonatal lethality and lymphopenia in mice with a homozygous disruption of the c-abl proto-oncogene.* Cell, 1991. 65(7): p. 1153-63.
44. Hogan, B. L., et al., *Manipulating the mouse embryo, a laboratory manual.* Second edition. 1994: Cold Spring Harbor Laboratory Press.
45. Simeone, A., D. Acampora, A. Mallamaci, A. Stornaiuolo, M. R. D'Apice, V. Nigro, and E. Boncinelli. 1993. *A vertebrate gene related to orthodenticle contains a homeodomain of the bicoid class and demarcates anterior neuroectoderm in the gastrulating mouse embryo.* Embo J 12:2735.
46. Coucouvanis, E., and G. R. Martin. 1999. *BMP signaling plays a role in visceral endoderm differentiation and cavitation in the early mouse embryo.* Development 126:535.
47. Wilkinson, D. G., S. Bhatt, and B. G. Herrmann. 1990. *Expression pattern of the mouse T gene and its role in mesoderm formation.* Nature 343:657.

EXAMPLE 3

A Tumor-protection Agent Including a Peptide Capable of Binding Grp94 Protein

This example describes modulation of the immune system response to tumors by using the molecular chaperone GRP94 to bind peptides to present tumor antigens. The invention is based on the supposition that the peptide specificity of GRP94 makes it particularly effective as a tumor-protection agent. Thus the invention provides a tumor vaccine based on the peptide-binding activity of a molecular chaperone, GRP94. In one aspect peptide sequences such as those provided in Table 3 will be complexed with GRP94 or HSP90 mini chaperones. Following complex formation, an effective amount of a composition comprising the complex will be administered to the cancer patient to stimulate a tumor specific CTL response. Alternatively, tumor associated peptides may be isolated from the patient to be treated and complexed with the GRP94 and HSP90 mini chaperones described herein. Either approach should stimulate immuno modulated tumor reduction or rejection. A similar approach can be employed for treating and eradicating viral infections using complexes comprising virus specific peptides and the mini-chaperones of the invention. Recombinant proteins (GRP94 derived or HSP90 derived) are incubated with synthetic peptides, typically at a vast molar excess of peptide because of the slow on-rate of binding. 4 micromoles of GRP94 can be saturated with 800 micromoles of synthetic binder peptide. The association can be enhanced by a 10 min 50° C. treatment of the protein, and in our hands the loading is highly efficient—up to 85% of the protein can be loaded with peptide.

TABLE 3

Examples of antigenic peptides that can be loaded on GRP94:

| Peptide Name | Sequence | Source | Restricted | GRP94 binding | Tumor relevant |
|---|---|---|---|---|---|
| VSV8 | RGYVYQGL | VSV N protein | $K^b$ | yes | mouse model |
| OVA 257-264 | SIINFEKL | Influenza | $K^b$ | yes | mouse model |
| RAH | RAHYNIVTF | HPV16 E-6 | HLA-A2 | yes, weak | Human ovarian carcinoma common antigen |
| PSA16 | VLVASRGRAV | PSA 16-25 | HLA-A2 | unknown | Human prostate common antigen |
| PSA 141 | FLTPKKLQCVDLHV ISNDVCAQV | PSA 141-170 | HLA-A2 and A3 | unknown | Human prostate common antigen |
| MAGE 3 | FLWGPRALV | Tyrosinase | HLA-A2 | yes | Human melanoma |
| Ras p5-14 | KLVVVGAGGV | Mutant ras 5-14 | HLA-A2.1 | unknown | Shared antigen many malignancies |

Figure Legend for Table 3 Sequence and SEQ ID NO: RGYVYQGL (SEQ ID NO: 5), SIINFEKL (SEQ ID NO: 8). RAHYNIVTF (SEQ ID NO: 9), VLVASRGRAV (SEQ ID NO: 10). FLTPKKLQCVDLHVISNDVCAQV (SEQ ID NO: 11), FLWGPRALV (SEQ ID NO: 12), KLVVVGAGGV (SEQ ID NO: 13)

Using a newly devised peptide-binding assay, peptide libraries will be screened with recombinant GRP94 to identify high- and low-affinity binding peptides. The optimal length and other properties of binder peptides will be deduced from the use of libraries of permutated synthetic-sequences. Consensus binder sequences will then be determined by panning a large complexity phase display library. Binder peptides will then be compared to the peptides preferred by other chaperones, and most importantly to MHC class I- and class II-binding peptides. These experiments will help determine the selectivity of the GRP94-peptide representation pathway.

GRP94 will be genetically engineered to enhance its peptide presenting activity. As described in Example 1, the peptide-binding site of GRP94 has been mapped by a combination of biochemistry and site-directed mutagenesis and the data related to a computer structural model of the chaperone. To further characterize this molecule, the inventor will search for GRP94 versions with altered affinity and/or specificity for peptides and test such engineered versions of GRP94 in tissue culture and then in mouse models for augmenting specific killer T cell responses. It is possible that high affinity binder peptides are better presented because they remain bound to GRP94 during endocytosis. Alternatively, peptides with moderate affinity to GRP94 may be presented preferentially, because they can be transferred to MHC class I more efficiently.

The minimal GRP94 derivative, which can still be taken up by antigen presenting cells and stimulate T cells is described herein. Various macrophages and dendritic cells (lines in culture and ex vivo derived) will be incubated with peptide-loaded recombinant constructs derived from GRP94 and their ability to represent the peptide will be tested by measuring T cell responses in culture. Such a mini-chaperone is more likely to be free of other activities of the full-length chaperone and therefore be more suitable as a tumor vaccine.

Figure 20:
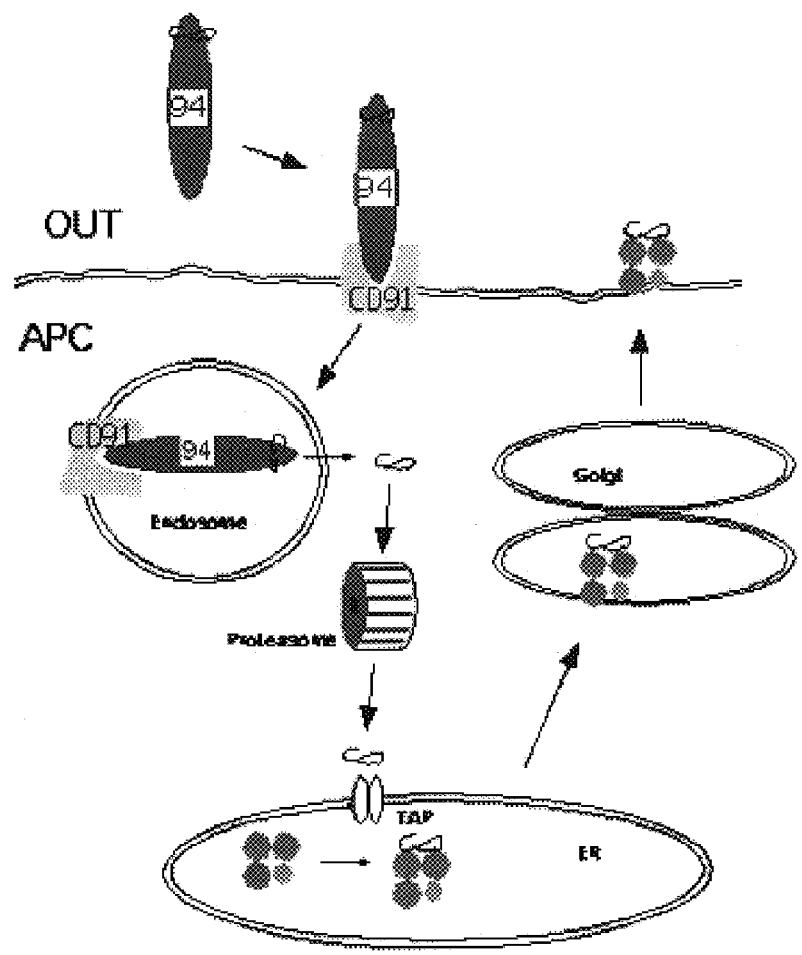
FIG. 20 shows the Srivastava model for presentation of peptides to T cells. A fraction of GRP94 derived from dying tumor cells 10 is loaded with tumor-specific peptide. It binds to CD91 on the plasma membrane of certain dendritic cells and macrophages (APC) and is consequently internalized by receptor-mediated endocytosis. In the endosomal compartment, the peptide is dissociated from GRP94, is extruded to the cytosol of the APC and then is transported via the endoplasmic reticulum peptide transporter (TAP) into the ER lumen, where it is loaded onto newly-synthesized class I molecules 20 and 22. The loaded class I then traffics to the plasma membrane, where it displays the tumor-derived peptide for recognition by T cells. Some peptides may be trimmed by the proteasome 30 after their release from GRP94 and before their loading onto class I molecules.

One way to artificially increase the amount of tumor-specific peptides available for T cell recognition and stimulation is to introduce such peptides as complexes with the protein GRP94 as shown in FIG. 20. GRP94 is a ubiquitous protein that binds peptides, including mutated peptides within tumor cells. The elegant work of Srivastava's lab showed that GRP94 bound to tumor peptides can be used to vaccinate mice which then mount 10-200 fold better T cells responses when challenged with tumors, compare to control mice (see Blachere, N. E., et al., *Heat shock protein-peptide complexes, reconstituted in vitro, elicit peptide-specific cytotoxic T lymphocyte response and tumor immunity*. J. Exp. Med., 1997. 186:1315-1322). The frequency of tumor rejection by GRP94-injected mice is impressive. This approach is now being tested in clinical trials. Its big advantage is the utilization of a self-protein, to which there is no significant immune response, as a means of delivering the peptide antigens.

It has previously been reported that at least two drugs inhibit GRP94's peptide binding activity (see Schulte, T. W., et al., *Interaction of radicicol with members of the heat shock protein 90 family of molecular chaperones*. Mol. Endocrinol., 1999. 13:1435-1448). These studies localized the site of peptide binding to the first 200 amino acids of the protein sequence (see Vogen, S. M., et al., *Radicicol-sensitive peptide binding to the N-terminal portion of GRP94*. J. Biol. Chem. 2002. 277:40742-40750). Using the ability to produce recombinant protein, the inventor showed that peptide binding and inhibitor binding map to distinct sites in GRP94 and importantly, that the peptide specificity of this chaperone differs from the specificity of others, such as BiP or HSP70 as disclosed by Vogen et al. Finally, the GRP94-deficient cells derived from our knockout mouse embryos described in Example 2 can be used as hosts for testing the activity of engineered versions of the proteins.

It is already established that the GRP94-bound peptides are presented to T cells indirectly, via macrophages and/or dendritic cells as described in FIG. 20. These cells take up the injected GRP94 (whether via CD91-dependent endocytosis as described by Binder et al. or via another route as described by Berwin, B., et al., *CD91-Independent Cross-Presentation of GRP94(gp96)-Associated Peptides*. J Immunol, 2002. 168: 4282-4286) transfer the tumor peptide from GRP94 to MHC class I by some ill-defined pathway, and then display the peptide on the surface in complex with class I molecules, for T cell stimulation (see Berwin, B., et al., *Transfer of GRP94*

(Gp96)-*Associated Peptides onto Endosomal MHC Class I Molecules*. Traffic, 2002. 3:358-366).

Figure 21:
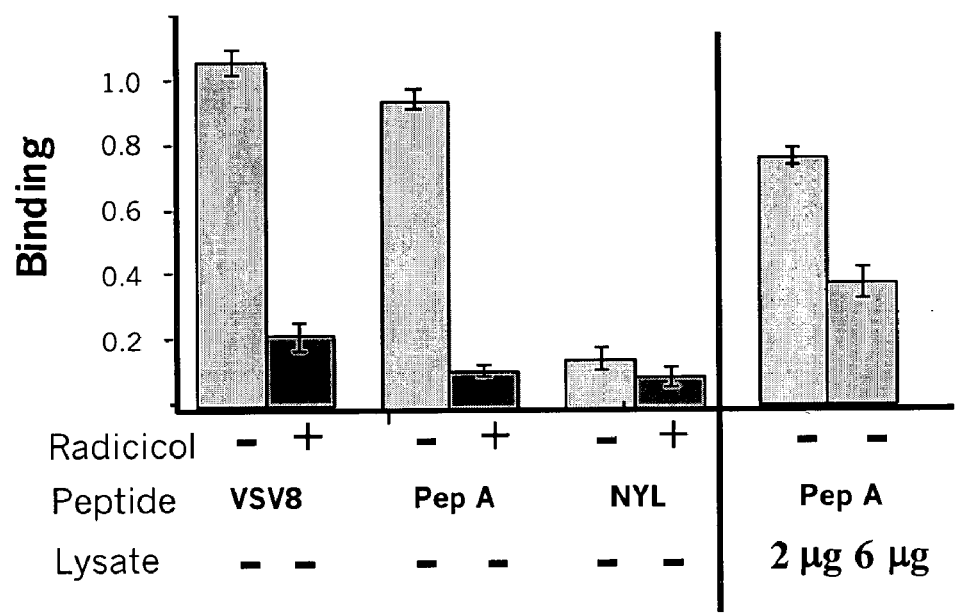
FIG. 21 shows a peptide binding assay. Multi-well plates (96) were coated with the indicated peptides and then incubated with His6 tagged N355, comprising of amino acids 34-355 of GRP94, in the absence or presence of the inhibitor radicicol. Each reaction contained 0.7 µmole chaperone. VSV8 and PepA are known GRP94 binder peptides, whereas NYL is a non-binder. Lysate, amount of total protein in a bacterial lysate, each containing 0.7 µmole chaperone, accounting for only partial inhibition of binding. Binding of chaperone to the peptide-coated plates was detected by HRP-conjugated anti-His antibody.

To define the spectrum of GRP94 binding peptides we propose to use library approaches. We developed a 96-well plate-format binding assay using a recombinant GRP94 version, which should enable us to determine the optimal features of binder peptides as shown in FIG. 21. We will pan a library of chemically synthesized versions of the best-known binder peptides (vsv8: RGYVYQGL (SEQ ID NO: 5); peptide A: KRQIYTDLEMNRLGK (SEQ ID NO: 6), attached to pins or to nitrocellulose in the plate format. The library will consist of progressive truncations from each end of the two peptides and of systematic amino acid substitutions. Specificity of binding will be ascertained by sensitivity to the inhibitor radicicol as described by Vogen et al. In this fashion, we will determine the length and hydrophobicity that are optimal for binding as well as requirements for key side chains. This approach will be further strengthened if a synthetic peptide capability and a robotic assay system are made available for this screening.

Once the optimal length is known, we will employ peptide phage display libraries using libraries already in our possession. Phage displaying GRP94 binding peptides will be isolated and sequenced, in order to derive consensus sequences. Since our assay is quantitative, the resultant peptides will also be rank ordered. The human genome databases will be then mined to find out how often these peptides occur in human proteins, and in what kind of proteins. An important component of this approach will be comparisons of GRP94-binding peptides with peptides known to stimulate T cells. We have a collection of such peptides, each with its corresponding T cell clone or hybridoma, for this purpose. If the majority of GRP94-binding peptides are structurally different from peptides that recognized by T cells, this method of immunization against tumors is not likely to be widely applicable. However, inspection of the small subset of known GRP94-binding peptides suggest that this will not be the case and that there is considerable similarity to peptides recognized by T cells.

Thus far, the minimal peptide-binding domain of GRP94 is amino acids 34 to 221. Using a similar assay as above, we will randomly mutate this sequence at an average hit rate of 1-2 mutations per sequence and select recombinant proteins with reduced affinity for the known peptide VSV8. These will be sequenced to determine all the amino acids that affect peptide binding. Preliminary data using site-directed mutagenesis suggest that Trp 202 and His136 are involved in peptide binding, as well as demonstrating the feasibility of our approach for mapping the binding site.

In parallel, we will engineer GRP94 so that it binds peptides better and/or differently than the naturally occurring protein in order to generate a "designer version" that is more effective in augmentation of T cell responses. Variants with increased peptide affinity may sensitize the immune system when even low levels of peptide-GRP94 are administered. Alternatively, higher affinity may be detrimental, as it may make dissociation of GRP94 from peptide harder in the macrophage/dendritic cell environment. We will therefore screen for mutants that confer altered recognition of peptides.

Once these mutants are characterized in cell-free peptide binding assays, we will test them for peptide presentation to T cells, initially using antigen presenting cells in culture (as described herein) and then by immunization of mice, as described in references by Tamura et al., Basu et al., Suto et al., and Blachere et al.

FIG. 22 provides the nucleic acid and amino acid sequences of wild type GRP94.

REFERENCES FOR EXAMPLE 3

1. Tamura, Y., et al., *Immunotherapy of tumors with autologous tumor-derived heat shock protein preparations*. Science, 1997. 278:117-120.

2. Basu, S., et al., *Necrotic but not apoptotic cell death releases heat shock proteins, which deliver a partial maturation signal to dendritic cells and activate the NF-kappa B pathway*. Int Immunol, 2000. 12:1539-1546.

3. Binder, R. J., D. K. Han, and P. K. Srivastava, *CD*91: *a receptor for heat shock protein gp*96. Nat Immunol, 2000. 1:151-155.

4. Suto, R. and P. K. Srivastava, *A mechanism for the specific immunogenicity of heat shock protein-chaperoned peptides*. Science, 1995.269:1585-1588.

5. Blachere, N. E., et al., *Heat shock protein-peptide complexes, reconstituted in vitro, elicit peptide-specific cytotoxic T lymphocyte response and tumor immunity*. J. Exp. Med., 1997. 186:1315-1322.

6. Velders, M. P., H. Schreiber, and W. M. Kast, *Active immunization against cancer cells: impediments and advances*. Semin Oncol, 1998. 25:69 7-706.

7. Melnick, J., J. L. Dul, and Y. Argon, *Sequential interaction of the chaperones BiP and GRP*94 *with immunoglobulin chains in the endoplasmic reticulum*. Nature, 1994. 370: 373-375.

8. Schulte, T. W., et al., *Interaction of radicicol with members of the heat shock protein* 90 *family of molecular chaperones*. Mol. Endocrinol., 1999. 13:1435-1448.

9. Vogen, S. M., et al., *Radicicol-sensitive peptide binding to the N-terminal portion of GRP*94. J. Biol. Chem. 2002. 277:40742-40750.

10. Berwin, B., et al., *CD*91-*Independent Cross-Presentation of GRP*94(*gp*96)-*Associated Peptides*. J Immunol, 2002. 168:4282-4286.

11. Berwin, B., et al., *Tranfer of GRP*94(*Gp*96)-*Associated Peptides onto Endosomal MHC Class I Molecules*. Traffic, 2002. 3:358-366.

12. Argon, Y. and B. B. Simen, *GRP*94, *an ER chaperone with protein and peptide binding properties*. Semin Cell Dev Biol, 1999. 10:495-505.

13. Baker-LePain, J. C., et al., *GRP*94 (*gp*96) *and GRP*94 *N-terminal geldanamycin binding domain elicit tissue nonrestricted tumor suppression*. J Exp Med, 2002. 196: 1447-1459.

14. Linderoth, N. A., A. Popowicz, and S. Sastry, *Identification of the peptide-binding site in the heat shock chaperone/tumor rejection antigen gp*96 (*Grp*94). J. Biol. Chem., 2000. 275:5472-5477.

While the invention has been described in detail and with reference to specific examples thereof, it will be apparent to one skilled in the art that various changes and modifications can be made therein without departing from the spirit and scope thereof.

What is claimed is:

1. A GRP94 mini chaperone protein, wherein said GRP94 mini chaperone protein is selected from the group consisting of amino acids 55-376 of SEQ ID NO: 2, and amino acids 55-243 of SEQ ID NO: 2.

2. A composition comprising the protein of claim 1, contained within a pharmaceutically acceptable carrier.

3. The composition of claim 2, further comprising a peptide complexed to said GRP94 mini-chaperone protein.

4. The composition of claim 3, wherein said peptide in said complex comprises a tumor specific antigen.

5. The composition of claim 3, wherein said peptide in said complex comprises a viral antigen.

* * * * *

UNITED STATES PATENT AND TRADEMARK OFFICE
CERTIFICATE OF CORRECTION

PATENT NO.       : 7,589,174 B2                                          Page 1 of 1
APPLICATION NO.  : 10/844711
DATED            : September 15, 2009
INVENTOR(S)      : Argon et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1005 days.

Signed and Sealed this

Twenty-first Day of September, 2010

David J. Kappos
*Director of the United States Patent and Trademark Office*

SEQUENCE LISTING

<160> NUMBER OF SEQ ID NOS: 27

<210> SEQ ID NO 1
<211> LENGTH: 2780
<212> TYPE: DNA
<213> ORGANISM: Artificial Sequence
<220> FEATURE:
<223> OTHER INFORMATION: nucleotide sequence human GRP94

<400> SEQUENCE: 1

| | | | | | | |
|---|---|---|---|---|---|---|
| gtgggcggac | cgcgcggctg | gaggtgtgag | gatccgaacc | caggggtggg | gggtggaggc | 60 |
| ggctcctgcg | atcgaagggg | acttgagact | caccggccgc | acgccatgag | ggccctgtgg | 120 |
| gtgctgggcc | tctgctgcgt | cctgctgacc | ttcgggtcgg | tcagagctga | cgatgaagtt | 180 |
| gatgtggatg | gtacagtaga | agaggatctg | ggtaaaagta | gagaaggatc | aaggacggat | 240 |
| gatgaagtag | tacagagaga | ggaagaagct | attcagttgg | atggattaaa | tgcatcacaa | 300 |
| ataagagaac | ttagagagaa | gtcggaaaag | tttgccttcc | aagccgaagt | aacagaatg | 360 |
| atgaaactta | tcatcaattc | attgtataaa | aataaagaga | ttttcctgag | agaactgatt | 420 |
| tcaaatgctt | ctgatgcttt | agataagata | aggctaatat | cactgactga | tgaaaatgct | 480 |
| ctttctggaa | atgaggaact | aacagtcaaa | attaagtgtg | ataaggagaa | gaacctgctg | 540 |
| catgtcacag | acaccggtgt | aggaatgacc | agagaagagt | tggttaaaaa | ccttggtacc | 600 |
| atagccaaat | ctgggacaag | cgagttttta | aacaaaatga | ctgaagcaca | ggaagatggc | 660 |
| cagtcaactt | ctgaattgat | tggccagttt | ggtgtcggtt | tctattccgc | cttccttgta | 720 |
| gcagataagg | ttattgtcac | ttcaaaaaca | aacaacgata | cccagcacat | ctgggagtct | 780 |
| gactccaatg | aatttctgt | aattgctgac | ccaagaggaa | acactctagg | acggggaacg | 840 |
| acaattaccc | ttgtcttaaa | agaagaagca | tctgattacc | ttgaattgga | tacaattaaa | 900 |
| aatctcgtca | aaaaatattc | acagttcata | aactttccta | tttatgtatg | gagcagcaag | 960 |
| actgaaactg | ttgaggagcc | catggaggaa | gaagaagcag | ccaaagaaga | gaaagaagaa | 1020 |
| tctgatgatg | aagctgcagt | agaggaagaa | gaagaagaaa | agaaaccaaa | gactaaaaaa | 1080 |
| gttgaaaaaa | ctgtctggga | ctgggaactt | atgaatgata | tcaaaccaat | atggcagaga | 1140 |
| ccatcaaaag | aagtagaaga | agatgaatac | aaagctttct | acaaatcatt | ttcaaaggaa | 1200 |
| agtgatgacc | ccatggctta | tattcacttt | actgctgaag | gggaagttac | cttcaaatca | 1260 |
| attttatttg | tacccacatc | tgctccacgt | ggtctgtttg | acgaatatgg | atctaaaaag | 1320 |
| agcgattaca | ttaagctcta | tgtgcgccgt | gtattcatca | cagacgactt | ccatgatatg | 1380 |
| atgcctaaat | acctcaattt | tgtcaagggt | gtggtggact | cagatgatct | ccccttgaat | 1440 |
| gtttcccgcg | agactcttca | gcaacataaa | ctgcttaagg | tgattaggaa | gaagcttgtt | 1500 |
| cgtaaaacgc | tggacatgat | caagaagatt | gctgatgata | aatacaatga | tacttttttgg | 1560 |
| aaagaatttg | gtaccaacat | caagcttggt | gtgattgaag | accactcgaa | tcgaacacgt | 1620 |
| cttgctaaac | ttcttaggtt | ccagtcttct | catcatccaa | ctgacattac | tagcctagac | 1680 |
| cagtatgtgg | aaagaatgaa | ggaaaaacaa | gacaaaatct | acttcatggc | tgggtccagc | 1740 |
| agaaaagagc | tgaatctttc | tccatttgtt | gagcgacttc | tgaaaaaggg | ctatgaagtt | 1800 |
| atttacctca | cagaacctgt | ggatgaatac | tgtattcagg | cccttccga | atttgatggg | 1860 |
| aagaggttcc | agaatgttgc | caaggaagga | gtgaagttcg | atgaaagtga | gaaaactaag | 1920 |
| gagagtcgtg | aagcagttga | aaagaatttt | gagcctctgc | tgaattggat | gaaagataaa | 1980 |

-continued

```
gcccttaagg acaagattga aaaggctgtg gtgtctcagc gcctgacaga atctccgtgt    2040
gctttggtgg ccagccagta cggatggtct ggcaacatgg agagaatcat gaaagcacaa    2100
gcgtaccaaa cgggcaagga catctctaca aattactatg cgagtcagaa gaaaacattt    2160
gaaattaatc ccagacaccc gctgatcaga gacatgcttc gacgaattaa ggaagatgaa    2220
gatgataaaa cagttttgga tcttgctgtg gttttgtttg aaacagcaac gcttcggtca    2280
gggtatcttt taccagacac taaagcatat ggagatagaa tagaaagaat gcttcgcctc    2340
agtttgaaca ttgaccctga tgcaaaggtg aagaagagc ccgaagaaga acctgaagag    2400
acagcagaag acacaacaga agacacagag caagacgaag atgaagaaat ggatgtggga    2460
acagatgaag aagaagaaac agcaaaggaa tctacagctg aaaaagatga attgtaaatt    2520
atactctcac catttggatc ctgtgtggag agggaatgtg aaatttacat catttctttt    2580
tgggagagac ttgttttgga tgccccctaa tccccttctc ccctgcactg taaaatgtgg    2640
gattatgggt cacaggaaaa agtgggtttt ttagttgaat tttttttaac attcctcatg    2700
aatgtaaatt tgtactattt aactgactat tcttgatgta aaatcttgtc atgtgtataa    2760
aaataaaaaa gatcccaaat                                                 2780
```

<210> SEQ ID NO 2
<211> LENGTH: 803
<212> TYPE: PRT
<213> ORGANISM: Artificial Sequence
<220> FEATURE:
<223> OTHER INFORMATION: amino acid sequence human GRP94

<400> SEQUENCE: 2

```
Met Arg Ala Leu Trp Val Leu Gly Leu Cys Cys Val Leu Leu Thr Phe
 1               5                   10                  15

Gly Ser Val Arg Ala Asp Asp Glu Val Asp Val Asp Gly Thr Val Glu
                20                  25                  30

Glu Asp Leu Gly Lys Ser Arg Glu Gly Ser Arg Thr Asp Asp Glu Val
         35                  40                  45

Val Gln Arg Glu Glu Glu Ala Ile Gln Leu Asp Gly Leu Asn Ala Ser
     50                  55                  60

Gln Ile Arg Glu Leu Arg Glu Lys Ser Glu Lys Phe Ala Phe Gln Ala
 65                  70                  75                  80

Glu Val Asn Arg Met Met Lys Leu Ile Ile Asn Ser Leu Tyr Lys Asn
                 85                  90                  95

Lys Glu Ile Phe Leu Arg Glu Leu Ile Ser Asn Ala Ser Asp Ala Leu
            100                 105                 110

Asp Lys Ile Arg Leu Ile Ser Leu Thr Asp Glu Asn Ala Leu Ser Gly
        115                 120                 125

Asn Glu Glu Leu Thr Val Lys Ile Lys Cys Asp Lys Glu Lys Asn Leu
    130                 135                 140

Leu His Val Thr Asp Thr Gly Val Gly Met Thr Arg Glu Glu Leu Val
145                 150                 155                 160

Lys Asn Leu Gly Thr Ile Ala Lys Ser Gly Thr Ser Glu Phe Leu Asn
                165                 170                 175

Lys Met Thr Glu Ala Gln Glu Asp Gly Gln Ser Thr Ser Glu Leu Ile
            180                 185                 190

Gly Gln Phe Gly Val Gly Phe Tyr Ser Ala Phe Leu Val Ala Asp Lys
        195                 200                 205

Val Ile Val Thr Ser Lys His Asn Asn Asp Thr Gln His Ile Trp Glu
```

-continued

```
                 210                 215                 220
Ser Asp Ser Asn Glu Phe Ser Val Ile Ala Asp Pro Arg Gly Asn Thr
225                 230                 235                 240

Leu Gly Arg Gly Thr Thr Ile Thr Leu Val Leu Lys Glu Glu Ala Ser
                245                 250                 255

Asp Tyr Leu Glu Leu Asp Thr Ile Lys Asn Leu Val Lys Lys Tyr Ser
                260                 265                 270

Gln Phe Ile Asn Phe Pro Ile Tyr Val Trp Ser Ser Lys Thr Glu Thr
                275                 280                 285

Val Glu Glu Pro Met Glu Glu Glu Ala Ala Lys Glu Glu Lys Glu
290                 295                 300

Glu Ser Asp Asp Glu Ala Ala Val Glu Glu Glu Glu Glu Lys Lys
305                 310                 315                 320

Pro Lys Thr Lys Lys Val Glu Lys Thr Val Trp Asp Trp Glu Leu Met
                325                 330                 335

Asn Asp Ile Lys Pro Ile Trp Gln Arg Pro Ser Lys Glu Val Glu Glu
                340                 345                 350

Asp Glu Tyr Lys Ala Phe Tyr Lys Ser Phe Ser Lys Glu Ser Asp Asp
                355                 360                 365

Pro Met Ala Tyr Ile His Phe Thr Ala Glu Gly Glu Val Thr Phe Lys
                370                 375                 380

Ser Ile Leu Phe Val Pro Thr Ser Ala Pro Arg Gly Leu Phe Asp Glu
385                 390                 395                 400

Tyr Gly Ser Lys Lys Ser Asp Tyr Ile Lys Leu Tyr Val Arg Arg Val
                405                 410                 415

Phe Ile Thr Asp Asp Phe His Asp Met Met Pro Lys Tyr Leu Asn Phe
                420                 425                 430

Val Lys Gly Val Val Asp Ser Asp Asp Leu Pro Leu Asn Val Ser Arg
                435                 440                 445

Glu Thr Leu Gln Gln His Lys Leu Leu Lys Val Ile Arg Lys Lys Leu
                450                 455                 460

Val Arg Lys Thr Leu Asp Met Ile Lys Lys Ile Ala Asp Asp Lys Tyr
465                 470                 475                 480

Asn Asp Thr Phe Trp Lys Glu Phe Gly Thr Asn Ile Lys Leu Gly Val
                485                 490                 495

Ile Glu Asp His Ser Asn Arg Thr Arg Leu Ala Lys Leu Leu Arg Phe
                500                 505                 510

Gln Ser Ser His His Pro Thr Asp Ile Thr Ser Leu Asp Gln Tyr Val
                515                 520                 525

Glu Arg Met Lys Glu Lys Gln Asp Lys Ile Tyr Phe Met Ala Gly Ser
                530                 535                 540

Ser Arg Lys Glu Ala Glu Ser Ser Pro Phe Val Glu Arg Leu Leu Lys
545                 550                 555                 560

Lys Gly Tyr Glu Val Ile Tyr Leu Thr Glu Pro Val Asp Glu Tyr Cys
                565                 570                 575

Ile Gln Ala Leu Pro Glu Phe Asp Gly Lys Arg Phe Gln Asn Val Ala
                580                 585                 590

Lys Glu Gly Val Lys Phe Asp Glu Ser Glu Lys Thr Lys Glu Ser Arg
                595                 600                 605

Glu Ala Val Glu Lys Glu Phe Glu Pro Leu Leu Asn Trp Met Lys Asp
                610                 615                 620

Lys Ala Leu Lys Asp Lys Ile Glu Lys Ala Val Val Ser Gln Arg Leu
625                 630                 635                 640
```

```
Thr Glu Ser Pro Cys Ala Leu Val Ala Ser Gln Tyr Gly Trp Ser Gly
                645                 650                 655

Asn Met Glu Arg Ile Met Lys Ala Gln Ala Tyr Gln Thr Gly Lys Asp
            660                 665                 670

Ile Ser Thr Asn Tyr Tyr Ala Ser Gln Lys Lys Thr Phe Glu Ile Asn
        675                 680                 685

Pro Arg His Pro Leu Ile Arg Asp Met Leu Arg Arg Ile Lys Glu Asp
    690                 695                 700

Glu Asp Lys Thr Val Leu Asp Leu Ala Val Val Leu Phe Glu Thr
705                 710                 715                 720

Ala Thr Leu Arg Ser Gly Tyr Leu Leu Pro Asp Thr Lys Ala Tyr Gly
                725                 730                 735

Asp Arg Ile Glu Arg Met Leu Arg Leu Ser Leu Asn Ile Asp Pro Asp
            740                 745                 750

Ala Lys Val Glu Glu Pro Glu Glu Pro Glu Glu Thr Ala Glu
        755                 760                 765

Asp Thr Thr Glu Asp Thr Glu Gln Asp Glu Asp Glu Met Asp Val
770                 775                 780

Gly Thr Asp Glu Glu Glu Thr Ala Lys Glu Ser Thr Ala Glu Lys
785                 790                 795                 800

Asp Glu Leu

<210> SEQ ID NO 3
<211> LENGTH: 5
<212> TYPE: PRT
<213> ORGANISM: Artificial Sequence
<220> FEATURE:
<223> OTHER INFORMATION: n-terminus of mature protein

<400> SEQUENCE: 3

Asp Asp Glu Val Asp
 1               5

<210> SEQ ID NO 4
<211> LENGTH: 4
<212> TYPE: PRT
<213> ORGANISM: Artificial Sequence
<220> FEATURE:
<223> OTHER INFORMATION: ER retrieval signal

<400> SEQUENCE: 4

Lys Asp Glu Leu
 1

<210> SEQ ID NO 5
<211> LENGTH: 8
<212> TYPE: PRT
<213> ORGANISM: Artificial Sequence
<220> FEATURE:
<223> OTHER INFORMATION: octamer from N protein

<400> SEQUENCE: 5

Arg Gly Tyr Val Tyr Gln Gly Leu
 1               5

<210> SEQ ID NO 6
<211> LENGTH: 15
<212> TYPE: PRT
<213> ORGANISM: Artificial Sequence
<220> FEATURE:
<223> OTHER INFORMATION: 15-mer from glycoprotein
```

-continued

```
<400> SEQUENCE: 6

Lys Arg Gln Ile Tyr Thr Asp Leu Glu Met Asn Arg Leu Gly Lys
1               5                   10                  15

<210> SEQ ID NO 7
<211> LENGTH: 7
<212> TYPE: PRT
<213> ORGANISM: Artificial Sequence
<220> FEATURE:
<223> OTHER INFORMATION: heptamer precedes Ala34 or mature N34-55
      sequence

<400> SEQUENCE: 7

Pro Tyr Asn Gly Thr Gly Ser
1               5

<210> SEQ ID NO 8
<211> LENGTH: 8
<212> TYPE: PRT
<213> ORGANISM: Artificial Sequence
<220> FEATURE:
<223> OTHER INFORMATION: OVA 257-264

<400> SEQUENCE: 8

Ser Ile Ile Asn Phe Glu Lys Leu
1               5

<210> SEQ ID NO 9
<211> LENGTH: 9
<212> TYPE: PRT
<213> ORGANISM: Artificial Sequence
<220> FEATURE:
<223> OTHER INFORMATION: RAH

<400> SEQUENCE: 9

Arg Ala His Tyr Asn Ile Val Thr Phe
1               5

<210> SEQ ID NO 10
<211> LENGTH: 10
<212> TYPE: PRT
<213> ORGANISM: Artificial Sequence
<220> FEATURE:
<223> OTHER INFORMATION: PSA 16

<400> SEQUENCE: 10

Val Leu Val Ala Ser Arg Gly Arg Ala Val
1               5                   10

<210> SEQ ID NO 11
<211> LENGTH: 23
<212> TYPE: PRT
<213> ORGANISM: Artificial Sequence
<220> FEATURE:
<223> OTHER INFORMATION: PSA 141

<400> SEQUENCE: 11

Phe Leu Thr Pro Lys Lys Leu Gln Cys Val Asp Leu His Val Ile Ser
1               5                   10                  15

Asn Asp Val Cys Ala Gln Val
            20

<210> SEQ ID NO 12
<211> LENGTH: 9
<212> TYPE: PRT
```

```
<213> ORGANISM: Artificial Sequence
<220> FEATURE:
<223> OTHER INFORMATION: MAGE 3

<400> SEQUENCE: 12

Phe Leu Trp Gly Pro Arg Ala Leu Val
 1               5

<210> SEQ ID NO 13
<211> LENGTH: 10
<212> TYPE: PRT
<213> ORGANISM: Artificial Sequence
<220> FEATURE:
<223> OTHER INFORMATION: Ras p5-14

<400> SEQUENCE: 13

Lys Leu Val Val Val Gly Ala Gly Gly Val
 1               5                  10

<210> SEQ ID NO 14
<211> LENGTH: 71
<212> TYPE: PRT
<213> ORGANISM: Artificial Sequence
<220> FEATURE:
<223> OTHER INFORMATION: Canis familiaris

<400> SEQUENCE: 14

Glu Leu Thr Val Lys Ile Lys Cys Asp Lys Glu Lys Asn Leu Leu His
 1               5                  10                  15

Val Thr Asp Thr Gly Val Gly Met Thr Arg Glu Glu Leu Val Lys Asn
                20                  25                  30

Leu Gly Thr Ile Ala Lys Ser Gly Thr Ser Glu Phe Leu Asn Lys Met
            35                  40                  45

Thr Glu Ala Gln Glu Asp Gly Gln Ser Thr Ser Glu Leu Ile Gly Gln
        50                  55                  60

Phe Gly Val Gly Phe Tyr Ser
65                  70

<210> SEQ ID NO 15
<211> LENGTH: 71
<212> TYPE: PRT
<213> ORGANISM: Artificial Sequence
<220> FEATURE:
<223> OTHER INFORMATION: Cavia porcellus

<400> SEQUENCE: 15

Glu Leu Thr Val Lys Ile Lys Cys Asp Lys Glu Lys Asn Leu Leu His
 1               5                  10                  15

Val Thr Asp Thr Gly Val Gly Met Thr Arg Glu Glu Leu Val Lys Asn
                20                  25                  30

Leu Gly Thr Ile Ala Lys Ser Gly Thr Ser Glu Phe Leu Asn Lys Met
            35                  40                  45

Ala Glu Ala Gln Glu Asp Gly Gln Ser Thr Ser Glu Leu Ile Gly Gln
        50                  55                  60

Phe Gly Val Gly Phe Tyr Ser
65                  70

<210> SEQ ID NO 16
<211> LENGTH: 71
<212> TYPE: PRT
<213> ORGANISM: Artificial Sequence
<220> FEATURE:
<223> OTHER INFORMATION: Homo sapiens
```

<400> SEQUENCE: 16

Glu Leu Thr Val Lys Ile Lys Cys Asp Lys Glu Lys Asn Leu Leu His
1               5                   10                  15

Val Thr Asp Thr Gly Val Gly Met Thr Arg Glu Glu Leu Val Lys Asn
            20                  25                  30

Leu Gly Thr Ile Ala Lys Ser Gly Thr Ser Glu Phe Leu Asn Lys Met
        35                  40                  45

Thr Glu Ala Gln Glu Asp Gly Gln Ser Thr Ser Glu Leu Ile Gly Gln
    50                  55                  60

Phe Gly Val Gly Phe Tyr Ser
65                  70

<210> SEQ ID NO 17
<211> LENGTH: 71
<212> TYPE: PRT
<213> ORGANISM: Artificial Sequence
<220> FEATURE:
<223> OTHER INFORMATION: erp

<400> SEQUENCE: 17

Glu Leu Thr Val Lys Ile Lys Cys Asp Lys Glu Lys Asn Leu Leu His
1               5                   10                  15

Val Thr Asp Thr Gly Val Gly Met Thr Arg Glu Glu Leu Val Lys Asn
            20                  25                  30

Leu Gly Thr Ile Ala Lys Ser Gly Thr Ser Glu Phe Leu Asn Lys Met
        35                  40                  45

Thr Glu Ala Gln Glu Asp Gly Gln Ser Thr Ser Glu Leu Ile Gly Gln
    50                  55                  60

Phe Gly Val Gly Phe Tyr Ser
65                  70

<210> SEQ ID NO 18
<211> LENGTH: 72
<212> TYPE: PRT
<213> ORGANISM: Artificial Sequence
<220> FEATURE:
<223> OTHER INFORMATION: Drosophila melanogaster

<400> SEQUENCE: 18

Glu Leu His Ile Arg Ile Lys Ala Asp Lys Glu Asn Lys Ala Leu His
1               5                   10                  15

Ile Met Asp Ser Gly Ile Gly Met Thr His Gln Asp Leu Ile Asn Asn
            20                  25                  30

Leu Gly Thr Ile Ala Lys Ser Gly Thr Ala Asp Phe Leu Ala Lys Met
        35                  40                  45

Gln Asp Pro Ser Lys Ser Glu Gly Leu Asp Met Asn Asp Met Ile Gly
    50                  55                  60

Gln Phe Gly Val Gly Phe Tyr Ser
65                  70

<210> SEQ ID NO 19
<211> LENGTH: 71
<212> TYPE: PRT
<213> ORGANISM: Artificial Sequence
<220> FEATURE:
<223> OTHER INFORMATION: Caenorhabditis elegans

<400> SEQUENCE: 19

Glu Met Ser Val Lys Ile Lys Ala Asp Arg Glu Asn Arg Leu Leu His

-continued

```
                1               5                  10                 15
Ile Thr Asp Thr Gly Val Gly Met Thr Arg Gln Asp Leu Ile Asn Asn
                    20                 25                 30
Leu Gly Thr Ile Ala Arg Ser Gly Thr Ser Glu Phe Leu Ser Lys Leu
            35                 40                 45
Met Asp Thr Ala Thr Ser Ser Asp Gln Gln Gln Asp Leu Ile Gly Gln
    50                 55                 60
Phe Gly Val Gly Phe Tyr Ala
65                  70

<210> SEQ ID NO 20
<211> LENGTH: 66
<212> TYPE: PRT
<213> ORGANISM: Artificial Sequence
<220> FEATURE:
<223> OTHER INFORMATION: Hordeum gramineae

<400> SEQUENCE: 20

Lys Leu Glu Ile Gln Ile Lys Leu Asp Lys Glu Asn Lys Ile Leu Ser
1               5                  10                 15
Ile Arg Asp Arg Gly Val Gly Met Thr Lys Glu Asp Leu Ile Lys Asn
                    20                 25                 30
Leu Gly Thr Ile Ala Lys Ser Gly Thr Ser Ala Phe Val Glu Lys Met
            35                 40                 45
Gln Thr Gly Gly Asp Leu Asn Leu Ile Gly Gln Phe Gly Val Gly Phe
    50                 55                 60
Tyr Ser
65

<210> SEQ ID NO 21
<211> LENGTH: 66
<212> TYPE: PRT
<213> ORGANISM: Artificial Sequence
<220> FEATURE:
<223> OTHER INFORMATION: cros

<400> SEQUENCE: 21

Lys Leu Glu Ile Gln Ile Lys Leu Asp Lys Glu Lys Lys Ile Leu Ser
1               5                  10                 15
Ile Arg Asp Arg Gly Ile Gly Met Thr Lys Glu Asp Leu Ile Lys Asn
                    20                 25                 30
Leu Gly Thr Ile Ala Lys Ser Gly Thr Ser Ala Phe Val Glu Lys Met
            35                 40                 45
Gln Thr Ser Gly Asp Leu Asn Leu Ile Gly Gln Phe Gly Val Gly Phe
    50                 55                 60
Tyr Ser
65

<210> SEQ ID NO 22
<211> LENGTH: 66
<212> TYPE: PRT
<213> ORGANISM: Artificial Sequence
<220> FEATURE:
<223> OTHER INFORMATION: Homo sapiens

<400> SEQUENCE: 22

Glu Leu His Ile Asn Leu Ile Pro Asn Lys Gln Asp Arg Thr Leu Thr
1               5                  10                 15
Ile Val Asp Thr Gly Ile Gly Met Thr Lys Ala Asp Leu Ile Asn Asn
                    20                 25                 30
```

Leu Gly Thr Ile Ala Lys Ser Gly Thr Lys Ala Phe Met Glu Ala Leu
        35                  40                  45

Gln Ala Gly Ala Asp Ile Ser Met Ile Gly Gln Phe Gly Val Gly Phe
    50                  55                  60

Tyr Ser
65

<210> SEQ ID NO 23
<211> LENGTH: 66
<212> TYPE: PRT
<213> ORGANISM: Artificial Sequence
<220> FEATURE:
<223> OTHER INFORMATION: Rattus norvegicus

<400> SEQUENCE: 23

Glu Leu Lys Ile Asp Ile Ile Pro Asn Pro Gln Ala Thr Leu Thr
1               5                   10                  15

Leu Val Asp Thr Gly Ile Gly Met Thr Lys Ala Asp Leu Ile Asn Asn
            20                  25                  30

Leu Gly Thr Ile Ala Lys Ser Gly Thr Lys Ala Phe Met Glu Ala Leu
        35                  40                  45

Gln Ala Gly Ala Asp Ile Ser Met Ile Gly Gln Phe Gly Val Gly Phe
    50                  55                  60

Tyr Ser
65

<210> SEQ ID NO 24
<211> LENGTH: 66
<212> TYPE: PRT
<213> ORGANISM: Artificial Sequence
<220> FEATURE:
<223> OTHER INFORMATION: Caenorhabditis elegans

<400> SEQUENCE: 24

Glu Leu Phe Ile Lys Ile Thr Pro Asn Lys Glu Gln Lys Thr Leu Thr
1               5                   10                  15

Ile Met Asp Thr Gly Ile Gly Met Thr Lys Ala Asp Leu Val Asn Asn
            20                  25                  30

Leu Gly Thr Ile Ala Lys Ser Gly Thr Lys Ala Phe Met Glu Ala Leu
        35                  40                  45

Gln Ala Gly Ala Asp Ile Ser Met Ile Gly Gln Phe Gly Val Gly Phe
    50                  55                  60

Tyr Ser
65

<210> SEQ ID NO 25
<211> LENGTH: 66
<212> TYPE: PRT
<213> ORGANISM: Artificial Sequence
<220> FEATURE:
<223> OTHER INFORMATION: Cadida albicans

<400> SEQUENCE: 25

Glu Leu Phe Ile Arg Ile Ile Pro Gln Lys Asp Gln Lys Val Leu Glu
1               5                   10                  15

Ile Arg Asp Ser Gly Ile Gly Met Thr Lys Ala Asp Leu Val Asn Asn
            20                  25                  30

Leu Gly Thr Ile Ala Lys Ser Gly Thr Lys Ser Phe Met Glu Ala Leu
        35                  40                  45

```
Ser Ala Gly Ala Asp Val Ser Met Ile Gly Gln Phe Gly Val Gly Phe
        50                  55                  60
Tyr Ser
 65

<210> SEQ ID NO 26
<211> LENGTH: 66
<212> TYPE: PRT
<213> ORGANISM: Artificial Sequence
<220> FEATURE:
<223> OTHER INFORMATION: Mycoplasma yeatsii

<400> SEQUENCE: 26

Asp Leu Phe Ile Arg Ile Thr Pro Asp Lys Glu Asn Lys Ile Leu Thr
 1               5                  10                  15
Ile Arg Asp Thr Gly Ile Gly Met Thr Lys Asn Asp Leu Ile Asn Asn
                20                  25                  30
Leu Gly Val Ile Ala Lys Ser Gly Thr Lys Gln Phe Met Glu Ala Ala
            35                  40                  45
Ala Ser Gly Ala Asp Ile Ser Met Ile Gly Gln Phe Gly Val Gly Phe
        50                  55                  60
Tyr Ser
 65

<210> SEQ ID NO 27
<211> LENGTH: 15
<212> TYPE: PRT
<213> ORGANISM: Artificial Sequence
<220> FEATURE:
<223> OTHER INFORMATION: VSV G protein

<400> SEQUENCE: 27

Leu Ser Ser Leu Phe Arg Pro Lys Arg Pro Ile Tyr Lys Ser
 1               5                  10                  15
```